(12) United States Patent
Bruice et al.

(10) Patent No.: US 6,169,176 B1
(45) Date of Patent: Jan. 2, 2001

(54) DEOXYNUCLEIC ALKYL THIOUREA COMPOUNDS AND USES THEREOF

(75) Inventors: Thomas C. Bruice, Santa Barbara, CA (US); Arya P. Dev, Clemson, SC (US)

(73) Assignee: The Regents of the University of California, Oakland, CA (US)

( * ) Notice: Under 35 U.S.C. 154(b), the term of this patent shall be extended for 0 days.

(21) Appl. No.: 09/407,675

(22) Filed: Sep. 28, 1999

Related U.S. Application Data

(63) Continuation-in-part of application No. 09/347,443, filed on Jul. 2, 1999.
(60) Provisional application No. 60/091,481, filed on Jul. 2, 1998, and provisional application No. 60/111,800, filed on Dec. 11, 1998.

(51) Int. Cl.$^7$ .......................... C07H 21/00; C07H 21/04; C07H 21/02; C12Q 1/70

(52) U.S. Cl. .................. 536/25.3; 536/24.33; 536/24.31; 536/24.3; 536/23.1; 536/24.5; 435/6

(58) Field of Search ............................... 435/6, 91.1, 91.3, 435/375; 536/23.1, 23.2, 24.5, 24.3, 24.33, 24.31, 25.3; 514/44

(56) References Cited

PUBLICATIONS

Branch, "A good antisenese is hard to find"TIBS23, pp.45–50 2/1998.*
Vandendriessche et al. "Synthesis, Enzymatic Stability and Base–pairing Properties of Oligothymidylates Containing Thymidine Dimers with Different N–Substituted Guanidine Linkages", J. Chem. Soc. Perkin Trans, pp.1567–1575 1993.*
Browne et al. "Binding Studies of Cationic Thymidyl Deoxyribonucleic guanidine to RNA Homopolynucleotides", Proc. Natl. Acad. Sci. vol 92, pp. 7051–7055 7/1995.*
Crooke et al. Antisense Research and Application, pp.1–50 7/1998.*
Agrawal, Sudhir et al., "Mixed–Backbone Oligonucleotides Containing Phophorothioate and Methylphosphonate Linkages as Second Generation Antisense Oligonucleotide," *Nucleosides and Nuclesides and Nucleotides*, 1997, 16(7–9):927–36. (Exhibit 1).
Alama, Angela et al., "Antisense Oligonucleotides as Therapeutic Agents," *Pharmacological Research*, 1997, 36(3):171–8. (Exhibit 2).
Blasko, Andrei et al., "Association of Short Strand DNA Oligomers with Guanidinium–Linked Nucleosides. A Kinetic and Thermodynamic Study," *Journal of the American Chemical Society*, Aug. 28, 1996, 118(34):7892–9, (Exhibit 3).
Blasko, Andrei et al., "Fidelity of Binding of the Guanidinium Nucleic Acid (DNG) d(Tg)$_4$–T–azido With Short Strand DNA Oligomers (A$_5$G$_3$A$_5$, GA$_4$G$_3$A$_4$G, G$_2$A$_3$G$_3$A$_3$G$_2$, G$_2$A$_2$G$_5$A$_2$G$_2$). A Kinetic And Thermodynamic Study," Biochemistry, 1997, 36:7821–31. (Exhibit 4).
Blattler, Monika O. et al., "Distorting Duplex DNA by Dimethylenesulfone Substitution: A New Class of "Transition State Analog" Inhibitors for Restriction Enzymes," *Journal of the American Chemical Society*, Mar. 25, 1998, 120:2674–5. (Exhibit 5).
Bloodworth, A. J. et al., "I,I'–Thiocarbonyldi–2,2'–pyridone. A New Useful Reagent for Functional Group Conversions Under Essentially Neutral Conditions," *The Journal of Organic Chemistry*, Jun. 27, 1986, 51(13):2613–5. (Exhibit 6).

(List continued on next page.)

Primary Examiner—Robert A. Schwartzman
Assistant Examiner—Karen A. LaCourciere
(74) *Attorney, Agent, or Firm*—Mandel & Adriano

(57) ABSTRACT

The invention provides novel deoxynucleic alkyl thiourea (dNXt) oligonucleotide compounds for use in antisense or antigene therapy.

8 Claims, 31 Drawing Sheets

OTHER PUBLICATIONS

Browne, Kenneth A. et al, "Binding Studies of Cationic Thymidyl Deoxyribonucleic Guanidine to RNA Homopolynucleotides," *Proc. Natl. Acad. Sci. USA*, Jul. 1995, 92:1051–55. (Exhibit 7).

Crooke, Rosanne M., "In Vitro Toxicology and Pharmacokinetics of Antisense Oligonucleotides," *Anti–Cancer Drugs Design*, Nov. 1991, 6(5):609–46. (Exhibit 8).

Crooke, Stanley T. "Therapeutic Apllications of Oligonucleotides," *Annual Review of Pharmacology and Toxicology*, 1992, 32:329–76. (Exhibit 9).

De Mesmaeker, Alain et al., "Amide Backbones with Conformationally Restricted Furanose Rings: Highly Improved Affinity of the Modified Oligonucleotides for Their RNA Complements," *Angewandte Chemie*, 1996, 35(23/24):2790–4. (Exhibit 10).

De Mesmaeker, Alain et al., "Backbone Modifications for Antisense Oligonucleotides," *Pure and Applied Chemistry*, 1997, 69(3):437–40. (Exhibit 11).

De Mesmaeker, Alain et al., "Backbone Modifications in Oligonucleotides and Peptide Nucleic Acid System," *Current Opinion in Structural Biology*, 1995, 5(1):343–55. (Exhbit 12).

Dempcy, Robert O. et al., "Design and Synthesis of Deoxynucleic Guanidine: A Polycation Analogue of DNA (Antisense/Antigene/Hybrid Duplex/Triple Helix)," *Proc. Natl. Acad. Sci. USA*, Aug. 1994, 91:7864–8. (Exhibit 13).

Dempcy, Robert O. et al., "Design and Synthesis of Ribonucleic Guanidine: A Polycationic Analog of RNA (antisense/Antigene/Triple Helix)," *Proc. Natl. Acad. Sci. USA*, Apr. 1996, 93:4326–30. (Exhibit 14).

Dempcy, Robert O. et al., "Synthesis of a Thymidyl Pentamer of Deoxyribonucleic Guanidine and Binding Studies with DNA Homopolynucleotides (Antisense/Antigene/Hybrid Duplex/Triple Helix)," *Proc. Natl. Acad. Sci USA*, Jun. 1995, 92;6097–101. (Exhibit 15).

Dempcy, Robert O. et al., "Synthesis of the Polycation Thymidyl DNG, Its Fidelity in Binding Polyanionic DNA/RNA, and the Stability and Nature of the Hybrid complexes," *Journal of the American Chemical Society*, Jun. 7, 1995, 117:6140–1. (Exhibit 16).

Egholm, Michael et al., "Peptide Nucleic Acids (PNA), Oligonucleotide Analogues with an Achiral Peptide Backbone," *Journal of American Chemical Society*, Feb. 26, 1992, 114:1895–7, (Exhibit 17).

Fathi, Reza et al., "(Aminomethyl)Phosphonate Derivatives of Oligonucleotides," *Bioconjugate Chemistry*, 1994, 5:47–47. (Exhibit 18).

Gryaznov, Sergei and Jer–Kang Chen, "Oligodeoxyribonucleotide N3' P5' Phosphoramidates: Synthesis and Hybridization Properties," *Journal of American Chemical Society*, Apr. 6, 1994, 116:3143–4, (Exhibit 19).

Iyer, Radhakrishnan P. et al., "Synthesis, Biophysical Properties, and Stability Studies of Mixed Backbone Oligonucleotides Containing Segments of Methylphosphotriester Internucleotidic Linkages," *Tetrahedron*, 1996, 52(46):14419–36. (Exhibit 20).

James, Kenneth D. et al., "Incorporation of 5'–N–BOC–2', 5'–Dideoxynucleosided–3'–O–Phosphoramidites into Oligonucleotides by Automated Synthesis," *Nucleosides and Nucleotides*, 1997, 16(10–11):1821–36, (Exhibit 21).

Jones, Robert J. et al., "Synthesis and Binding Properties of Pyrimidine Oligodeoxynucleoside Analogs Containings Neutral Phosphodiester Replacements: The Formacetal and 3'–Thioformacetal Internucleoside Linkages," *The Journal of Organic Chemistry*, 1993, 58:2983–91. (Exhibit 22).

Jung, Paul M. et al., "Hybridization of Alternating Cationic/Anionic Oligonucleotides to RNA Segments," *Nucleosides and Nucleotides*, 1994, 13(6–7):1597–1607, (Exhibit 23).

Letsinger, Robert L. et al., "Cationic Oligonucleotides," *Journal of the American Chemical Society*, 1998, 110:4470–1. (Exhibit 24).

Marshall, W. S. and M. H. Caruthers, "Phosphorodithioat DNA as a Potential Therapeutic Drug," Science, Mar. 12, 1993, 259:1564–70. (Exhibit 25).

Miller, P. S. and P.O.P Ts'o, "A New Approach to Chemotherapy Based on Molecular Biology and Nucleic Acid Chemistry: Matagen (Masking Tape For Gene Expression)," *Anti–Cancer Drug Design*, Oct. 1987, 2(2):117–28 , (Exhibit 26).

Milligan, John F. et al., "Current Concepts in Antisense Drug Design," *Journal of Medicinal Chemistry*, Jul. 9, 1993, 36(14):1923–37. (Exhibit 27).

Morvan, F. et al., "Comparative Evaluation of Seven Oligonucleotide Analogues as Pontential Antisense Agents," *Journal of Medicinal Chemistry*, Jan. 22, 1993, 36(2):280–7. (Exhibit 28).

Nielsen, Peter E. and Gerald Haaima, "Peptide Nucleic Acid (PNA). A DNA Mimic with a Pseudopeptide Backbone," *Chemical Society Reviews*, 1997, 26(2)73–8. (Exhibit 29).

Peyman, Anusch et al., "Phosphonic Ester Nucleic Acids (PHONAs): Olignucleotide Analogues with an Achiral Phosphonic Acid Ester Backbone," *Angewandte Chemie*, 1996, 35(22):2636:40. (Exhbit 30).

Riley, Monica et al., "Physical and Chemical Characterization of Two–and Three–Stranded Adenine–Thymine and Adenine–Uracil Homopolymer Complexes," *Jounal of Molecular Biology*, Sep. 1966, 20:359–389. (Exhibit 32).

Rougee, M. et al., "Kinetics and Thermodynamics of Triple–Helix Formation: Effects of Ionic Strength and Mismatches," *Biochemistry*, Sep. 29, 1992, 31(38):9269–78, (Exhibit 33).

Sanghvi, Yogesh S. et al., "Concept, Discovery and Development of MMI Linkage: Story of a Novel Linkage for Antisense Constructs," *Nucleosides and Nucleotides*, 1997, 16(7–9):907–16. (Exhibit 34).

Sood, Anup et al., "Boron–Containing Nucleic Acids: Synthesis of Cyanoborane Adducts of 2'–Deoxynucleosides," *Journal of American Chemical Society*, 1989, 111:9234–5. (Exhibit 35).

Spielvogel, Bernard F. et al., "From Boron Analogues of Amino Acids to Boronated DNA: Potential New Pharmaceuticals and Neutron Capture Agents," *Pure and Applied Chemistry*, 1991, 63(3):415–18. (Exhibit 36).

Stein, C. A. and Y. –C. Cheng, "Antisense Oligonucleotides as Therapeutic Agents –Is the Bullet Really Magical?," Science, Aug. 20, 1993, 261:1004–12. (Exhibit 37).

Stichak, Eugene P. et al., "Uncharged Stereoregular Nucleic Acid Analogues. 1. Synthesis of a Cytosine–Containing Oligomer with Carbamate Internucleoside Linkages," *The Journal of Organic Chemistry*, 1987, 52:4202–6 (Exhibit 38).

Temsamani, Jamal and Philippe Guinot, "Antisense Oligonucleotides: A New Therapeutic Approach," *Biological and Apllied Biochemistry*, Aug. 1997, 26 (1):65–71. (Exhibit 39).

Thibon, Jacques et al., "Syntheisis of Silicon Analogues of Acyclonucleotides Incorporable in Oligonucleotide Solid–Phase Synethesis," *The Journal of Organic Chemistry*, 1997, 62:4635–42. (Exhibit 40).

Uhlmman, eugen and Anusch Peyman, "Antisense Oligonucleotides: A New Therapeutic Principle," *Chemical Reviews*, Jun. 1990, 90(4):544–84. (Exhibit 41).

Vasseur, Jean–Jacques et al., "Oligonucleosides: Synthesis of a Novel methylhydroxylamine–Linked Nucleoside Dimer and Its Incorporation into Antisense Sequences," *Journal of American Chemical Society*, 1992, 114:4006–7. (Exhibit 42).

Artman, Michael and Jay S. Roth, "Chromosomal RNA: An Artifact of Preparation?" *Journal of Molecular Biology*, Sep. 1971, 60(2):291–301. (Exhibit 43).

Arya, Dev P. and Thomas C. Bruice, "Positively Charged Deoxynucleic Methylthioureas: Synthesis and Binding Properties of Pentameric Thymidyl Methylthiourea," *Journal of the American Chemical Society*, 1998, 120:12419–27. (Exhibit 44).

Arya. Dev P. and Thomas C. Bruice, "Triple–Helix Fomation of DNA Oligomers with Methylthiourea Linked Nucleoside (DNmt): A Kinetic and Thermodynamic Analysis," *Pro. Natl. Acad. Sci. USA*, Apr. 1999, 96:4384–9. (Exhibit 45).

Barawkar, Dinesh A. and Thomas C. Bruce, "Synthesis, Biophysical Properties, and Nuclease Resistance Properties of Mixed Backbone Oligodeoxynucleotides Containing Cationic Internucleoside Guanidinium Linkages: Deoxynucleic Guanidine/DNA Chimeras," *Proc. Natl. Acad. Sci. USA*, (Exhibit 46).

Bennett, C. Frank, "Antisense Oligonucleotides: Is the Glass Half Full or Half Empty?" *Biochemical Pharmacology*, 1998, 55:9–19. (Exhibit 47).

Kim, Sunggak and Kyu Yang Yi, "1,1'–Thiocarbonyldi–2, 2'–Pyridone. A New Useful Reagent for Functional Group Conversions Under Essentially Neutral Conditions," *The Journal of Orgainic Chemistry*, 1986, 51:2613–5. (Exhibit 48).

Levis, Joel T. et al., "Cellular Uptake of Oligodeoxyribonucleoside Methylphosphonates," *Antsense Research and Development*, 1995:251–9. (Exhibit 49).

Manzini, Giorgio et al., "Triple Hilix Formation by Oligopurine–Oligopyrimidine DNA Fragment Electrophoretic and Thermodynamic Behavior," *Journal of Molecular Biology*, 1990, 213:833–43. (Exhibit 50).

* cited by examiner

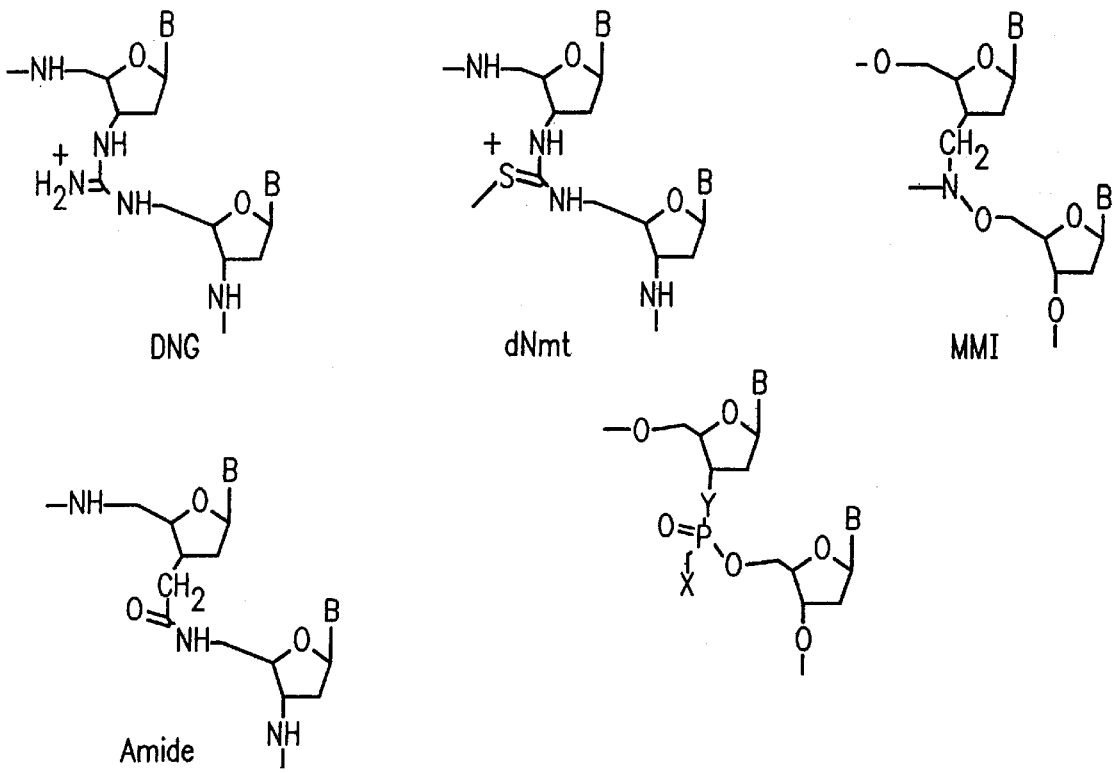
S1. (X = CH$_3$, Y=O)
S2. (X = S$^-$, Y=O)
S3. (X = O$^-$, Y=O)
S4. (X = CH$_2$CH$_2$NH$_3$, Y=O)
S5. (Y = NH, X=O)
S6. (X = NCH$_2$CH$_2$N[CH$_3$]$_2$)
S7. (X = BH$_2$, Y=H)
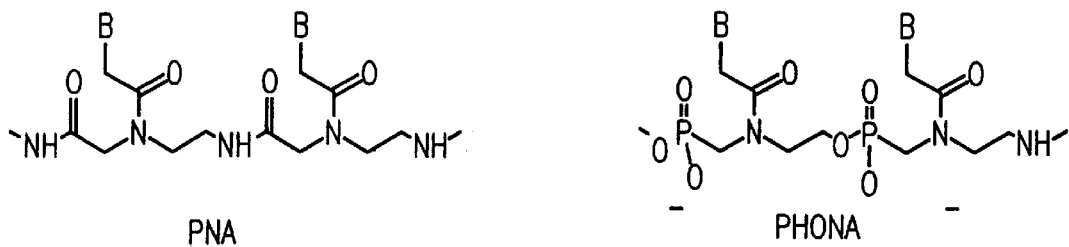
FIG. 1

FIG. 13
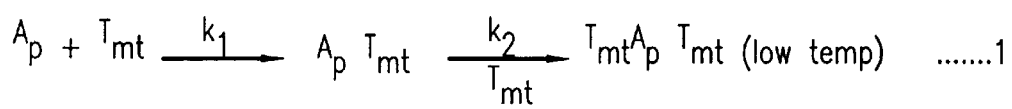
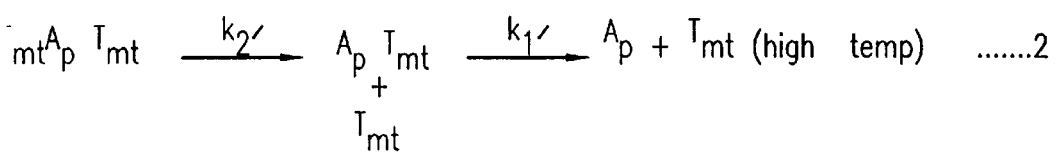
FIG. 14a
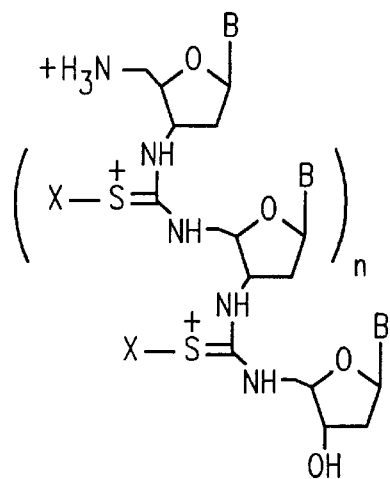
X = alkyl or alkoxy moieties
B = A, G, C, T, U
n = 0–23
FIG. 14b
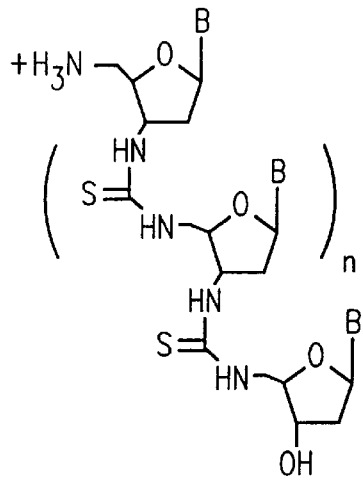
B = A, G, C, T, U
n = 0–23

FIG. 16

1. 5'-AAAAAAAAAAAA-3'
2. 5'-CAAAACAAACAAAA-3'
3. 5'-CCAAACCAAACCAAA-3'
4. 5'-CCCAACCCAACCCAA-3'
5. 5'-CACACACACACACACA-3'

$$D+M \underset{k_{off}}{\overset{k_{on}}{\rightleftharpoons}} Tr$$

$$K_{eq} = \frac{k^T_{on}}{k^T_{off}}$$

NORMAL        SLIDE

FIG. 19 $\quad \dfrac{d[D]}{dt} = k^T_{off}[Tr] - k^T_{on}[D][M]$

FIG. 20 $\quad A = \alpha A_{Tr} + (1-\alpha) A_{D+M}$

FIG. 21
$$k_{on} M_{tot} = k^{ref}_{on} M_{tot} \exp\left\{-\dfrac{E_{on}}{R}\left[\dfrac{1}{T} - \dfrac{1}{T_{ref}}\right]\right\}$$

$$k_{off} = k^{ref}_{on} \exp\left\{-\dfrac{E_{off}}{R}\left[\dfrac{1}{T} - \dfrac{1}{T_{ref}}\right]\right\}$$

FIG. 22

| Oligo | $T_m(°C)$ | $T(°C)$ | $k_{on}*10^4 * M(s^{-1})$ | $k_{off}*10^6 (s^{-1})$ | $k_{eq}*10^{-2}$ | $\Delta G(kcal/mo)$ |
|---|---|---|---|---|---|---|
| 1 | 48.100 | 37 | 1.8411 | 27.730 | 4149.5 | −2.2868 |
| 2 | 39.050 | 37 | 1.3639 | 44.501 | 1915.5 | −1.8123 |
| 3 | 25.690 | 37 | 0.56572 | 224.42 | 157.55 | −0.27902 |
| 4 | 19.940 | 37 | 0.003313 | 4339.5 | 0.047727 | 4.6940 |
| 5 | 16.080 | 37 | 0.001970 | 4458.2 | 0.027619 | 5.0297 |
| 1 | 48.100 | 15 | 30.433 | 4.7530 | 14,700 | −8.1031 |
| 2 | 39.050 | 15 | 152.53 | 2.2050 | 159,000 | −9.4609 |
| 3 | 25.690 | 15 | 21.457 | 6.5170 | 7570.0 | −7.7236 |
| 4 | 19.940 | 15 | 13.003 | 68.070 | 439.36 | −6.0993 |
| 5 | 16.080 | 15 | 9.9700 | 70.480 | 325.35 | −5.9279 |

31, n = 5

```
                              SEQUENCE LISTING

<160> NUMBER OF SEQ ID NOS:  5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Oligo 1

<400> SEQUENCE: 1
aaaaaaaaaa aaaaaaaaaa                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Oligo 2

<400> SEQUENCE: 2 caaacaaaa caaacaaaa                                                       20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Oligo 3

<400> SEQUENCE: 3
ccaaaccaaa ccaaaccaaa                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Oligo 4

<400> SEQUENCE: 4
cccaacccaa cccaacccaa                                                     20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Oligo 5

<400> SEQUENCE: 5
cacacacaca cacacacaca                                                     20
```

DEOXYNUCLEIC ALKYL THIOUREA COMPOUNDS AND USES THEREOF

This application is a continuation in part of U.S. Ser. No. 09/347,443 filed Jul. 2, 1999, pending which claims the priority of provisional applications, U.S. Ser. No. 60/091,481, filed Jul. 2, 1998 and U.S. Ser. No. 60/111,800 filed Dec. 11, 1998.

This invention was made with Government support under Grant No. DK09171, awarded by the National Institutes of Health and Grant No. N000 14–96-1–0123 awarded by the Office of Naval Research. The Government has certain rights in this invention.

FIELD OF THE INVENTION

The present invention relates to oligonucleotide compounds formed by replacing phosphodiester linkages in nucleic acids and more particularly to the synthesis and use of novel deoxynucleic alkyl thiourea (dNXt) compounds.

BACKGROUND OF THE INVENTION

The use of nucleic acid (DNA and RNA) as antisense or antigene drugs, to bind to DNA or RNA of disease-causing proteins to prevent their production, has been hampered by features of the DNA and RNA. For example, the negatively charged phosphodiester linkages of double- and triple-stranded DNA and RNA reside side by side, causing considerable charge—charge electrostatic repulsion, particularly at low (physiological) ionic strength. This feature, as well as the susceptibility of DNA and RNA to damage from nuclease activity, limits the usefulness of RNA and DNA as therapeutic agents. (See, Temsamami and Guinot, *Biotechnol. Appl. Biochem.* 26:65 (1997); Uhlmann and Peyman, *Chem. Rev.* 90:543 (1990); Crooke, *Anticancer Drug Des.* 6:609 (1991); and Crooke, *Ann. Rev. Pharmacol. Toxicol.* 32:329 (1992)).

Among other requirements, successful development of antisense therapeutics presupposes the oligonucleotides a) be stable in vivo, b) have improved permeability and cellular uptake and c) have greater binding affinity with high specificity. (Miller and Ts'o, *Anticancer Drug Des.* 2:117 (1987); Milligan et al., *J Med. Chem.* 36:1923 (1993); and Mesmaeker et al., *Curr. Opin. Struct. Biol.* 343 (1995)).

Suggestions have been made to replace the phosphodiester linkages by other linkages that are either neutral or positively charged and resistant toward nuclease degradation in order to provide more effective antigene/antisense agents. (See, Crooke, (1992), supra, Cook, *In Antisense Research and Applications,* Lebleu (Ed.), CRC Press, Boca Raton, Fla., (1993), p. 149; and Morvan et al., *J. Med. Chem.* 36:280 (1993)). In addition, modification of oligonucleotides so as to enhance cellular uptake has been considered. (Cook et al., supra).

Antisense oligonucleotides having various backbone modifications have been prepared (see Bennett, *Biochemical Pharmacology* 55:9 (1998); Alama et al., *Pharmacological Research* 36:171 (1997); Manoharan, *Designer Antisense oligonucleotides: conjugation chemistry and functionality placement,* CRC Press, Boca Raton, Fla. (1993); and Mesmaeker et al., *Pure Appl. Chem.* 69:43 7 (1997)).

The replacement of the phosphate linkages in DNA and RNA by achiral guanido groups providing a new class of guanidinium (g) linked nucleosides which are designated as DNG has been reported. (Dempcy et al., *Proc. Nati. Acad. Sci. USA* 91:7864 (1994); Dempcy et al., *Proc. Nati. Acad. Sci. USA* 92 (1995); Dempcy et al., *J. Am. Chem. Soc.* 11 7:6140 (1995); and Dempcy et al., *Proc. Natl. A cad. Sci. USA* 93:4326 (1996)).

Some examples of backbone-modified oligonucleotides having different electrostatic atttractions include: peptide (PNA-neutral) (Egholm et al., *J. Am. Chem. Soc.* 114:1895 (1992); and Nielsen and Haaima, *Chem. Soc. Rev.* 73 (1997)); PHONA (Peyman et al., *Angew. Chem., Int. Ed. Engl.* 35:2636 (1996)); methyl phosphonate (DNAmp-neutral) (Stein and Cheng, *Science* 261:1004 (1993); and Tseng and Ts'o, *Antisense Res. Dev.* 5:251 (1995)); phosphorothioate (DNAs-anionic) (Cook, supra; Morvan et al., supra and Marshall and Caruthers, *Science* 259:1564 (1993)); phosphoramidate (Gryaznov and Chen, *J. Am. Chem. Soc.* 116:3143 (1994); amido (Mesmaeker et al., *Angew, Chem. Int. Ed. Engl.* 35:2790 (1996); MMI (Sanghvi et al., *Nucleosides Nucleotides* 16:907 (1997); boronated oligonucleotides (Sood et al., *J. Am. Chem. Soc.* 111:9234 (1989); Sood et al., *J. Am. Chem. Soc.* 223:9000 (1990) and Spielvogel et al., *Pure Appl. Chem.* 63:415 (1991)); ethyl-morpholino and diniethylamino phosphoramidates (Jung et al., *Nucleosides and Nucleotides* 13:1597 (1994) and Letsinger et al., *J. Am. Chem. Soc.* 110:4470 (1988)); aminomethyl phosphonates (Huang et al., *Bioconjugate Chem.* 5:47 (1994); and guanido (Vasseur et al., *J. Am. Chem. Soc.* 114:4006 (1992); Blattler et al., *J. Am. Chem. Soc.* 120:2674 (1991); James et al., *Nucleosides Nucleotides* 16:1821 (1997); Jones et al., *J. Org. Chem.* 58:2983 (1993); Mesmaeker et al., *Acc. Chem. Res.* 28:366 (1995); Rao et al., *Nucleosides Nucleotides* 13:255 (1997); Stirchak and Summerton, *J. Org. Chem.* 52:4202 (1987); and Thibon et al., *J. Org. Chem.* 62:4635 (1997)) (See FIG. 1).

Small positively charged oligonucleotides (DNG) show unprecedented binding to nucleic acids with retention of specificity. (Dempcy et al., *Proc. Natl. Acad. Sci. USA* 92 (1995), supra and Dempcy et al., *J. Am. Chem. Soc.* 117:6140 (1995), supra; and Browne et al., *Proc. Natl. Acad. Sci. USA* 92:7051–7055 (1995)). The nonionic oligonucleotide DNAmp exhibits the ability to be transported into cells by passive diffusion/fluid phase endocytosis and is more resistant to degradation than DNA. (Cook et al., supra). Both DNAmp and DNAs, however have individual limited drawbacks of stereoisomeric complexity (Huang et al., supra), solubility (DNAmp) and toxicity (DNAs). (Morvan et al., supra, and Agrawal et al., *Nucleosides Nucleotides* 16:927–936 (1997)). These findings have led recently to the development of mixed backbone oligonucleotides (MBOs) where the phosphorothioates and methyl phosphonates have been alternated in an oligonucleotide backbone to produce improved antisense properties. (Morvan et al., supra, Agrawal et al., supra and Iyer et al., *Tetrahedron* 52:14419–14436 (1996)).

There remains a need for oligonucleotides that may perform better as antisense or antigene drugs, for example by having stronger affinity for DNA and RNA, as a result of changes in charge characteristics and resistance to nuclease degradation which can form stable constructs.

SUMMARY OF THE INVENTION

Accordingly, the present invention provides novel oligonucleotide compounds having thiourea backbones for use as therapeutic antisense and/or antigene agents. Specifically in the compounds of the invention, negatively charged phosphodiester linkages {—O($PO_2^-$)O—} in nucleic acid (DNA or RNA) are replaced by a novel alkyl thiourea backbone having alkyl or alkoxy linkages to form novel compounds designated as dNXtsIn one embodiment, the phosphodiester linkages are replaced by a methylthiourea {—NHC(=SMe$^+$)NH—} backbone to form dNmt. The backbone is positively charged, achiral, stable and can be readily synthesized.

The Thymidyl dNmt compounds of the invention are the first example of a positively charged polynucleotide backbone incorporating a methyl isothiouronium salt.

The dNXt compounds have higher affinity for DNA and RNA then, DNA has for RNA, or vice versa. Because of the alkyl group present in these compounds, properties such as hydrophobicity and cellular uptake of these compounds, may be readily modified to form improved compounds for use as therapeutic agents.

BRIEF DESCRIPTION OF THE DRAWINGS

(FIG. 10a) Job Plot of poly(rA) ($5.3\times10^{-5}$ M) and 11d in 15 mM $K_2HPO_4$, 15 M KCl, pH 7.5 at 60° C., carried out at 284, 260 and 202 nm; (FIG. 10b) Job Plot of poly(rA) ($5.3\times10^{-5}$ M) and 11d in 15 mM $K_2HPO_4$, 0.15 M KCl, pH 7.5 at 15° C., carried out at 284, 260 and 202 mn.

FIG. 13. Annealing process in the formation of hybrid structures as described in Example V, infra.

FIG. 14(a–b). Structure of the dNXt compounds of the invention (FIG. 14a are positively charged deoxynucleic alkyl or alkoxy thiourea compounds; FIG. 14b are neutral deoxynucleic thiourea compounds.)

FIG. 16. List of oligomers (1–5) SEQ ID NO. 1; SEQ ID NO. 2; SEQ ID NO. 3; SEQ ID NO. 4; SEQ ID NO. 5.

FIG. 19. Expression of kinetic equations for the reactants and products.

FIG. 20. Equation for monitored absorbance.

FIG. 21. Arrhenius Equations for $k_{on}$ and $k_{off}$

FIG. 22. Table of Melting points ($T_m$), rates of association ($k_{on}$) and dissociation ($k_{off}$) of DNmt triplexes with d(pA$_x$C$_y$) oligomers 1–5, SEQ ID NO. 1; SEQ ID NO. 2; SEQ ID NO. 3; SEQ ID NO. 4; SEQ ID NO. 5 and free energies of formation of d(pAxCy)·(DNmt)$_2$ triplexes at 15° C. and 37° C. The data shown are average of the values in concentration range (10 $\mu$M to 40 $\mu$M) at 0.10M KCl. (Margin of errors: $k_{on}\cdot M_{tot}\pm0.24\times10^{-4}$ s$^{-1}$; $k_{off}\pm0.24\times10^{-6}$ s$^{-1}$, $\Delta G=\pm0.2$ kcal/mol, $T_m\pm1$° C.)

DETAILED DESCRIPTION OF THE INVENTION

The present invention provides novel oligonucleotides designated as dNXt compounds, obtained from modifications of nucleic acid having the negatively charged phosphodiester linkages {—O($PO_2^-$)O—} replaced with an alkyl or alkoxy thiourea backbone (FIG. 14). In one embodiment, the new backbone is a polycationic deoxyribonucleic methylthiourea abbreviated as dNmt {—NHC(=SMe$^+$)NH—}.

Preparation of the New Compounds of the Invention

Figures 1, 2:
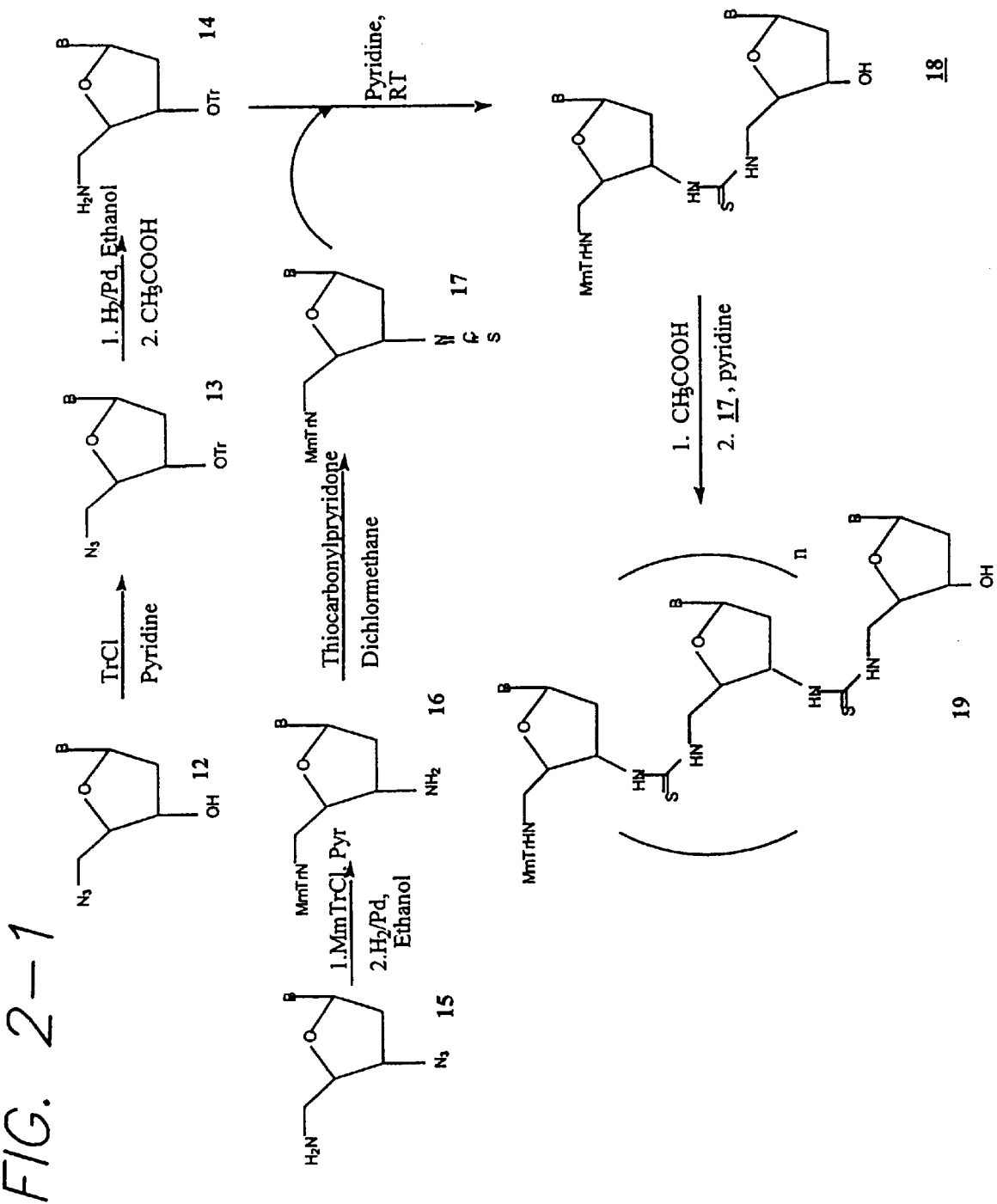
FIG. 1. Structures of backbone-modified oligonucleotides.
FIG. 2. Synthetic scheme for the dNXt compounds of the invention.
Figure 2:
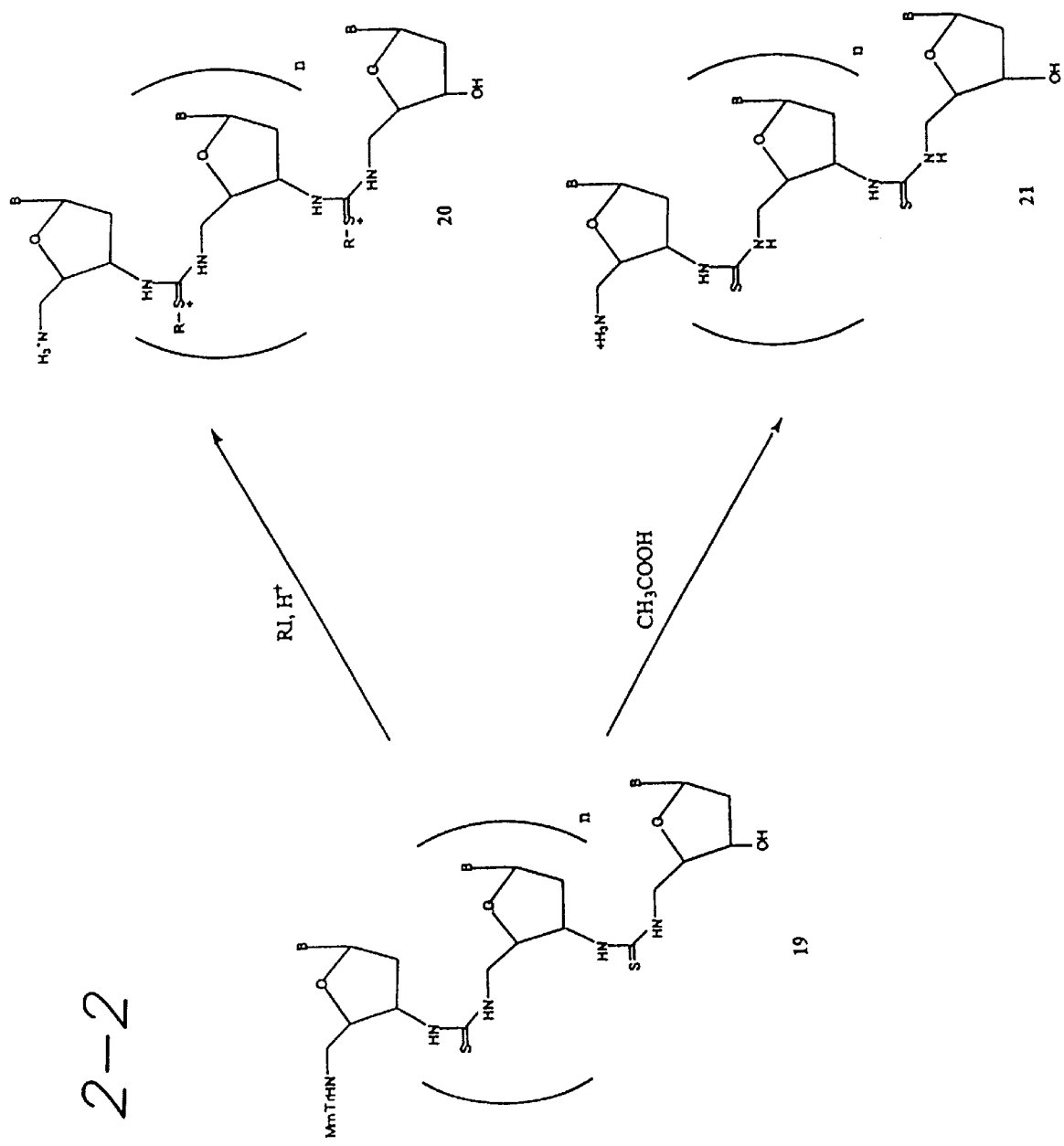

The deoxynucleic alkyl or alkoxy thiourea compounds of the invention are prepared as shown in FIG. 2. Briefly, 5'-amino-5'-deoxy-B (where B=thymidine (T); adenosine (A); guanine (G); cytosine (C); or uracil (U), are prepared by starting with 5'-azido-5'-deoxy-B (12). To a solution of compound 12 in pyridine is added (dimethylamino)pyridine (DMAP) followed by triphenylmethyl chloride (TrCl). The resulting solution is stirred at 100° C., until the reaction is completed. The solvent is rotovaporated, the concentrate chromatographed, and the protected compound is isolated. The protected compound is hydrogenated to provide 5'-amino-3'—O-trityl-5'-deoxy-B (13). Post-hydrogenation, 5'-amino-3'—O-trityl-5'-deoxy-B is deprotected to provide 5'-amino-5'-deoxy-B (14).

3'-isothiocyanate-5'—O-MmTr-3'-deoxy-B (17) is prepared from protection of 5'-amino- 3'-azido-3',5'-dideoxy-B (15) with monomethoxytritryl chloride (MmTrCl) followed by hydrogenation of the azido group. The reaction of the resulting 3'-amino-5'—N-Mntrityl-3',5'-deoxy-B (16) with excess thiopyridone at room temperature followed by flash chromatography, provides 3'-isothiocyanate-5'—O-MmTr-3'-deoxy-B.

The coupling reaction of compounds 14 and 17 is conducted as follows: to a solution of 3'-isothiocyanate-5'—O-MmTr-3'-deoxy-B (17) in anhydrous pyridine is added 5'-amino-5'-deoxy-B (14) followed by DMAP. The resulting solution is stirred at room temperature. After workup, the product is isolated, deprotected, and the coupling step is reiterated until a length of desired sequence is obtained. At this point, the polymeric compound (19) can be converted by alkylation of the thiourea linkages via reaction of 19 with excess alkyl or alkoxy halide (FIG. 2 cont.). Deprotection of alkylated polymers with acetic acid, is followed by purification and isolation to yield deoxynucleic alkyl/alkoxy thiourea compounds (20) of the invention. The sample may be further purified by HPLC. Alternatively, compound 19 can be subjected to deprotection with acetic acid, followed by purification and isolation to yield deoxynucleic thiourea compounds (21).

In addition, charged functional groups may be attached to the 5'-amine of DNT to provide increased solubility.

Preparation of Compounds via Solid Phase Synthesis

Figure 36:
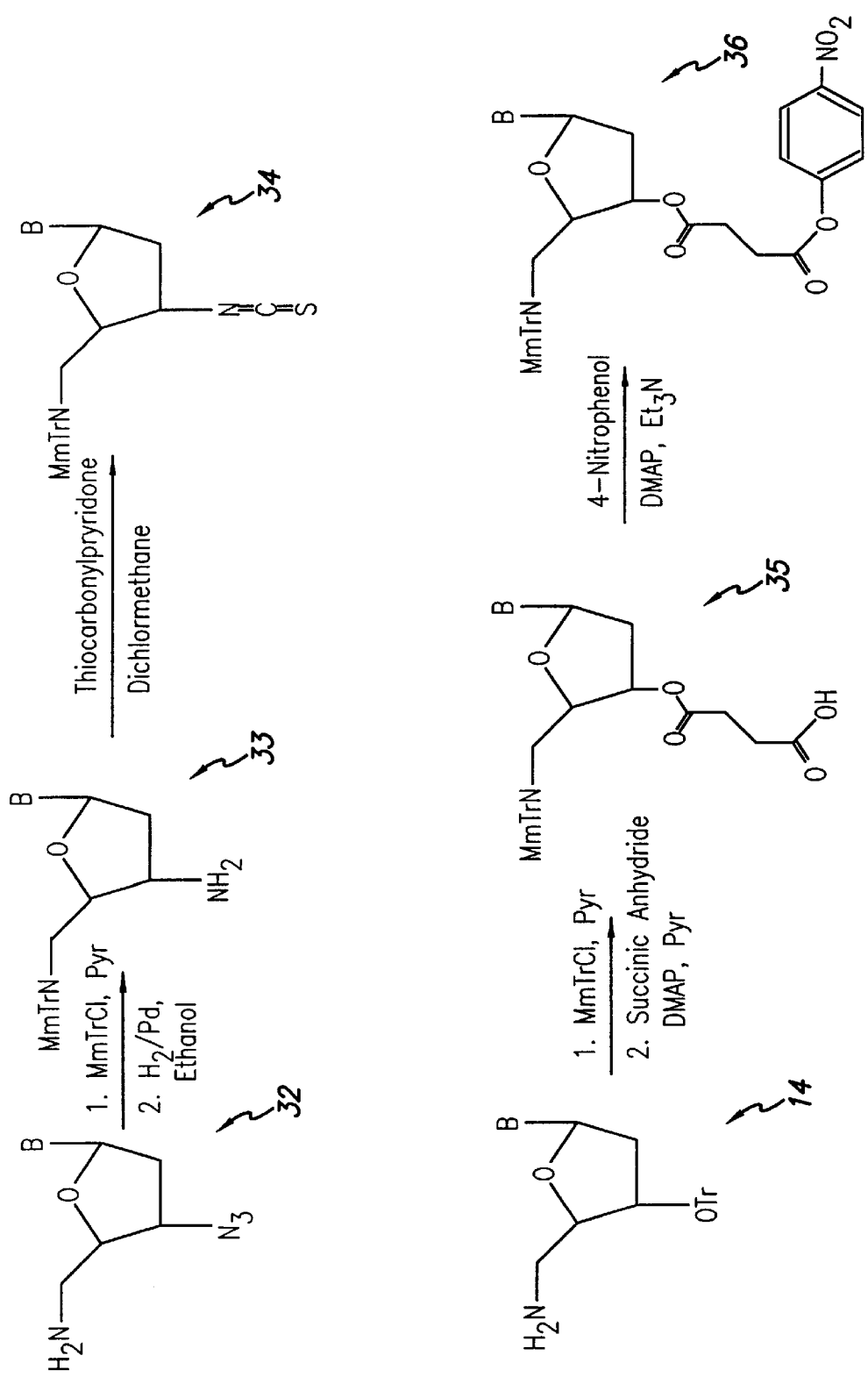
FIG. 36. General Synthesis of Monomer for Solid Phase Synthesis

The sequences can also be synthesized by solid phase synthesis as described in Example VIII in which a stepwise construction of DNmt strands on solid support is described. The deoxynucleic alkyl or alkoxy thioureas of the invention can also be prepared as shown in FIG. 36. Briefly, for solid phase synthesis (SPS) 3'-isothiocyanate-5'—O-MrmTr-3'-deoxy-B (34) is prepared from protection of 5'-amino-3'-azido-3',5'-dideoxy-B (32) with monomethoxytrityl chloride (MmTrCl) followed by hydrogenation of the azido group. The reaction of the resulting 3'-amino-5'—N-Mmtrityl-3', 5'-deoxy-B (33) with excess thiopyridone at room temperature followed by flash chromatography to produce 3'-isothiocyanate-5'—O-MmTr-3'-deoxy-B. (FIG. 36)

ControlPore Glass (CPG) resin (Sigma; St. Louis, Mo.) with long chain alkylamine was chosen as a convenient commercially available support with a linker that was cleavable using a mild base. The synthesis was designed to be compatible with standard DNA synthesis techniques to facilitate future synthesis of DNmt-DNA conjugates. (Barawkar, D. A. & Bruice, T. C. (1998) *Proceedings of the National Academy of Sciences, USA* 95, 1104–11052). Analogous to DNA synthesis, 3'—OH of compound 14 was converted to the activated nitrophenyl ester 36, which was loaded as the first base on the resin. (Atkinson, T. & Smith, M. (1990) in *Solid-Phase Synthesis of Oligodeoxyribonucleotides by the Phosphitetriester method*, ed. Gait, M. J. (Oxford University Press, New York), pp. 35–81)

Figure 37A:
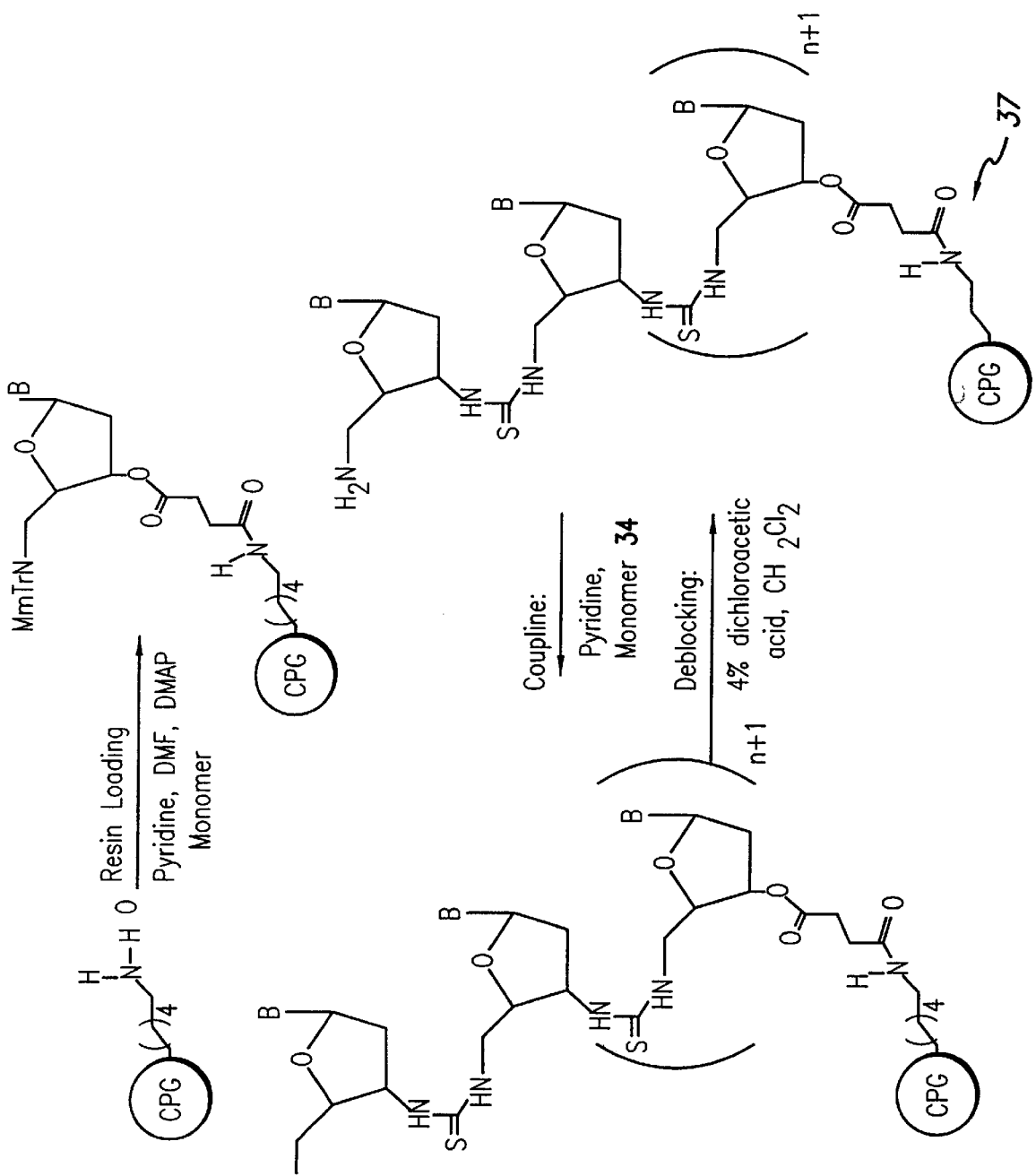
FIG. 37a. Solid Phase Synthesis of DNX

The coupling reaction involved the addition of compound 34 to a 5'-amino-B residue on the resin. In a typical synthesis, 36 mg of resin was placed in 0.5 ml Pyridine in a 3 ml reaction vial. Stock solutions of the isothiocyanate, compound 34, (30 mM, 1.0 ml), DMAP (12 mM ) in pyridine were added and the vial was agitated for 4 hr. The addition step was repeated twice to insure a complete reaction and then the resin was washed with copious amounts of pyridine, methanol and ether. The resulting 5'-MmTr protected oligomer was deblocked with 4% dichloroacetic acid in $CH_2Cl_2$ and the cycle repeated (FIG. 37A). The addition/deblocking cycle was repeated as many times as needed to produce the desired oligomer unit, DNX.

Figure 37B:
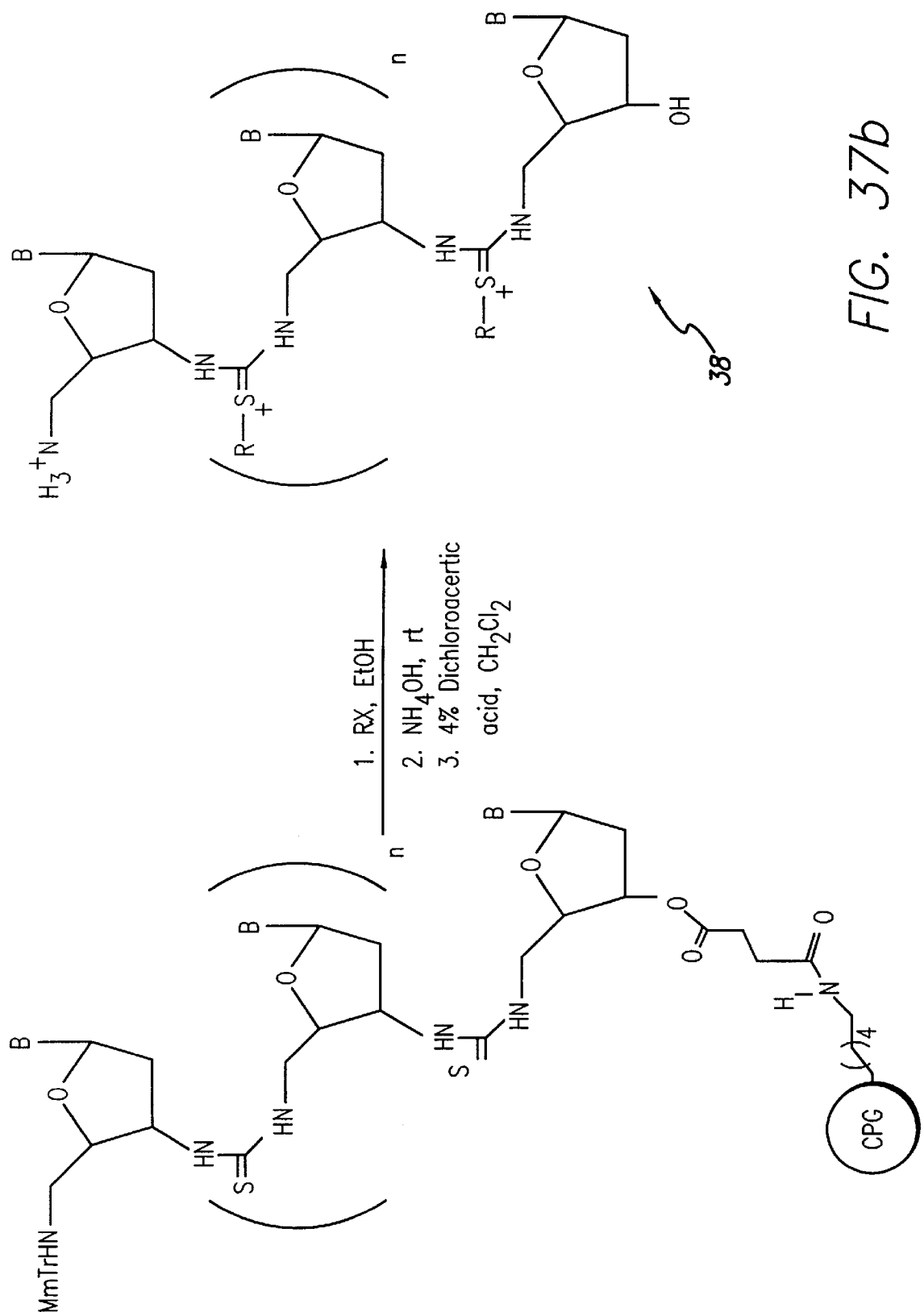
FIG. 37b. Solid Phase Synthesis of DNXt

The thiourea oligomer was alkylated with 2 ml alkyl iodide for 4 hr. The 5'-MrTr group was removed in 4% DCA and the resin washed with methanol, ether. The product was cleaved from the resin by treatment with $NH_4OH$ at room temperature. The oligomer can be cleaved from the resin before alkylation to give the corresponding thiourea compound 37 as well (DNX). Alkylation of the tritylated thiourea can be performed in solution as well as on the solid phase. The deprotected DNXt oligomer compound 38 can be purified on a preparative Alltech WCX cation exchange column employing 1.50 M ammonium acetate buffer, pH 6.0, as the mobile phase to give the pure oligomer (FIG. 37B).

Uses of The Compounds of the Invention

The dNXt compounds of the invention can be used as intact oligomers or can be incorporated with other nucleotide linkages as mixed backbone oligonucleotides to inhibit production of proteins associated with genetic diseases. Procedures for using antisense compounds as therapeutic agents are known. In particular, the dNXt compounds can be used for antiviral therapy, for example to treat human immunodeficiency virus, human-cytomegalovirus, influenza, herpes and human pappilovirus infections. The compounds may also be used as chemotherapeutic agents to control cancer-cell growth by specific targeting of cancer-specific genes. Other uses include use as therapeutic antisense agents to treat cardiovascular, inflammatory and neurocellular diseases. The stable backbone of the chimera dNXt compounds permits their use as artificial ribozymes in combination with RNA.

The dNXt compounds of the invention can be used as antisense agent in antisense therapy. As used herein, "antisense" therapy refers to administration or in situ generation of nucleotide (e.g. dNXt) probes or their derivatives which specifically hybridize (e.g. binds) under cellular conditions, with a target cellular mRNA and/or genomic DNA so as to inhibit expression of the corresponding target protein, e.g. by inhibiting transcription and/or translation. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide (e.g., dNXt) sequences.

A dNXt construct of the present invention can be delivered, for example, as an expression plasmid which, when transcribed in the cell, produces RNA which is complementary to at least a unique portion of the cellular mRNA which encodes a target protein. Alternatively, the dNXt construct can be a nucleotide probe which is generated ex vivo and which, when introduced into the cell causes inhibition of expression by hybridizing with the mRNA and/or genomic sequences of a target gene. Such probes are preferably modified so they are resistant to endogenous nucleases, e.g. exonucleases and/or endonucleases, and is therefore stable in vivo.

Accordingly, the dNXt constructs of the invention are useful in therapeutic, diagnostic, and research contexts. In therapeutic applications, the oligomers are utilized in a manner appropriate for antisense therapy in general. For such therapy, the dNXt constructs of the invention can be formulated for a variety of loads of admninistration, including systemic, topical or localized administration. Techniques and formulations generally may be found in Remmington's Pharmaceutical Sciences, Meade Publishing Co., Easton, Pa. For systemic administration, injection can be effected, including intramuscular, intravenous, intraperitoneal, and subcutaneous for injection, the dNXt constructs of the invention can be formulated in liquid solutions, preferably in physiologically compatible buffers such as Hank's solution or Ringer's solution. In addition, the dNXT constructs may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. Transmucosal administration may be through nasal sprays or using suppositories. For oral administration, the dNXt constructs can be formulated into conventional oral administration forms such as capsules, tablets, and tonics. For topical administration, the oligomers of the invention can be formulated into ointments, salves, gels, or creams as generally known in the art.

In addition to use in therapy, the dNXt compounds of the invention may be used as diagnostic reagents to detect the presence or absence of the target DNA or RNA sequences to which they specifically bind.

Likewise, the dNXt constructs of the present invention, by antagonizing the normal biological activity of a target protein, can be used in the manipulation of tissue, e.g. tissue differentiation, both in vivo and in ex vivo tissue cultures.

The following Examples are presented to demonstrate the methods and compounds of the present invention and to assist one of ordinary skill in making and using the same. The Examples are not intended in any way to otherwise limit the scope of the disclosure of the protection granted by Letters Patent granted hereon.

EXAMPLE I

This Example describes the synthesis of thymidyl methylthioureas (T-DNmts)

Reagents

The concentrations of nucleotide solutions were determined using the extinction coefficients (per mol of nucleotide) calculated according to the nearest neighboring effects. (Blasko et al., *J. Am. Chem. Soc.*, 1996, 118:7892) For $d(Tmt)_5$ $\epsilon_{268}$=8700 $M^{-1}$ $cm^{-1}$ was used. All experiments were conducted in either a) 0.015 M phosphate buffer, pH 7–7.5 or b) 0.008 M phosphate buffer at pH 6.85 and the ionic strength, $\mu$, was adjusted with KCl and are presented with the corresponding concentration of KCl. The concentrations of nucleosides, expressed in M/base, were $2.1 \times 10^{-5}$–$6.3 \times 10^{-5}$ M and the ionic strength $\mu$=0.06–0.6. The concentration is referred to the limiting component forming the triplex (e.g., a concentration of $2.1 \times 10^{-5}$ M/base in the reaction of A+2T means [A]=$2.1 \times 10^{-5}$ M/base and [T]=$4.2 \times 10^{-5}$ M/base). All stock solutions were kept at 4° C. between experiments.

Sample Preparation

Five magnetically stirred screw-cap cuvettes of 1-cm path length were used for data collection: four with samples to be measured and one for the temperature monitoring. The measurement chamber was purged continuously with dry nitrogen to prevent condensation of water vapor at lower temperatures. Annealing and melting were followed spectrophotometrically at the given wavelength.

UV Spectroscopy and Data Collection. A Cary 1E UV/vis spectrophotometer equipped with temperature programming and regulation and a thermal melting software package were used for data collection at $\lambda$=260 nm. Spectrophotometer stability and λ alignment were checked prior to initiation of each melting point experiment. For the $T_m$ determinations hypochromicity was used. Data were recorded every 1.0 deg. The samples were heated from 25–95° C. at 5 deg/min (Scheme 1), the annealing (95–10° C.) and the melting (10–95° C.) were conducted at 0.13 deg/min and the samples were brought back to 25° C. at a rate of 5 deg/min. The reaction solutions were equilibrated for 15 min at the highest and lowest temperatures. (Blasko et al., *Biochem.* 36:7821–7831 (1997)).

Scheme 1

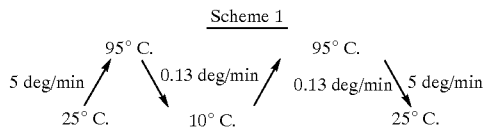

Synthesis

All reactions were performed under a positive atmosphere of dry nitrogen. $^1$H NMR spectra were obtained at 400 MHz unless indicated otherwise and $^{13}$C NMR spectra at 125 MHz; chemical shifts (δ) are relative to internal TMS, coupling constants (J) are in Hertz. Splitting patterns are designated singlet (s), doublet (d), triplet (t), quartet (q), multiplet (m), or broad (b). IR spectra were taken in KBr pellet using Perkin Elmer 1300 spectrophotometer. TLC was carried out on silica gel (kieselgel 60 $F_{254}$), 0.25 mm coated commercial silica plates and visualized by UV-light or p-anisaldehyde in ethanol/sulfuric acid. Flash column chromatography employed E. Merck silica gel (kieselgel 60, 200–400 mesh) as the stationary phase. Individual mobile phase systems are described in the experimental section. TtT refers to thymidyl dinucleotide with a thiourea linkage, TmtT refers to a thymidyl dinucleotide with a methylated thiourea linkage.

Figure 11:
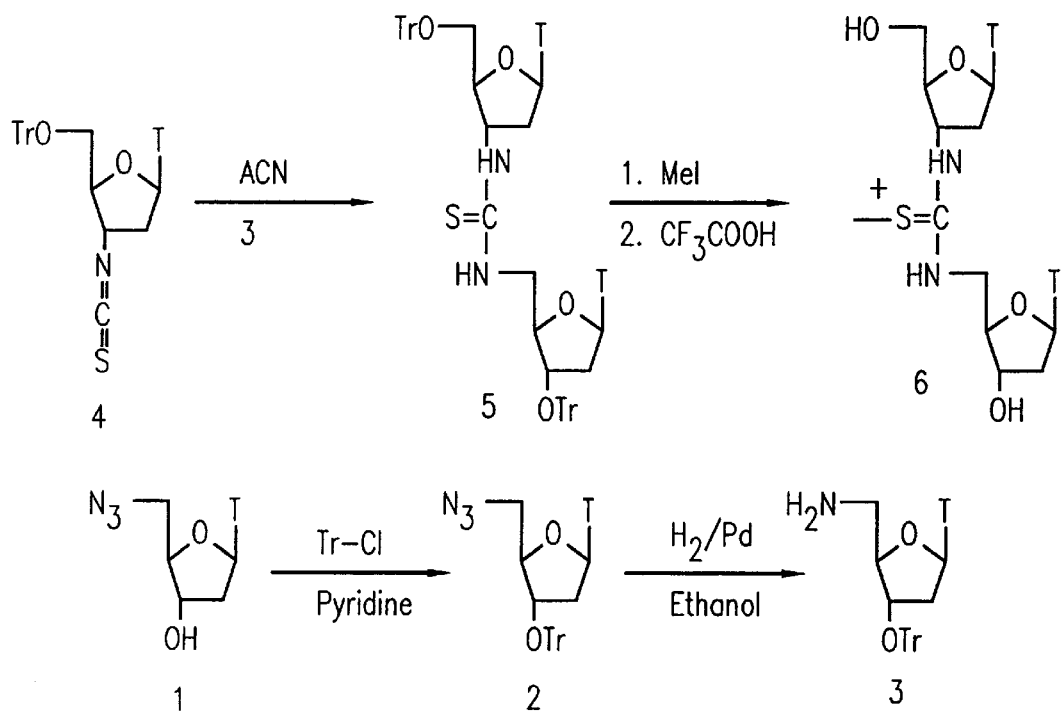
FIG. 11. Synthesis of compound 6, dimeric thymidyl methylthiourea.

FIG. 11 refers to the synthesis of compound 6, dimeric thymidyl methylthiourea, described below.

Synthesis of 5'-azido-3'—O-trityl-5'-deoxythymidine (Compound 2)

To a solution of 4 g (14.96 mmole) of 5'-azido-deoxythymidine (1) in 100 ml of Pyridine was added 50 mg (0.4098 mmole) of dimethylaminopyridine followed by 10 g (0.035 mole) of triphenylmethylchloride. The resulting solution was stirred at 100° C. for 48 hr. TLC analysis in EtOAc shows complete disappearance of the starting material ($R_f$= 0.1). The product has a $R_f$ value of 0.4. The solvent was rotovaporated and the resulting concentrate chromatographed in EtOAC Hexanes (1:1) followed by elution with 100% EtOAc to give 7 g of the product (91.9%). $^1$H NMR-400 MHz (CDCl$_3$): δ 8.651 (1H, s, NH), 7.90–7.25 (15H, m, trityl-H), 7.173 91H, d, J=1.2 Hz, 6—H), 6.33 (1H, q, J=5.6 Hz, 3.6 Hz, 1'—H), 4.226 (1H, h, J=5.6 Hz, 3.6 Hz, 3.2 Hz, 3'—H), 3.910 (1H, q, J=3.2 Hz, 2.8 Hz, 4'—H), 3.329 (1H, dd, J=9.6 Hz, 2.8 Hz, 5'—H), 2.740 (1H, dd, J=9.6 Hz, 3.2 Hz, 5'—H), 1.990 (1H, m, 2'—H), 1.860 (3H, d, J=1.2 Hz, Me), 1.699 (2H, m, 2'—H). δ $^{13}$C (CDCl3–125 MHz): 163.209, 150.055, 146.777, 134.474, 128. 885, 128.048, 127. 479, 111.245, 87.933, 84.549, 52.134, 39.079, 12.520. IR (KBr pellet): 3051 (Aromatic C—H), 2928 (Aliphatic C—H), 2099 (N=N=N), 1686 (C=O), 1481, 1442, 1274, 1029. m/z: FAB -510 (M+H)$^+$, Analysis: Calculated (C-71.4%, H-6.0%), Found (C-71.56%, H-6.05%).

Synthesis of 5'-amino-3'—O-trityl-5'-deoxythymidine (Compound 3)

To a solution of 1.5 g (2.94 inmole) of 5'-azido-3'—O-trityl-5'-deoxythymidine (2) in 100 ml of ethanol was added 50 mg of palladium on carbon catalyst (10%). The resulting solution was hydrogenated at 45 psi for 1 hr. TLC analysis in EtOAc shows complete disappearance of the starting material ($R_f$=0.4). The product has a $R_f$ value of 0.1. The solution was filtered over Celite and the solvent evaporated under pressure. Chromatography in 15% MeOH: 85% EtOAc gave 1.1 g of the pure product (77.4%). $^1$H NMR-400 MHz (d$_6$-DMSO): (7.646 (1H, d, J=1.2 Hz, NH), 7.446–7.264 (15H, m, trityl-H), 6.121 (1H, q, J=5.2 Hz, 4.0 Hz, 1'—H), 4.20 (1H, d, J=5.6 Hz, 2'—H), 3.782 (1H, p, J=5.2 Hz, 3.2 Hz, 4'—H), 3.347 (2H, br, NH$_2$),2.455 (1H, dd, J=4.8 Hz, 5.2 Hz, 5'—H), 2.359 (1H, dd, J=4.8 Hz, 5.2 Hz, 5'—H), 1.719 (3H, d, J=1.2 Hz, Me), 1.410 (1H, d, J=5.6 Hz, 2'—H), 1.380 (1H, d, J=6 Hz, 2'—H). δ $^{13}$C (d$_6$-DMSO-125 MHz): 163.573, 150.419, 144.198, 136.111, 128.510, 128.047, 127.266, 109.620, 87.058, 86.527, 83.561, 74.882, 43.179, 37.520, 12.083. IR (KBr pellet): 3388, 3310 (N—H), 3054 (Aromatic C—H), 2948, 2917 (Aliphatic C—H), 1655 (C=O), 1447, 1273, 1023. m/z: 484 (M+H)$^+$, HRMS (FAB): 484.22312, Calculated for $C_{29}H_{30}N_3O_4$: 484.22363.

Synthesis of 3'-isothiocyanate-5'—O-trityl-3'-deoxythymidine (Compound 4)

To a solution of 300 mg (0.6192 mmole) of 3'-amino-5'—O-trityl-deoxythymidine in 20 ml of dichloromethane was added 150 mg (0.64 nunole) of thiocarbonylpyridone and the resulting solution stirred at room temperature for 6 hr. TLC analysis in 80% EtOAc: 20% Hexanes shows complete disappearance of the amine ($R_f$=0.1). The product has a $R_f$ value of 0.8 and pyridone of 0.45. The solvent was rotovaporated and the product chromatographed in EtOAC : Hexanes (1:1) to give 290 mg of the product (88%). $^1$H NMR-200 MHz (CDCl$_3$): δ 9.636 (1H, s, NH), 7.493 (1H, s, 6—H), 7.493–7.279 (15H, m, trityl-H), 6.2899 (1H, t, J=6.18 Hz, 1'—H), 4.606 (1H, q, J=7.32 Hz, 1.82 Hz, 3'—H), 4.139 (1H, q, J=7.32 Hz, 5.12 Hz, 4'—H), 3.60 (1H, dd, J=8.18 Hz, 5.12 Hz, 5'—H), 2.858 (2H, m, 2'—H), 1.5612 (3H, s, Me). δ $^{13}$C (d$_6$-DMSO+CDCl$_3$-75 MHz): 149.794, 146.854, 142.249, 134.811, 127.558, 127.185, 126.628, 125.812, 109.767, 84.4025, 83.395, 80.2512, 54.410, 11.657. IR (KBr pellet): 3190, 3050 (Aromatic C—H), 2083, 2047 (N=C=S), 1689 (C=O), 1458, 1273, 1099, 1063. m/z: 526.2 (M+H)$^+$, Analysis: Calculated (C-68.6%, H-5.2%), Found (C-68.5%, H-5.3%)

Synthesis of 5'—O-trityl-TtT-3'—O-trityl (Compound 5)

To a solution of 250 mg (0.474 mmole) of 3'-isothiocyanate-5'—O-trityl-3'-deoxythymidine (4) in 20 ml of anhydrous acetonitrile was added 240 mg (0.496 mmole) of 5'-amino-3'—O-trityl-5'-deoxythymidine (3) followed by 5 mg of dimethylaminopyridine and the resulting solution stirred at room temperature. A white precipitate begins to appear after 20 minutes. The reaction is stirred for 2 hr. and the solution then cooled to 0° C. for 30 minutes. The white precipitate is then collected by filtration, washed with cold ether and dried to give 460 mg (96.2%) of analytically pure product. TLC analysis in EtOAc shows complete disappearance of the amine ($R_f$=0.1). The product has a $R_f$ value of 0.4 and the isothiocyanate has a $R_f$ value of 0.85. $^1$H NMR-400 MHz (CDCl$_3$): δ 10.135 (1H, s, NH), 10.229 (1H, s, NH), 10.135 (1H, s, NH), 9.990 (1H, s, NH), 7.606 (1H, s 6—H), 7.450–7.233 (30H, m, trityl-H), 6.932 (1H, s, 6—H), 6.537 (1H, t, 3 6.8 Hz, 1'—H), 5.989 (1H, t, 3 6.8 Hz, 1 '—H), 5.237 (1H, b, 3'—H), 4.287 (1H, b, 3'—H), 4.146 (1H, m, 4'—H), 3.790 (1H, m, 4'—H), 3.65 (2H, d, J=9.2 Hz, 2'—H), 3.345 (2H, d, 3 9.2 Hz, 5'—H), 2.489–2.334 (4H, m, 2'—H), 1.804 (3H, s, Me), 1.392 (3H, s, Me). δ $^{13}$C (CDCl$_3$-125 MHz): 173.526, 164.332, 164.036, 151.064, 150.926, 150.608, 146.785, 143.758, 143.364, 128.639, 128.101, 127.941, 127.828, 127.433, 127.213, 127.152, 111.745, 111.199, 87.910, 87.910, 87.478, 85.680, 84.360, 84.360, 75.097, 64.803, 55.556, 36.750, 12.240, 11.640. IR (KBr pellet): 3395,3451 (N—H), 3361, 3317 (N—H), 3050 (Aromatic C—H), 1692 (C=O), 1535, 1447, 1267, 1053. m/z: 1009.18 (M+H)$^+$. Analysis-:Calculated (C-70.2%, H-5.6%), Found (C-70.3%, H-5.55%).

Synthesis of 5'—OH-TmTT-3'—OH (Compound 6)

To a solution of 30 mg (0.029 mmole) of 5'—O-trityl-TtT-3'—O-trityl (5) in 20 ml of ethanol was added 10 ml of methyl iodide and the resulting solution stiffed at room temperature for 2 hr. followed by heating to 35° C. for 20 minutes. TLC analysis in EtOAc shows complete disappearance of the starting material ($R_f$=0.6). The product has a $R_f$ value of 0.5. The solvents were then evaporated under pressure and the residue washed with hexanes and dried to give 29 mg of a 5'—O-trityl-TmtT-3'—O-trityl as a yellowish solid (97.6%). m/z: 1024 (M+H)$^+$, ERMS (FAB): 1023.4103.

To a solution of 20 mg (0.0195 mmole) of 5'—O-trityl-Tmt-T-3'—O-trityl in 10 ml of dichloromethane was added 10 ml of trifluoroacetic acid. The resulting solution was stirred at room temperature for 1 hr. The solvents were then evaporated under pressure and to the resulting gel was added 100 ml of diethyl ether. The white precipitate obtained was filtered off and washed with ether and dichloromethane to give 9 mg of dry product (85.7%). $^1$H NMR-400 MHz (d$_6$-DMSO): δ 11.56 (2H, NH), 9.677 (1H, br, NH), 9.33 (1H, d, J 6.8 Hz), 9.210 (1H, br, NH), 7.914 (1H, s, 6—H), 7.688 (1H, s, 6—H), 6.452 (1H, t, J 6.8 Hz, 1'—H), 6.336 (1H, t, J=6.8 Hz, 1'—H), 5.661 (2H, br, OH), 4.681 (1H, br, 3'—H), 4.494 (1H, m, 3'—H), 4.292–4.054 (2H, m, 4'—H), 3.989–3.60 (4H, m, 5'—H), 2.904 (3H, s, Me), 2.715 (2H, m, 2'—H), 2.34 (2H, m, 2'—H), 2.00 (3H, s, Me). 6 8$^3$C (d$_6$-DMSO-125 MHz): 168.101, 163.618, 163.375, 150.319, 150.266, 136.649, 136.140, 109.816, 109.490, 83.810, 83.408, 82.915, 70.398, 60.134, 54.717, 53.837, 46.752, 44.855, 37.640, 36.525, 14.844, 14.184. IR (KBr pellet): 3465 (O—H), 3385, 3451 (N—H), 3044 (Aromatic C—H), 2959 (Aliphatic C—H), 1682 (C=O), 1545, 1457, 1267, 1063. m/z: 539 (M+H)$^+$, HRMS (FAB): 539.1933, Calculated for C$_{22}$H$_{31}$N$_6$O$_8$S: 539.19240.

Results

Initial studies were focused on attempts to synthesize dimeric thymidyl methyl urea (compound 6) (FIG. 11). Coupling conditions for the formation of thiourea linkage were optimized using compounds 3 and 4. The isothiocyanate 4 was easily synthesized by reaction of the corresponding 3'-amino-5'—O-trityl-dideoxythymidine with thiopyridone at room temperature. Compound 3 on the other hand was synthesized in a two-step process from 5'-azido thymidine. Protection of the 3'-hydroxyl with triphenylmethyl chloride in pyridine followed by reduction of the azide gave compound 3 in excellent yields. Protection of 3'-hydroxyl with base labile groups (phenoxyacetyl) led mostly to the rearrangement involving nucleophilic attack by the 5'-amine.

The reaction of compounds 3 with 4 was followed under varying temperatures and solvents to optimize coupling reaction conditions. Heating the isothiocyanates to speed up the reaction led to slight decomposition of the isothiocyanate (reaction with traces of moisture). The reaction proceeds to completion at room temperature in a few hours with pyridine and acetonitrile as the solvents of choice. Thiourea 5 was methylated with excess methyl iodide and the product detritylated with TFA to give DNmt dimer 6. Compound 6 was found to be analytically pure by HPLC, NMR and MS. The 1H-NMR (1D and 2D) spectra of compound 6 showed the resolution of similar protons in the two sugar rings. The methyl peak of the thiourea is considerably deshielded and appears at 3 ppm. While the assignments can be easily made in a dimer, longer sequences show much greater overlap and the compounds were then characterized by a combination of NMR, MS, IR, elemental analysis and in case of methylated thioureas-cation exchange HPLC, MS and UV.

EXAMPLE II

Synthesis of T$_5$-mt (Compound 11d)

Figure 12:
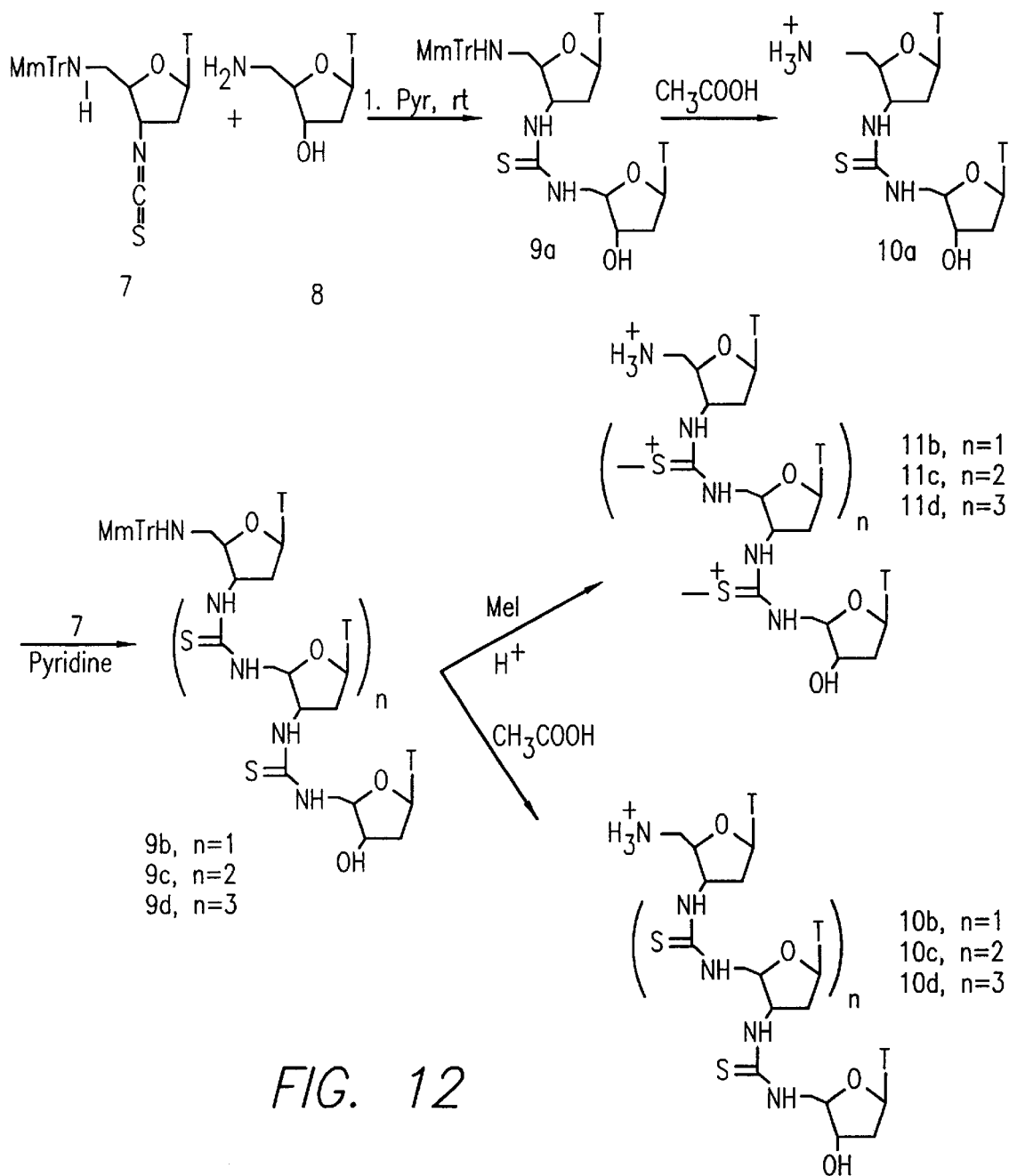
FIG. 12. synthesis of polymeric dNmt (compounds 9a–9d, 10a–10d and 11b–11d).

FIG. 12 illustrates the synthesis of polymeric dNmt (compounds 9a–9d; 10a–10d and 11b–11d), described below.

Synthesis of 5'—N-MmTr-TtT-3'—OH (Compound 9a)

To a solution of 100 mg (0.180 mmole) of 3'-isothiocyanate-5'—N-MmTr-3', 5'-dideoxythymidine (7) in 10 ml of anhydrous pyridine was added 100 mg (0.414 mmole) of 5'-amino-5'-deoxythymidine (8) followed by 5 mg of dimethylaminopyridine and the resulting solution stirred at room temperature for 2 hr. Pyridine is evaporated under pressure and 20 ml of water is added to the residue to precipitate the product. The product is extracted into 2×30 ml of chloroform, washed successively with water to remove the excess amine. The organic extracts are dried over sodium sulfate and evaporated to give 130 mg of a dry product (90.9%). $^1$H NMR-400 MHz (d$_6$-DMSO): δ 10.596 (1H, s, NH), 10.550 (1H, s, NH), 7.735 (2H, NH), 7.120 (4H, d J=7.6 Hz, trityl-H), 7.01 (2H, d, J=9.2 Hz, trityl-H), 6.89 (4H, t, J=7.6 Hz, trityl-H), 6.819 (2H, m, trityl-H), 6.437 (2H, d, J=9.2 Hz, trityl-H), 5.88 (2H, m, 1'—H), 4.734 (2H, d, J=4.4 Hz), 3.897 (1H, m), 3.560 (2H, m), 3.407 (3H, s, OMe), 2.89 (1H, s), 2.22 (3H, m), 1.911 (3H, m), 1.669 (1H, s), 1.528 (3H, s, Me), 1.416 (3H, s, Me). δ $^{13}$C (CDCl$_{3-125}$ MHz): 171.136, 164.460, 157.762, 150.988, 149.577, 145.913, 140.549, 137.758, 136.043, 129.754, 128.480, 127.744,126.242, 123.731, 113.065, 111.510, 84.716, 77.206, 70.144, 55.101, 45.732, 38.115, 20.986, 12.452. IR (KBr pellet): 3467 (O—H), 3285, 3248 (N—H), 3070 (Aromatic C—H), 2950 (Aliphatic C—H), 2328, 1683 (C=O), 1545, 1457, 1267, 1063. mlz : FAB 796 (M+H)$^+$. Analysis: Calculated (C-61.9%, H-5.7%), Found (C-62%, 1H-5.68%).

Synthesis of 5'—N-MmTr-TtTtT-3'—OH (Compound 9b)

To a solution of 95 mg (0.171 mumole) of 3'-isothiocyanate-5'—N-MmTr-3', 5'-dideoxythymidine in 10 ml of anhydrous pyridine was added 100 mg (0.170 mmole) of 20 5'—NH$_3$+-TtT-3'—OH (Compound 10a) followed by 8 mg of dimethylaminopyridine and the resulting solution stirred at room temperature for 7 hr. Pyridine is evaporated under pressure and 15 ml of chloroform is added to the residue to precipitate the product and remove any unreacted isothiocyanate. TLC analysis in EtOAc:MeOH (8:2) shows complete disappearance of the amine ($R_f$=0.2) The product has a $R_f$ value of 0.4. The white product obtained is filtered, washed with 20 ml of water and dried to give 162 mg of a crystalline product (89.0%). $^1$H NMR-400 MHz (d$_6$-DMSO): δ 11.34 (3H, br, NH), 7.983 (2H, br, NH), 7.645 (1H, s, 6—H), 7.535 (1H, s, 6—H), 7.390 (4H, d, J=7.6 Hz, trityl-H), 7.270 (4H, m, trityl-H), 7.16 (2H, t, J=7.6 Hz, trityl-H), 6.810 (2H, d, J=5.2 Hz, trityl-H), 6.177 (2H, t, J=6.8 H 0 MHz (d$_6$-DMSO): (11.34 (3H, br, NH), 7.983 (2H, br, NH), 7.645 (1H, s, 6—H), 7.535 (1H, s, 6—H), 7.390 (4H, d, J=7.6 Hz, trityl-H), 7.270 (4H, m, trityl-H), 7.16 (2H, t, J=7.6 Hz, trityl-H), 6.810 (2H, d, J=5.2 Hz, trityl-H), 6.177 (2H, t, J=6.8 Hz, 1'—H), 6.122 (2H, t, J=6 Hz, 1'—H), 5.350 (1H, d, J=4 Hz), 4.714 (1H, br, OH), 4.191 (3H, m), 3.945 (2H, br), 3.854 (3H, m), 3.707 (3H, s, OMe), 3.563 (3H, m), 2.974 (2H, s), 2.355 (3H, m), 2.146 (3H, m), 1.806 (3H, s, Me), 1.793 (3H, s, Me), 1.706 (3H, s, Me). δ $^{13}$C (d$_6$-DMSO-125 MHz): 163.708, 163.677, 157.404, 150.485, 150.439, 150.409, 146.214, 137.755, 135.821, 129.608, 128.272, 127.703, 126.088, 113.032, 109.898, 109.527, 84.386, 83.386, 83.817, 83.05, 71.246, 69.706, 54.966, 38.742, 38.299, 44.808, 38.266, 12.430, 12.256, 12.134. m/z : FAB 1079 (M+H)$^+$, Analysis: Calculated (C-57.9%, H-5.5%), Found (C-57.67%, H-5.46%).

Synthesis of 5'—N-MmTr-TtTtTtT-3'—OH (Compound 9c)

To a solution of 120 mg (0.111 mmole) of 5'—N-MmTr-TtT-3'—OH (Compound 9b) in 15 ml of chloroform was added 15 ml of acetic acid. The resulting solution was stirred at room temperature for 4 hr. TLC analysis in BuOH:CH$_3$COOH:H$_2$O (5:2:3) shows complete disappearance of the starting material (R$_f$=0.5) The product has a R$_f$ value of 0.4. The solvents were then evaporated under pressure and to the resulting gel was added 100 ml of diethyl ether. The white precipitate obtained was centrifuged and washed with diethyl ether and dichloromethane to give 95 mg of dry product (compound 10b-98.8%). m/z: FAB 806.88 (M+H)$^+$.

To a solution of 110 mg (0.1983 mmole) of 3'-isothiocyanate-5'—N-MmTr-3', 5'-dideoxythymidine in 10 ml of anhydrous pyridine was added 95 mg (0.109 mmole) of 5'—NH$_3$+-TtTtT-3'—OH (compound 10b) followed by 20 mg of dimethylaminopyridine and the resulting solution stirred at room temperature for 8 hr. Pyridine is evaporated under pressure and the residue washed with 2×20 ml of chloroform to precipitate the product and remove any unreacted isothiocyanate. TLC analysis in BuOH:CH$_3$COOH:H$_2$O (5:2:3) shows complete disappearance of the amine (R$_f$=0.3) The product has a R$_f$ value of 0.6. The white product obtained is filtered, washed with 2×10 ml of water and dried to give 134 mg of product (89.9%). $^1$H NMR-400 MHz (d$_6$-DMSO): δ 11.428 (4H, br, NH). 8.210 (2H, d, J=6.4 Hz, trityl-H), 8.095 (1H, s, 6—H), 7.745 (1H, s, 6—H), 7.635 (1H, s, 6—H), 7.573 (1H, s, 6—H), 7.490 (4H, d, J=7.6 Hz, trityl-H), 7.360 (4H, dd, J=7.6 Hz, J=6.8 Hz, trityl-H), 6.920 (2H, d, J=8.8 Hz, trityl-H), 6.730 (2H,d, J=6.4 Hz, trityl-H), 6.276 (3H, t, J=6.4 Hz, 1'—H), 6.224 (1H, t, J=6.4 Hz, 1'—H), 5.446 (2H, br), 4.819 (1H, br, OH), 4.2–4.0 (4H, m), 3.809 (3H, s, OMe), 3.604 (4H, m), 2.65–2.45 (8H, m), 2.310–2.416 (4H, m), 1.914 (6H, d, J=1.2, Hz, Me), 1.893 (3H, s, Me), 1.86 (3H, d, J=1.2 Hz, Me), 1.808 (3H, s, Me). δ $^{13}$C (d$_6$-DMSO-125 MHz): 182.474, 163.660, 157.299, 150.399, 150.362, 147.941, 146.174, 137.692, 136.023, 135.849, 129.552, 128.217, 127.648, 126.032, 112.976, 109.889, 109.836, 109.472, 106.687, 84.346, 83.785, 83.504, 82.996, 82.260, 71.199, 69.644, 54.904, 46.673, 44.806, 38.669, 38.517, 38.244, 36.226, 12.00 (4 Me). m/z: FAB 1361 (M+H)$^+$.

5'—N-MmTr-TtTtTtTtT-3'—OH (Compound 9d)

To a solution of 120 mg (0.088 mmole) of 5'—N-MmTr-TtTtTtT-3'—OH (Compound 9c) in 20 ml of chloroform was added 10 ml of acetic acid. The resulting solution was stirred at room temperature for 4 hr. TLC analysis in BuOH:CH$_3$COOH:H$_2$O (5:2:3) shows complete disappearance of the starting material (R$_f$=0.6) The product has a R$_f$ value of 0.35. The solvents were then evaporated under pressure and to the resulting gel was added 100 ml of diethyl ether. The white precipitate obtained was centrifuged and washed with diethyl ether (2×15 ml) and dichloromethane (2×15 ml) to give 100.5 mg of dry product (10c-99.5%). m/z: 1089.20 (M+H)$^+$.

To a solution of 105 mg (0.189 mmole) of 3'-isothiocyanate-5'—N-MmTr-3', 5'-dideoxythymidine (Compound 7) in 10 ml of anhydrous pyridine was added 95 mg (0.0827 mmole) of 5'—NH$_3$$^+$-TtTtTtT-3'—OH (10c) followed by 25 mg of dimethylaminopyridine and the resulting solution stirred at room temperature for 6 hr.

Pyridine is evaporated under pressure and the residue washed with 2×20 ml of chloroform to precipitate the product and remove any unreacted isothiocyanate. TLC analysis in BuOH:CH$_3$COOH:H$_2$O (5:2:3) shows complete disappearance of the amine (R$_f$=0.35). The product has a R$_f$ value of 0.65. The white product obtained is filtered, washed with 2×10 ml of water and dried to give 129 mg of product (95.5%). $^1$H NMR-400 MHz (d$_6$-DMSO): 11.351 (5H, br, NH), 8.126 (1H, s, 6—H), 8.114 (1H, s, 6—H), 8.048 (1H, br, NH), 7.667 (2H, br, NH), 7.543 (2H, br, 6—H), 7.479 (1H, s, 6—H), 7.39 (4H, d, J=5.6 Hz, trityl-H), 7.259 (4H, m, trityl-H), 7.154 (2H, d, J=5.6 Hz, trityl-H), 6.81 (2H, d, J=6.8 Hz, trityl-H), 6.68 (2H, d, J=5.6 Hz, trityl-H), 6.16 (5H, m, 1'—H), 4.707 (3H, m), 4.19–3.82 (12H, m), 3.70 (3H, OMe), 3.684 (2H, s), 3.567 (2H, br), 2.998 (5H, s), 2.372 (5H, m), 2.139 (5H, m), 1.9 (1H, s), 1.807 (6H, s, Me), 1.79 (3H, s, Me), 1.759 (3H, s, Me), 1.705 (3H, s, Me). δ $^{13}$C (d$_6$-DMSO-125 MHz): 182.684, 172.218, 170.048, 163.767, 157.420, 154.863, 150.690, 150.530, 150.483, 149.631, 146.273, 137.771, 137.581, 137.042, 136.117, 135.997, 135.895, 129.650, 128.303, 127.742, 126.125, 123.959, 113.049, 110.001, 109.950, 109.564, 107.682, 106.786, 84.439, 83.612, 83.077, 82.672, 82.268, 81.675, 80.746, 79.210, 74.570, 71.286, 69.725, 55.395, 54.983, 54.142, 46.801, 44.784, 38.936, 38.306, 36.780, 36.343, 35.258, 21.198, 20.867, 12.499, 12.313, 12.233, 12.193. IR (KBr pellet): 3464 (O—H), 3288, 3228 (N—H), 3060 (Aromatic C—H), 2943 (Aliphatic C—H), 1689 (C═O), 1542, 1455, 1266, 1063. m/z : FAB, 1643 (M+H)$^+$. Analysis: Calculated (C-54.1%, H-5.3%), Found (C-53.96%, H-5.17%).

Synthesis of 5'—NH3+-TtT-3'—OH (Compound 10a)

To a solution of 120 mg (0.150 mmole) of 5'—N-MmTr-TtT-3'—OH (Compound 9a) in 20 ml of chloroform was added 10 ml of acetic acid. The resulting solution was stirred at room temperature for 4 hr. TLC analysis in BuOH:CH$_3$COOH:H$_2$O (5:2:3) shows complete disappearance of the starting material (R$_f$=0.8) The product has a R$_f$ value of 0.4. The solvents were then evaporated under pressure and to the resulting gel was added 100 ml of diethyl ether. The white precipitate obtained was centrifuged and washed with diethyl ether and dichloromethane to give 75 mg of dry product (94.9%). $^1$H NMR-400 MHz (d4-MeOD): δ 7.350 (1H, s, NH), 7.331 (1H, s, NH), 7.081 (2H, d, J=1.2 Hz, 6—H), 6.063 (1H, t, J=7.2 Hz, 1'—H), 5.955 (1H, t, J=6.4 Hz, 1'—H), 4.185 (2H, m, 3'—H), 3.88 (3H, m), 3.676 (3H, s, br, NH3+), 3.368 (1H, d, J=3.2 Hz), 3.327 (1H, d, J=3.2 Hz), 3.157 (2H, m), 2.480 (1H, br, OH), 2.235 (1H, m), 2.105 (2H, m), 1.779 (3H, s, CH$_3$CO$_2$ ), 1.744 (3H, d, J=1.2 Hz, Me), 1.733 (3H, d, J=1.2 Hz, Me). δ $^{13}$C (d4-MeOD-125 MHz): 178.892, 166.405, 152.416, 152.340, 139.588, 138.245, 112.012, 111.944, 88.487, 86.796, 86.363, 82.676, 73.019, 56.519, 42.887, 39.905, 36.810, 23.276, 12.944, 12.648, 12.466. IR (KBr pellet): 3500–2700 (0—H, N—H+C—H), 2342, 1688 (C═O), 1545, 1459, 1267, 1060. m/z: FAB, 525 (M+H)$^+$.

Synthesis of 5'—NH$_3$$^+$-TmtTmtT-3'—OH (Compound 11b)

To a solution of 7 mg (6.49 (mole) of 5'—N-MmTr-TtTtT-3'—OH in 3 ml of dimethylformamide was added 5 ml of ethanol and 20 ml of methyl iodide. The resulting solution was stirred at 40° C. for 5 hr. The solvents were then evaporated under pressure and to the resulting gel was added 20 ml of acetic acid and stirred for another 2 hr. Acetic acid was then evaporated off and the glue like residue dissolved in methanol and precipitated with ether. The precipitate was collected by centrifugation and reprecipitated from methanol-ether to give 4.9 mg of a yellowish product. (84.4%). m/z: FAB 834.2 (M+H)$^+$, Analysis: Calculated (C-48.8%, H-6.0%.), Found (C-48.5%, H-6.15%.), $\lambda$.max=266.7 nm.

Synthesis of 5'—NH3+-TmtTmtTmtT-3'—OH (Compound 11c)

To a solution of 10 mg (7.35 μmole) of 5'—N-MmTr-TtTtTtT-3'—OH (Compound 9c) in 3 ml of dimethylformamide was added 5 ml of ethanol and 15 ml of methyl iodide. The resulting solution was stirred at 40° C. for 5 hr. The solvents were then evaporated under pressure and to the resulting gel was added 20 ml of acetic acid and stirred for another 2 hr. Acetic acid was then evaporated off and the glue like residue dissolved in methanol and precipitated with ether. The precipitate was collected by centrifugation and reprecipitated from methanol-chloroform to give 8 mg of a yellowish product. (79.5%). mlz : (FAB)1 129 (M+H)$^+$, $\lambda$.max=266.4 nm.

To extend the synthesis to the formation of polymeric dNmt, attempts were initially made to protect the 3'-hydroxyl with a base labile protecting group so that a) the 3'-5' chain extension could be carried out by deprotection of the acid labile trityl group, b) improve the solubility of monomer 8 and thioureas in organic solvents and c) eliminate any possibility of reaction between the 3'-hydroxyl and the 3'-isothiocyanate 7. Since initial attempts to carry out that transformation were unsuccessful, anhydrous pyridine was used as a solvent to couple 5'-amino deoxythymidine 8 with 5'—N-Mmtrityl-3'-isothiocyanate dideoxythymidine. The reaction proceeds to completion in few hours and the 3'—OH has no reactivity with the isothiocyanate. The lack of a protecting group at the 3'—OH was useful because of the ease in purification of polymeric thioureas that resulted from it. While 5'—N-tritylated thioureas are soluble in some organic solvents, the detritylated amines are easily precipitated on addition of chloroform or ether simplifying the complete purification process as described above.

Synthesis of 5'—NH3+-TmtTmtTmtTmtT-3'—OH (Compound 1id)

The synthesis of compound 11d was then accomplished via a cyclic process starting with a condensation reaction between 3'-isothiocyanate-5'—N-Mmtrityl-3', 5'-deoxythymidine (compound 7) and 5'-amino-5'-deoxythymidine (compound 8), affording the 3'-5' thiourea-linked dimer 9. The synthesis of compound 7 was carried out by protection of 5'-amino-3'-azido-3'→5'-dideoxythymidine (Dempcy et al., (1994), supra and Dempcy et al., *Proc. Natl. Acad. Sci. USA*, 92:6097 (1995), supra) with monomethoxytrityl chloride followed by hydrogenation of the azido group. The reaction of the resulting 3'-amino-5'-N-Mmtrityl-3', 5'-deoxythymidine with excess thiopyridone (Kim et al., *J. Org. Chem.* 51:2613 (1986)) at room temperature followed by flash chromatography gave compound 7 in 65% overall yield. Chain extension from the dimer followed a cyclic two-step process involving deprotection of the 5'-amino group with acetic acid.

The resulting amine was then allowed to condense, in near quantitative yields, with another equivalent of compound 7 in pyridine for 4–8 hr., depending upon the length of the oligomer. 4-Dimethylaminopyridne was added in 5–10% molar quantities to speed up the reaction. The thiourea-linked thymidyl oligomers compounds 10b–d were successfully converted to compounds 11b–d by methylation of the thiourea linkages to methylisothiouronium salts in excess methyl iodide. The reaction can be carried out at room temperature or heated at 40° C., if necessary. Excess heating for over 4 hours, however results in partial methylation of the 3'—OH. Deprotection of methylated polymers with acetic acid was followed by a purification on a preparative Alltech WCX cation exchange column employing 1.50 M ammonium acetate buffer, pH 6–7.0, as the mobile phase. The purity of the sample was further confirmed by passing it through an analytical cation exchange column with IM guanidine HCl as the eluant. HPLC chromatograms of compounds 11b–d show that compounds 11b, 11c and lid have retention times of 9.8, 14 and 18 minutes, respectively, consistent with the presence of three, four and five positive charges.

To a solution of 20 mg (0.012 mmole) of 5'—N-MmTr-TtTtTtTtT-3'—OH (compound 9d) in 3 ml of dimethylformamide was added 5 ml of ethanol and 20 ml of methyl iodide. The resulting solution was stirred at 40° C. for 5 hr. The solvents were then evaporated under pressure and to the resulting gel was added 20 ml of acetic acid and stirred for another 2 hr. Acetic acid was then evaporated off and the glue like residue dissolved in methanol and precipitated with ether. The precipitate was collected by centrifugation and reprecipitated from methanol-ether to give 19 mg of a yellowish product (90.47%). The product was then purified on a preparative Alltech WCX cation exchange column employing 1.50 M ammonium acetate buffer, pH 7.0, as the mobile phase. The purity of the sample was further confirmed by running it on an analytical cation exchange column with IM guanidine HCl as the eluant. The HPLC chromatogram of compound 11d has a retention time of 18 minutes, consistent with the presence of 5 positive charges. IR (KBr pellet): 3275, 3239(N—H), 3060 (Aromatic C—H), 2948 (Aliphatic C—H), 1690 (C=O), 1542, 1455, 1264, 1063. m/z: (FAB)1427 (M+H)$^+$, (ESI): 1427.4 (M+H)$^+$, 714.3 (M+2H)$^{2+}$, $\lambda$.max=266.7 nm.

EXAMPLE III

Equilibrium Complexes of Thymidyl DNmt with poly (adenylic) Nucleic Acids

This Example characterizes equilibrium complexes of pentameric Tmt with poly(adenylic) nucleic acids: poly(da) and poly(rA).

Figure 10A:
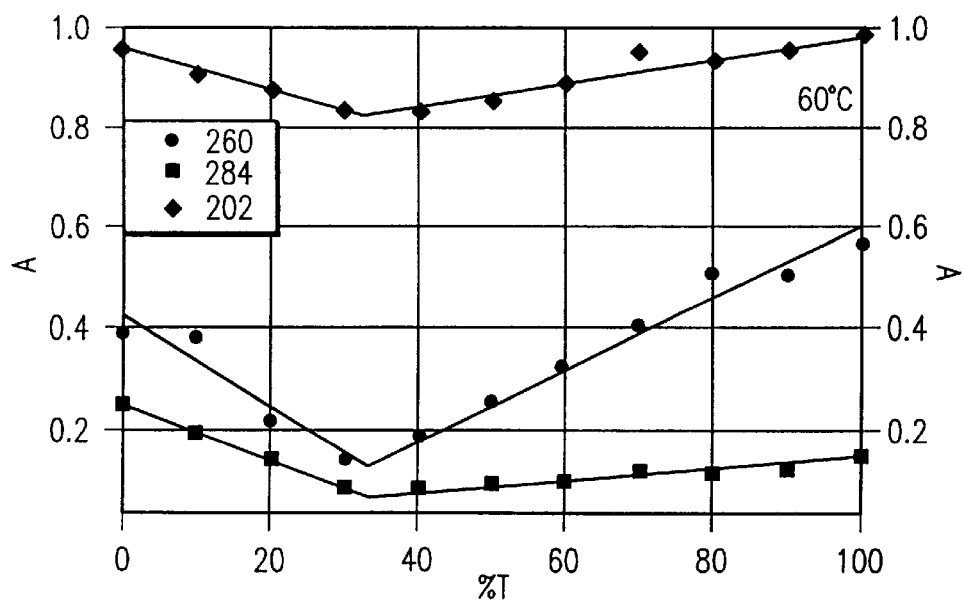
FIGS. 10a and 10b.
Figure 10B:
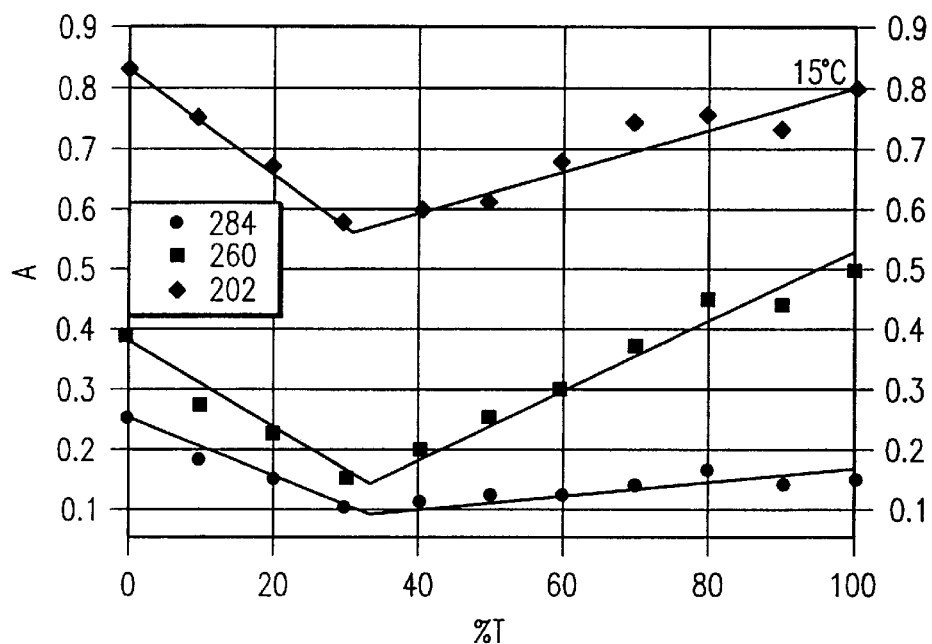

To investigate the interaction of compound 11d {5'—NH$_3$+-T$_{mt}$-(T$_{mt}$)$_4$—OH} with polynucleotides, UV continuous variation plots were constructed at different ionic strengths ($\mu$), wavelengths and temperatures. The method of continuous variation is based on the assumption that the decrease in absorbance is proportional to the number of base pairs hydrogen bonded between the interacting species. Mixtures of compound 11d with poly(rA) at 30° C. (FIG. 3) reached a minimum absorbance at a mole fraction of ~0.66 d(Tmt) to 0.34 r(Ap) (single phosphate-linked riboadenosyl unit). These numbers indicate that triple-stranded complexes are formed containing two d(Tmt) for every r(Ap). The same results are obtained at 202 and 280 nm. The absorbance change was much larger and the intersection of lines much easier to define at 202 nm. At 15° C. and 60° C. the plots (FIGS. 10a and 10b) have a minima at 0.67 mole percent of d(Tmt) at all three wavelengths.

These results confirm the stable triple helical nature of the DNmt-RNA complex suggested by the lack of hyperchromic shifts in the thermal denaturation studies from 15 to 60° C.

Figure 3:
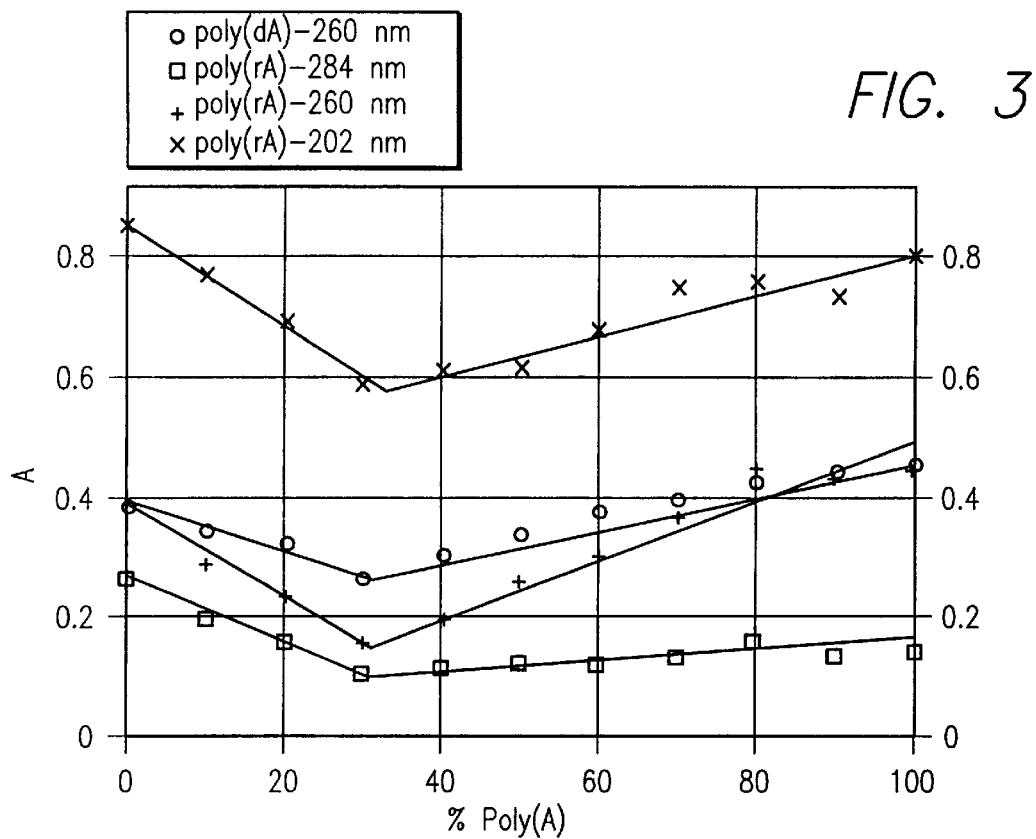
FIG. 3. Job Plots of poly(rA) ($5.3\times10^{-5}$M), poly(da) ($5.3\times10^{-5}$M) and compound 11d in 15 mM $K_2HPO_4$, 0.15M KCl, pH 7.5 at 30° C.

The plot for compound 11d with poly(dA) at 30° C. is also centered near a mole fraction of 0.67 d(Tmt) to 0.33 d(Ap) (FIG. 3). Unlike the mixing curves with r(Ap), these curves are much shallower as the percent hypochromicity is much lower in binding to poly deoxynucleotides. Equilibrium complexes are the same from 30 to 60° C., and confirm the stable triple helical nature of the complexes that DNmt forms with polydeoxy adenosyl nucleotides.

Although these results establish that the three-stranded complexes $d(Tmt)_2 \cdot r(Ap)$ and $d(Tmt)_2 \cdot d(Ap)$ form under these conditions, they do not specify the composition of equimolar mixtures of d(Tmt) with r(Ap) and d(Ap). It is well-known that the formation of AT2 and AU2 complexes leads to a hypochromic shift at 280 nm, whereas formation of AT and AU complexes does not. Thus A:T is isochromic at this wavelength with respect to A+T, and mixing curves carried out at 280 nm show no hypochromism (Riley et al., *J. Mol. Biol.* 20:359 (1966)).

Figure 4:
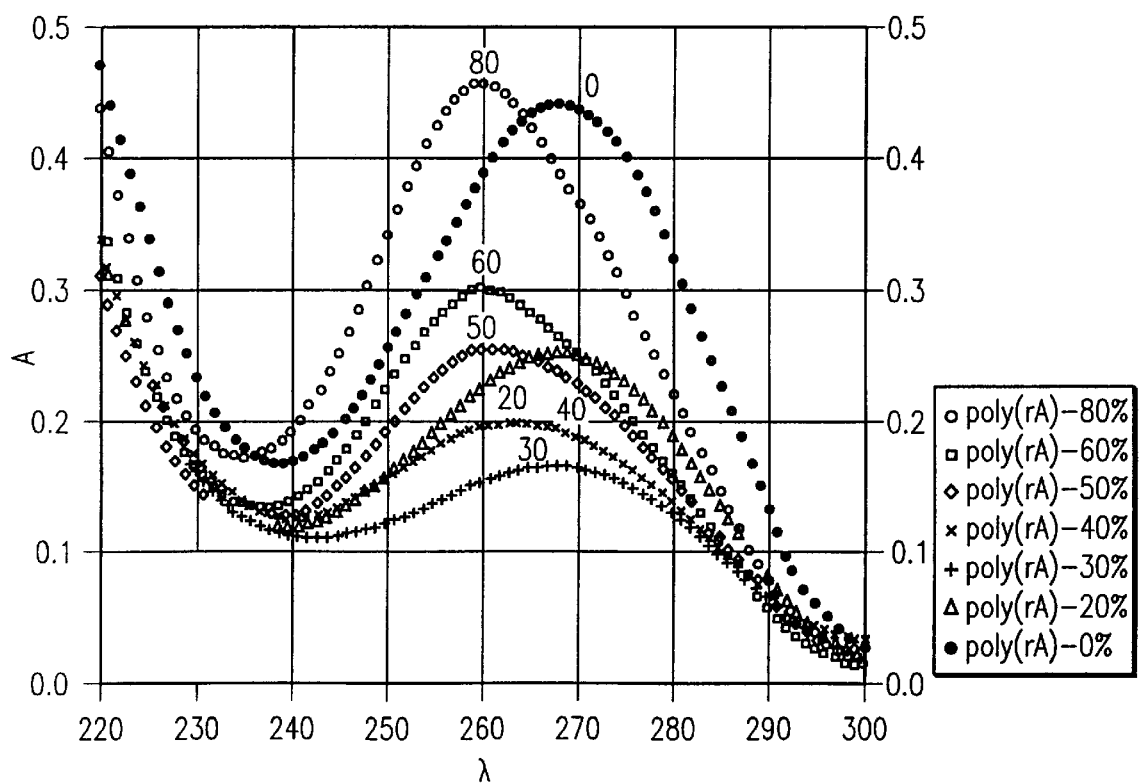
FIG. 4. Titration scans of poly(rA) ($5.3\times10^{-5}$ M) and compound 11d (80% polyrA to 0% polyrA) in 15 mM $K_2HPO_4$, 0.15 M KCl, pH 7.5 at 15° C.

In particular, one cannot determine from these results whether two-stranded $d(Tmt) \cdot r(Ap)$ is present in equimolar mixtures, or whether the equilibrium products are always $d(Tmt) \cdot r(Ap)_2$ and free rA polymer. Continuous variation experiments were carried out with the measurement of complete spectra of each of the different mixtures (FIG. 4) (Riley et al., supra). FIG. 4 shows that as more of d(Tmt) is being added (decreasing % of polyrA), there is a lowering of absorbance at almost all wavelengths.

Mixing curves with 0 to 50% Tmt are hypochromic at all wavelengths between 235 and 285 nm and curves at any wavelength, where a spectral change occurs, consist of two intersecting straight lines with a single minimum at 66% Tmt residues. The hypochromicity in wavelengths greater than 280 nm is more pronounced at 15° C. as opposed to 60° C. Since it is unlikely that $d(Tmt) \cdot rA$ has the same absorbency per nucleotide over this entire spectral range as the mixture $rA + rA \cdot d(Tmt)_2$, a 1:1 complex does not exist in appreciable amounts in solutions under these experimental conditions. The sole complex is $rA \cdot d(Tmt)_2$.

Figure 5:
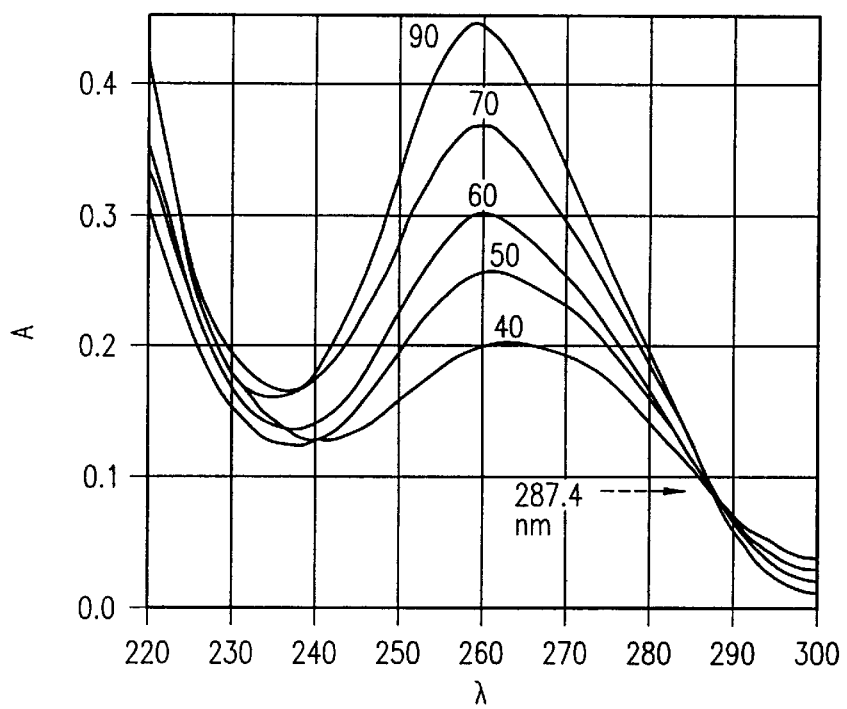
FIG. 5. Titration scans of poly(rA) ($5.3\times10^{-5}$M) and compound 1d (90% polyrA to 40% polyrA) in 0.15 mM $K_2HPO_4$, 0.15 M KCl, pH 7.5 at 15° C., showing the inflection point at 287.4 nm.

From the titration scans (FIG. 4), there appear two isosbestic points for d(Tmt) and poly(rA) mixtures. The first occurs at 287.4 nm in 0 to 66% d(Tmt) mixtures (FIG. 5) due to an equivalence of extinction coefficients for rA and $rA \cdot d(Tmt)_2$ ; the second occurs at 296 nm in 67 to 100% d(Tmt) and is due to an equivalence of extinction coefficients for d(Tmt) and $rA \cdot d(Tmt)_2$.

EXAMPLE IV
Thermal Denaturation Studies

Annealing and melting curves of complexes formed from compound 11d {5'—$NH_3^+$Tmt-$(Tmt)_4$—OH} with DNA/RNA homo-oligomers exhibit hysteresis (FIG. 6) at the rate of heating-cooling employed (0.13 deg/min). Rates of heating and cooling of up to 0.5 deg/min are generally slow enough to ensure attainment of the equilibrium in the case of duplex to coil transitions in oligonucleotides, i.e., heating and cooling curves coincide.

The melting and annealing behavior of DNmt complexes with poly(rA) and poly(da) was studied at different ionic strength ($\mu$) at a rate of 0.13 deg/min. At low $\mu$ the hysteresis observed is abnormally large. Examination of FIG. 6a reveals the cause of this large hysteresis. The complex $rA \cdot d(Tmt)_2$ continues to melt after reaching the terminal temperature of 95° C., this leads to an initial apparent increase in absorbance as the temperature descent begins, thus causing the abnormally large hysteresis curve.

Figure 6A:
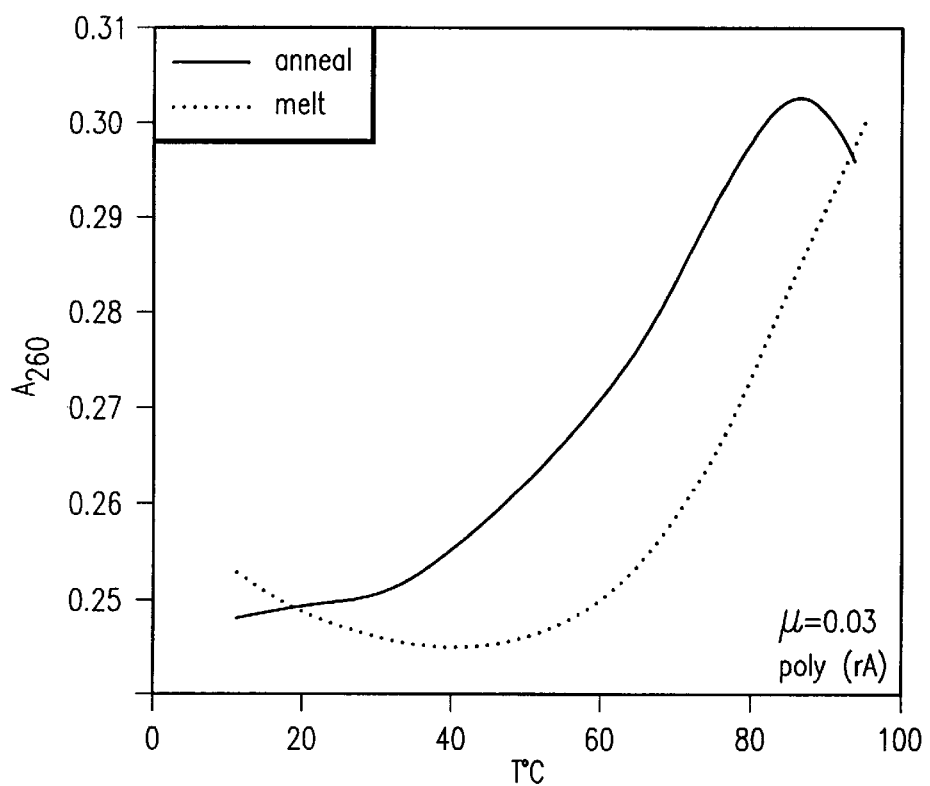
FIGS. 6a–6d. Hysteresis curve of 1id and poly (rA) in 8.5 mM $K_2HPO_4$, 8.5 mM $Na_2HPO_4$ KCl, pH 6.85 at different ionic strengths ($\mu$=0.06–0.3); (d) Hysteresis curve of compound 11d and dA-20 in 8.5 mM $K_2HPO_4$, 8.5 mM $Na_2HPO_4$ KCl, pH 6.85 at an ionic strength of 0.03 (KCl). Data were recorded every 0.4 deg. The samples were heated from 25 to 95° C. at 5 deg/min, the annealing (95–5° C.) and the melting (5–95° C.) were conducted at 0.13 deg/min, and the reaction solutions were equilibrated for 15 minutes at the highest and lowest temperatures.
Figure 6B:
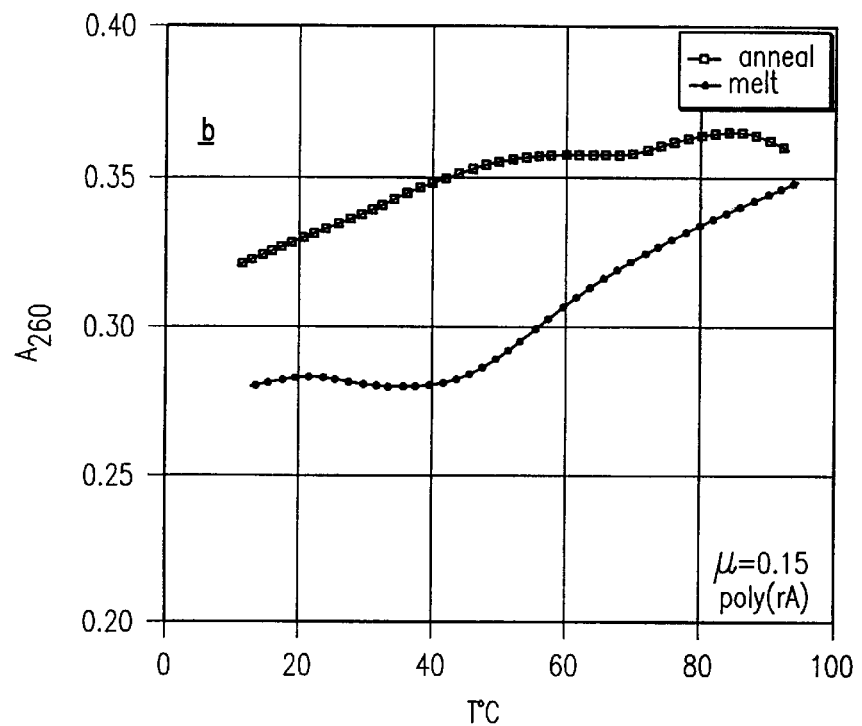
Figure 6C:
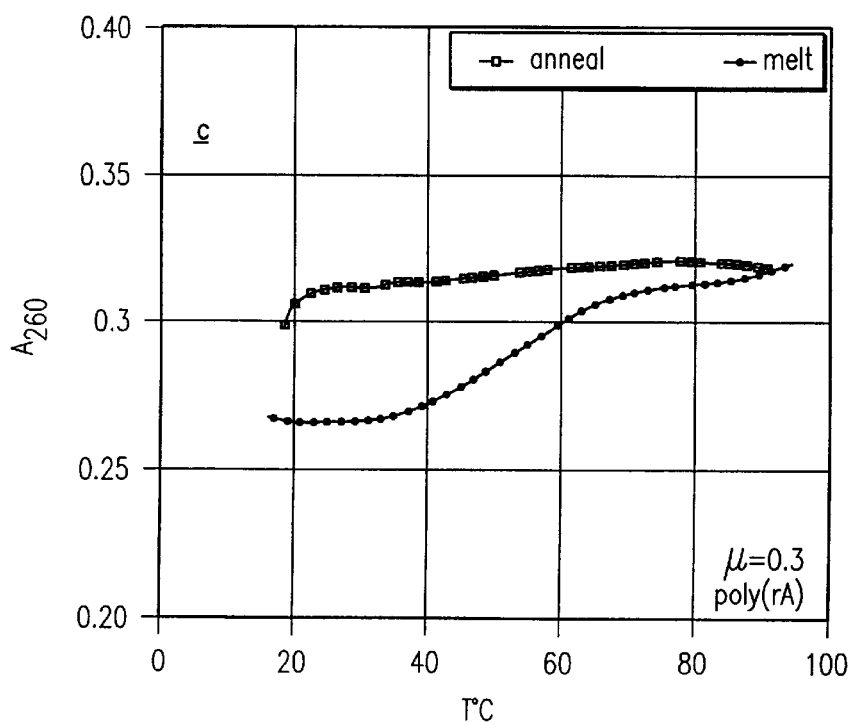
Figure 6D:
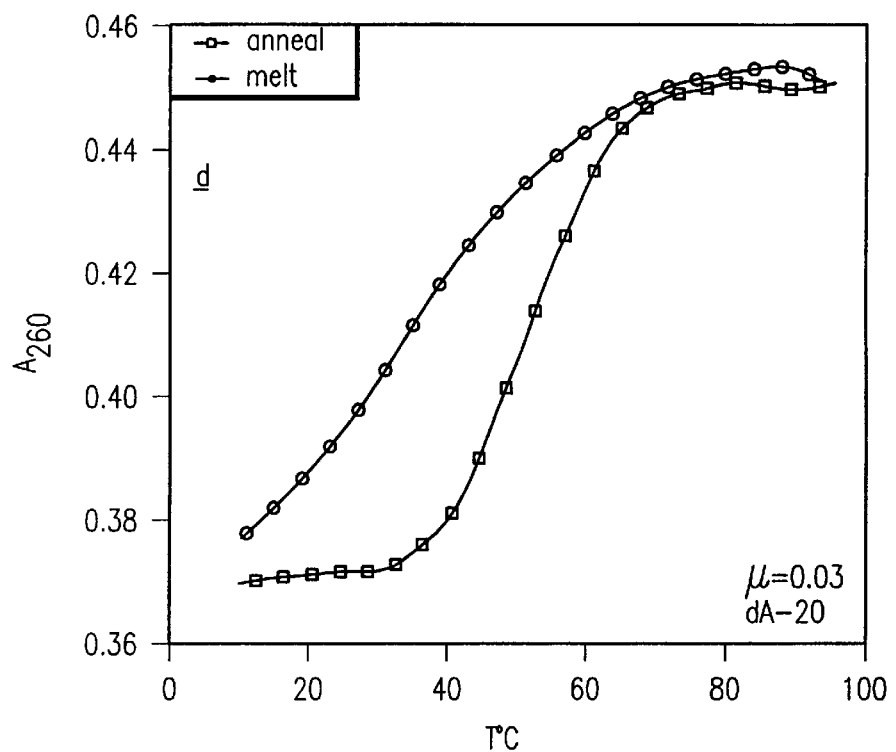

With an increase in $\mu$ (FIGS. 6b, 6c) annealing becomes slower. Denaturation studies at high ii show larger hysteresis because the positive and negative charges are attenuated by added salt. As stated previously, the large hysteresis at lower $\mu$ can be attributed to the limitation of melting points measurement to 100° C. This behavior is clarified on studying the melting behavior (FIG. 6d) of $d(Tmt)_5$ with dA-20 (a DNA sequence containing 20 adenosine bases). As shown in FIG. 6d, the complex shows an ideal hysteresis curve as the triplex melting is now well below 90° C. and the hysteresis observed at low g is an accurate indication of the melting and annealing processes of dNmt with polynucleotides. In support of these observations is the fact that after thermal melting in a solution containing 0.03 M KCl, re-formation of the $d(Tmt)_2 \cdot poly(dA)$ complex is very slow. The melting mixture does not return to its original absorbency even after standing for 36 hr. at room temperature. The return to original absorbency is even slower at higher ionic strengths. There is a $\mu$ above which the melting transitions for compound 11d complexes with poly(rA) and poly (dA) cannot be observed, or are too shallow to be accurate representations of a melting point. Increasing the concentrations of the respective strands does however show better transitions at these ionic strengths.

EXAMPLE V
Fidelity in Binding to Polynucleotides

Figure 7A:
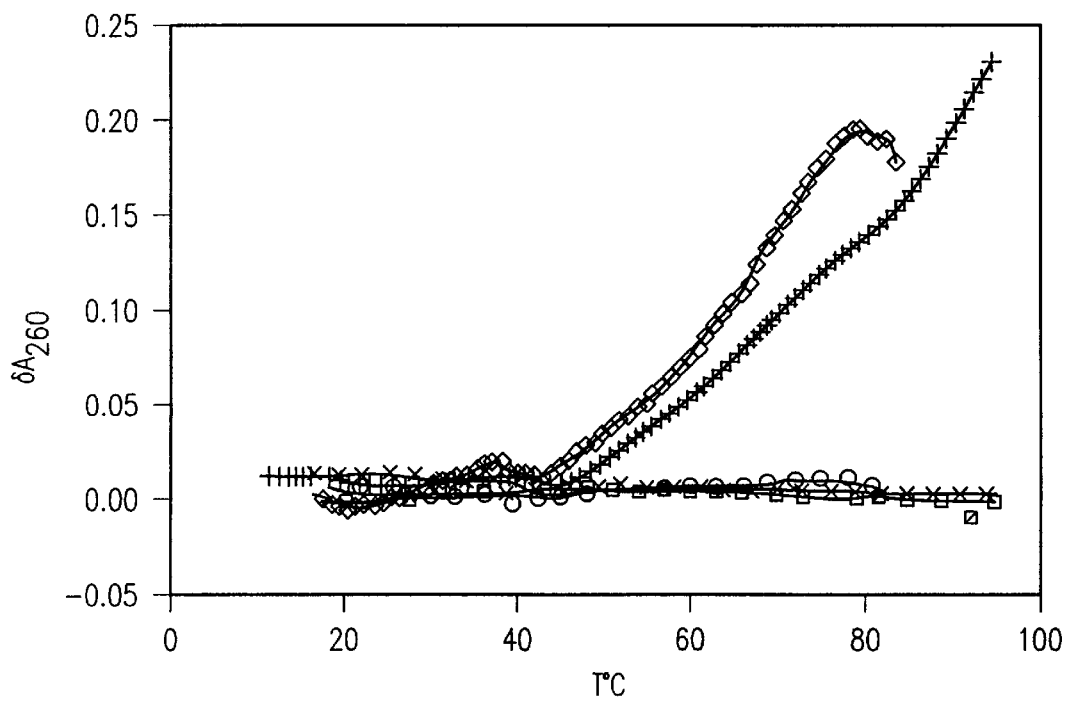
FIG. 7a. Plots of $A_{260}$ vs T (° C.) for compound 11d annealed to poly (dA) (+) at $\mu$=0.03 (KCl), poly (dA) (◇) at $\mu$=0.3(KCl), poly(dG) (open square), poly(dC) (X), and poly(dT) (O) in 8.5 mM $K_2HPO_4$, 8.5 mM $Na_2HPO_4$ pH 6.85 and an ionic strength of 0.15 (KCl). The concentration of each of the oligonucleotides was $2.17\times10^{-5}$ M in bases. The ratio of compound 11d to polynucleotides was 2:1.
Figure 7B:
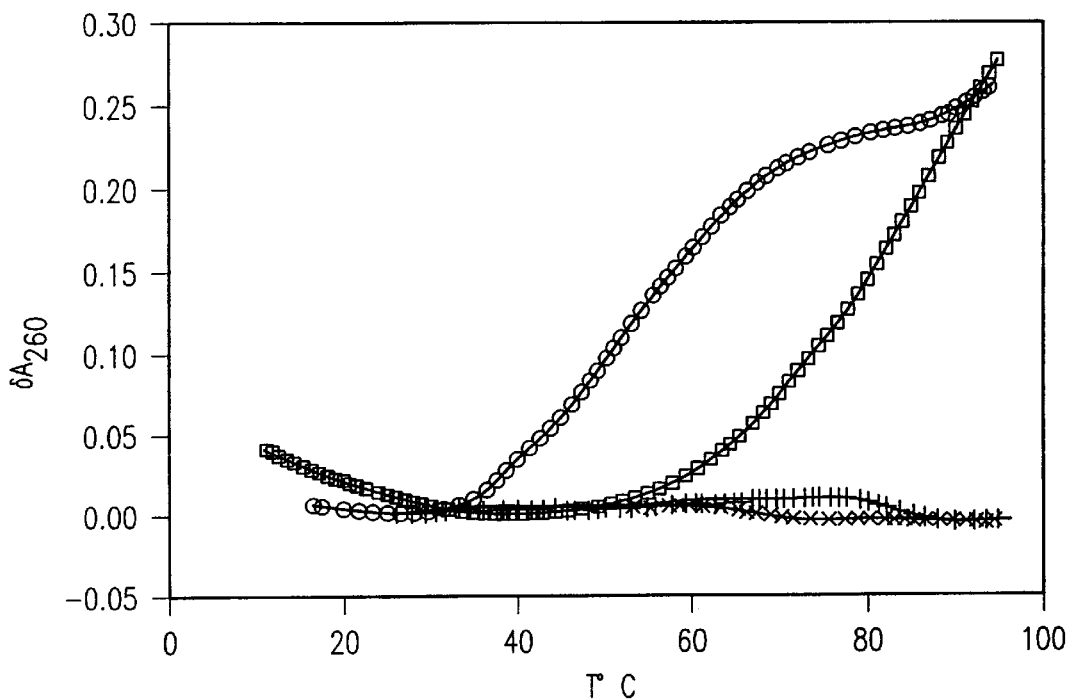
FIG. 7b. Plots of $A_{260}$ vs. T (° C.) for compound 11d annealed to poly(rA) (open square) at $\mu$=0.05 (KCl), poly (rA) (O) at $\mu$=0.12 (KCl), poly(rC) (+), poly(rG) (X) in 8.5 mM $K_2HPO_4$ and 8.5 mM $Na_2HPO$ pH (6.85) and an ionic strength of 0.15 (KCl). The concentration of each of the oligonucleotides was $2.17\times10^{-5}$ M in bases. The ratio of compound 11d to polynucleotides was 2:1.

In the thermal denaturation analysis of compound 11d {5'—$NH_3^+$-Tmt$(Tmt)_4$—OH} bound to poly(dA) (FIG. 7a), plots of absorbance at 260 nm ($A_{260}$) vs. temperature exhibit two distinct inflections (Tm=35° C. and 65° C., $\mu$=0.3). The inflection points in FIG. 7a are assigned to represent denaturation curves of triple- and double-helical structures of compound 11d with ssDNA {$11d_2 \cdot poly(dA)$} and {11d-poly(dA)}. FIG. 7a also indicates that under identical conditions, for solutions which contained compound 11d and either poly(dG), poly(dC), or poly(dT) no hyperchromic shift at 260 nm was observed between ca. 5–93° C. However, in the thermal denaturation analysis of compound 11d bound to poly(rA) (FIG. 7b), plots of $A_{260}$ vs. temperature exhibit only one inflection (Tm=65° C. at $\mu$=0.15 and Tm=85° C. at p=0.03), representing the melting points of the triple-helical structure {$11d_2 \cdot poly(rA)$}. As observed with polydeoxynucleotides, no hyperchromic shift at 260 nm was observed between ca. 5–93° C. for solutions which contained compound 11d and either poly(rG) or poly(rC). There was a hyperchromic shift at <10° C. for the denaturation of poly(rU) annealed to itself. (Browne et al., *Proc. Natl. Acad. Sci. USA* 92:7051–7055 (1995), supra). From these results, dNmt appears to bind with DNA and RNA with specificity in forming hybrid duplex and triplex structures.

Equation 1 (FIG. 13) depicts the annealing process (triplex formation). Rates of formation of triplexes are generally slower than those of duplex formation ($k_2 < k_1$). For example, in studies with RNA·RNA complexes, triplex association rates have been found to be 100 times slower than the duplex association rates. (Porshke, *J. Mol. Biol.* 30:291 (1971)). Electrostatic repulsions between negatively charged phosphates have been suggested as the determining factor in rates of association for RNA and DNA complexes. (Rougee et al., *Biochemistry* 31:9269 (1992)). These electrostatic repulsions become more important in the triplex than in the duplex because the third strand has to come in contact with the duplex that has twice the negative charge of a single strand. Similar rate effects would be expected with dNmt·DNA and dNmt·RNA complexes. The association of Tmt and Ap (eq 1–$k_1$) is expected to be fast due to attraction of the opposite charges of the backbones. Formation of triplex requires the attraction of a positively charged Tmt to a neutral duplex (Tmt·Ap) and thus is expected to be slower than the first step ($k_2 < k_1$). In the continuous variation plots (annealing-FIGS. 3 and 4), formation of the triplex as the major species at low temperatures is then due to the thermodynamic stability of the positively charged Tmt·Ap·Tmt complex over the neutral Ap·Tmt duplex. In melting the triplex below 95° C. one can observe an intermediate duplex at high $\mu$ (such that $k_2'>k_1'$(equation 2, FIG. 13).

Figure 8:
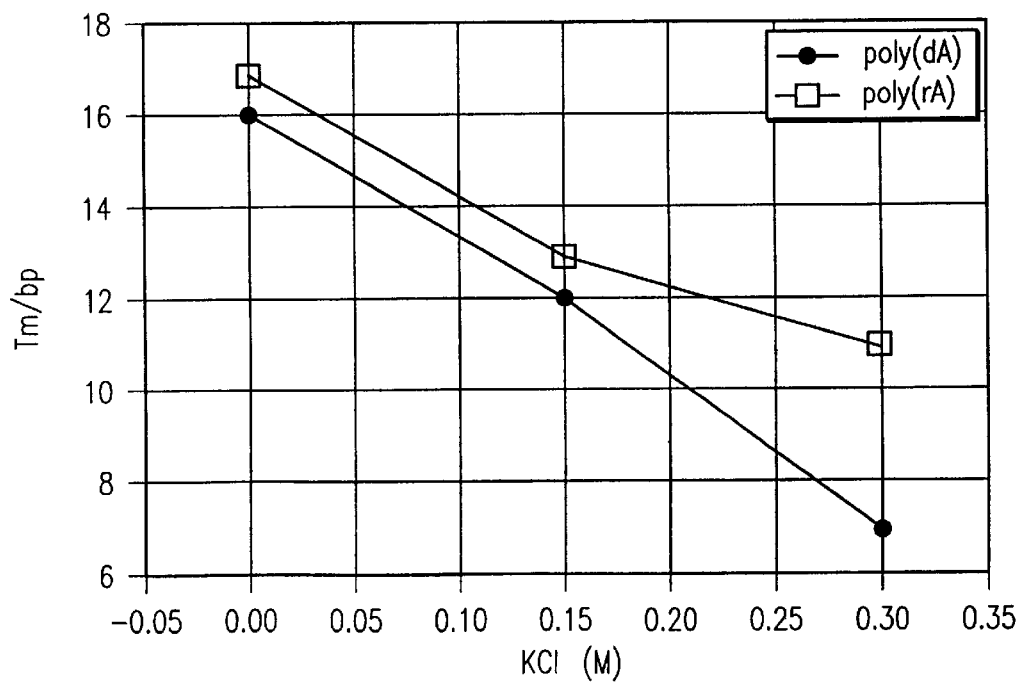
FIG. 8. Plot of Tm of $11d_2$:polyrA/polydA triplexes as a function of ionic strength in 8.5 mM $K_2HPO_4$, 8.5 mM $Na_2HPO_4$ pH 6.85. The concentration of each of the oligonucleotides was $2.17\times10^{-5}$ M in bases. The ratio of compound 11d to polynucleotides was 2:1.

EXAMPLE VI
Effect of Ionic Strength (p) on stability of dNmt·DNA/RNA complexes Compound 11d $\{5'—NH_3^+-T_{mt}-(T_{mt})_4—OH\}$ has a significantly greater affinity for poly(dA) and poly(rA) than does thymidyl DNA. As expected, a change in p has an opposite effect on the Tm values of dNmt hybrids with DNA (FIG. 8) or RNA as compared to DNA complexes with DNA or RNA. This is due to electrostatic interactions being attenuated by increasing salt concentration. Thus, while DNA·RNA duplexes become more stable with increasing $\mu$, DNmt·RNA complexes become more stable with decrease $\mu$. This is in accord with previous experience with DNG·RNA complexes. The oppositely charged backbones of the dNmt·RNA complex provide stability. Increase in $\mu$ saturates the opposite charges and destabilizes the complex. At any given $\mu$ the $d(Tmt)_2$·RNA triplexes are more stable than the $d(Tmt)_2$·DNA triplexes.

Figure 9:
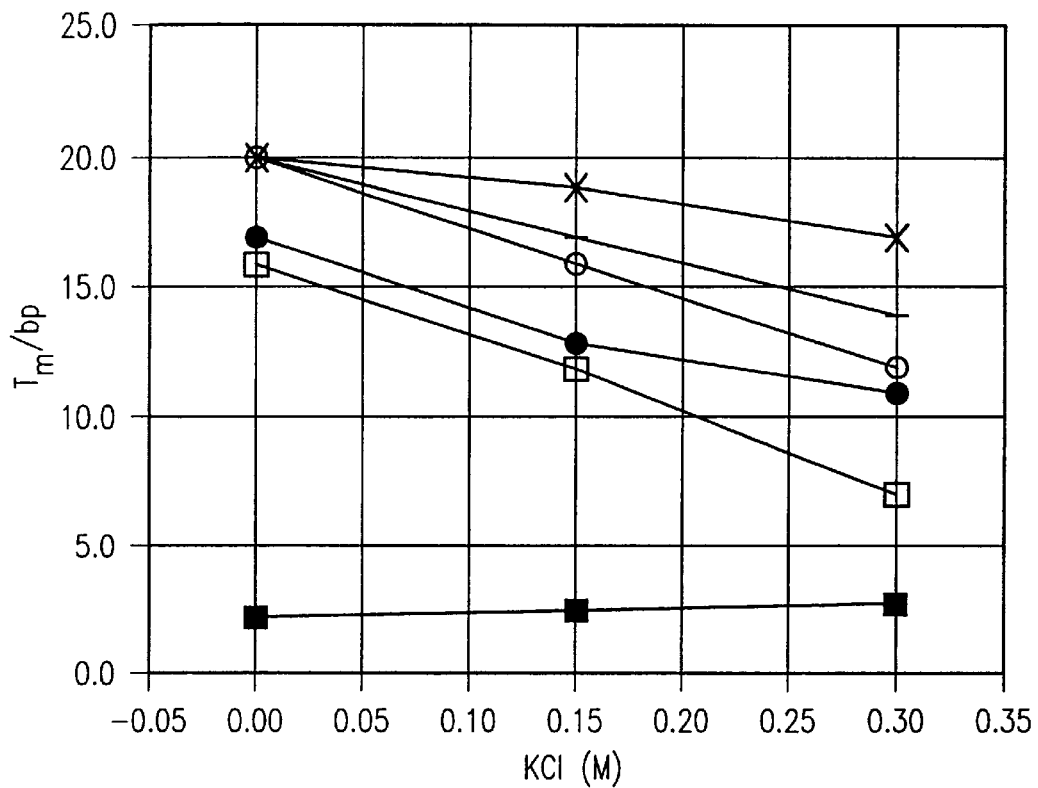
FIG. 9. Plot of Tm per base pair vs.: $\mu$ in 8.5 mM $K_2HPO_4$, 8.5 mM $Na_2HPO_4$ pH 6.85. The plots are DNA. RNA duplex (filled square), DNG.RNA duplex (x) and DNG. DNA (+), DNmt.RNA (filled circle) and DNmt.DNA [first (open circle) and second transitions (open square)]. The concentration of each of the oligonucleotides was $2.17\times10^{-5}$ M in bases. The ratio of compound 11d to polynucleotides was 2:1. Ionic strengths were held constant by adding potassium chloride. The data points at 100° C. for melting of DNG and DNmt complexes are approximations. The melting points for DNG.RNA complexes would be much higher than that for DNmt.RNA complexes.

The thermal denaturation results have been reduced to the unit of Tm per base pair in order to be able to compare Tm values for DNmt bound to RNA and DNA with results of others for DNA bound to modified nucleotides (FIG. 9). The plots of $T_m$/base pair of DNG·RNA duplex and DNG·RNA triplex (Dempcy et al., *Proc. Natl. Acad. Sci. USA* 92:6097 (1995); and Browne et al., *Proc. Natl. Acad Sci. USA* 92:7051–7055 (1995)) as a function of $\mu$ are also presented for comparison. While DNmt binds to poly(rA) and poly(da) over a wide range of ionic strengths, the binding is less strong than shown by DNG. The effect of increasing $\mu$ on the destabilization of dNmt·DNA and dNmt·RNA complexes is much more pronounced compared to DNA·RNA duplexes which become more stable with an increase in $\mu$.

HPLC chromatography of compounds 11b–d indicates that these compounds have retention times of 9.8, 14 and 18 minutes respectively, consistent with the presence of 3, 4 and 5 positive charges.

The above results demonstrate the replacement of the phosphodiester linkages of DNA with ethyl or ether thiourea linkages, such as methylthiourea linkages, to provide the polycation deoxyribonucleic methylthiourea (DNmt). The thermal denaturation analysis of compound 11d $\{5'—NH_3^+$-Tmt-(Tmt)$_4$—OH} bound to Poly(rA) and Poly(dA) exhibits pronounced hysteresis. The DNG polycation-d(Tg)$_4$-T-azido has been shown to bind to poly(da) and poly(rA) with unprecedented affinity and with base-pair specificity to provide both double and triple-stranded helices (Dempcy et al., *Proc. Natl. Acad. Sci. USA* 92:7051–7055 (1995), supra; and Browne et al., supra). Positively charged dNmt, similarly has a significantly greater affinity for poly(dA) and poly(rA) than does the DNA equivalent. The effect of ionic strength on melting is more pronounced with dNmt interacting with poly(A) and has an opposite effect as compared to DNA complexes with DNA or RNA. This is due to electrostatic interactions being attenuated by increasing salt concentrations. The Tm of the double helix of pentameric thymidyl DNA with poly(dA) at $\mu$=0.12 is ca. 13° C., (Browne et al., supra) whereas the dNmt duplex with poly(da) is estimated to be greater than 80° C. At an ionic strength of 0.03, on the other hand, the five bases of dNmt are estimated to dissociate from a double helix with poly(rA) at >80 C.

A comparison with other positively charged oligonucleotides-ethylmorpholino phosphoramidate (Tm/bp=2–3), aminomethyl phosphonate (Tm/bp=2–3) (Letsinger et al., supra), containing positively charged ammonium groups connected via an alkyl linkage (FIG. 1, S6) to the central phosphorus atom of the backbone) and DNG (guanido linked backbone, Tm/bp=15–25), shows that the melting temperatures for DNmt complexes are much higher than the morpholino or aminomethyl linked oligos. While not being bound by any particular theory, this suggests that like DNG, dNmt maintains its positive charge in proper alignment to maximize its interaction with the backbone of the negatively charged phosphates of the opposite strand.

On comparison with DNG, the dNmt complexes are found to melt at a lower temperature (FIG. 9). The fact that dNmts bind less tightly than the guanido compounds (DNGs), provides a measure of the strength of control of binding with the cationic oligonucleotides. Specifically, at low A, a five-mer of DNG does not come off poly(dA) in boiling water. Such strong electrostatic interactions would conceivably cause a loss of fidelity in binding for longer DNG sequences. The presence of an alkylated positively charged thiourea in the dNXt compounds of the invention allows investigation of the balance between charge, hydrophobicity and fidelity, and determination of modifications that may be made to the compounds' hydrophobicity and characteristics such as cellular uptake, to prepare improved therapeutic agents. Compounds derived from the dNXt compounds of the invention, wherein the methyl group has been replaced with other moieties, to investigate the cell permeability and difflusion properties of these compounds, should not alter the enhancement in binding as long as the positive charge rests on the backbone as opposed to the linkers that are tethered to it. The dNXt compounds can be modified to include other nucleobases (A,G,C,T or U). In addition, the chain length can be extended to increase the specificity and strength of binding, e.g. from 0 to 23 units in length. FIG. 14a and b depicts the structure of the dNXt compounds contemplated by the invention.

From these results, the following conclusions can be drawn about the novel dNXt compounds of the invention: (a) positive dNXts, such as Thymidyl dNmt, have much stronger affinity for DNA and RNA, due to electrostatic attractions, than DNA for RNA or vice versa; (b) Thymidyl dNmt is specific for its complementary tracts of adenine bases and does not interact with guanylic, cytidylic, or uridylic tracts; (c) the thermal stability of dNmt·RNA and dNmt·DNA structures is attenuated by increasing salt concentrations; (d) dNmt compounds form triple helical structures from 15–60° C. which are very stable under physiological ionic strength conditions; (e) dNmt compounds binding to poly(rA) is stronger than that to poly(dA); (f) dNmt oligonucleotides can be synthesized with relative ease; (g) have an achiral backbone linkage and (h) are expected to be stable to enzymatic hydrolysis due to the lack of a phosphodiester linkage. These compounds are the first example of a positively charged polynucleotide backbone incorporating a methyl isothiouronium salt.

EXAMPLE VII
Fidelity of Deoxynucleic S-Methythiourea (DNmt) Binding to DNA Oligomers: Influence of C Mismatches.

This example demonstrates the ability of DNmt compounds of the invention to form triplexes with DNA oligomers (1–5, FIG. 16 SEQ ID NO. 1; SEQ ID NO. 2; SEQ ID NO. 3; SEQ ID NO. 4; SEQ ID NO. 5) in solution. The results indicate that thymidyl DNmt binds to adenosyl DNA with remarkable fidelity with a large decrease in binding as the C content of oligos (1–5) SEQ ID NO. 1; SEQ ID NO. 2; SEQ ID NO. 3; SEQ ID NO. 4; SEQ ID NO. 5 is increased.

Experimental:

Materials. DNmt was synthesized as described above Example I and II. The concentrations of nucleotide solutions were determined using the extinction coefficients (per mol of nucleotide) calculated according to the nearest neighboring effects. For d(Tmt)$_5$ we used $\epsilon_{268}$=8700 N$^{-1}$cm$^{-1}$. All experiments were conducted in either a) 0.015 M phosphate buffer, pH 7–7.5 or b) 0.008 M phosphate buffer at pH 6.85. The ionic strength, $\mu$, was adjusted with KCl and is presented with the corresponding concentration of KCl. The concentration of nucleosides, expressed in M/base, was between 1×10$^{-5}$ M and 4.0×10$^{-5}$ M and the ionic strength ranged from 0.03 to 0.12 M KCl. The nucleoside concentration referred to is the limiting component forming the triplex (e.g., a concentration of 4.0×10$^{-5}$ M/base in the reaction of A+2T means [A]=4.0×10$^{-5}$ M/base and [T]=8.0×10$^{-5}$ M/base). All stock solutions were kept at 4° C. between experiments.

Figure 15:
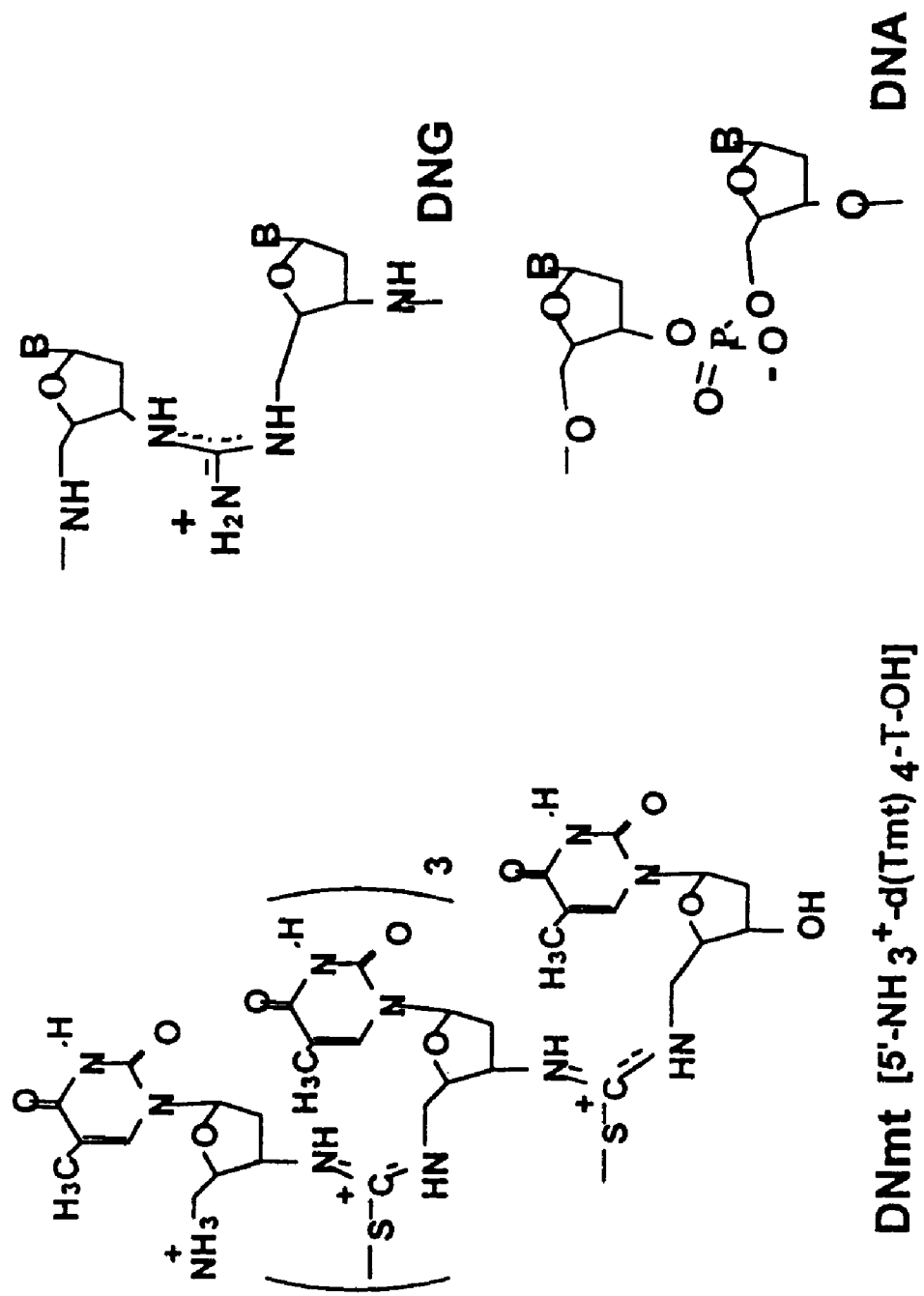
FIG. 15. Structures of DNmt, DNG, and DNA linkages in Example VII.

CD, UV Spectroscopy and Data Collection. CD spectra were obtained on an OLIS RSM circular dichroism spectrophotometer. Scans were run from 320 nm to 190 nm. Measurements were recorded at every nm. Ten scans were recorded, averaged and smoothed for each curve. Samples were held in a 1 cm path length cuvette at 25° C. UV spectra were recorded at λ=260 nm on a Cary 1E UV/vis spectrophotometer equipped with temperature programming. Spectrophotometer stability and λ alignment were checked prior to initiation of each melting point experiment. For the T$_m$ determinations derivatives were used. Data were recorded every 1.0 deg. The samples were heated from 25–95° C. at 5 deg/min (FIG. 15), the annealing (95–5° C.) and the melting (5–95° C.) were conducted at 0.13 deg/min and the samples were brought back to 25° C. at a rate of 5 deg/min. The reaction solutions were equilibrated for 15 min at the highest and lowest temperatures.

Data Analysis. The raw data from the melting point determinations was subjected to Gaussian smoothing using Matlab 4. Calculations of kinetic/thermodynamic parameters were performed using the resulting database.

Figures 17, 18:
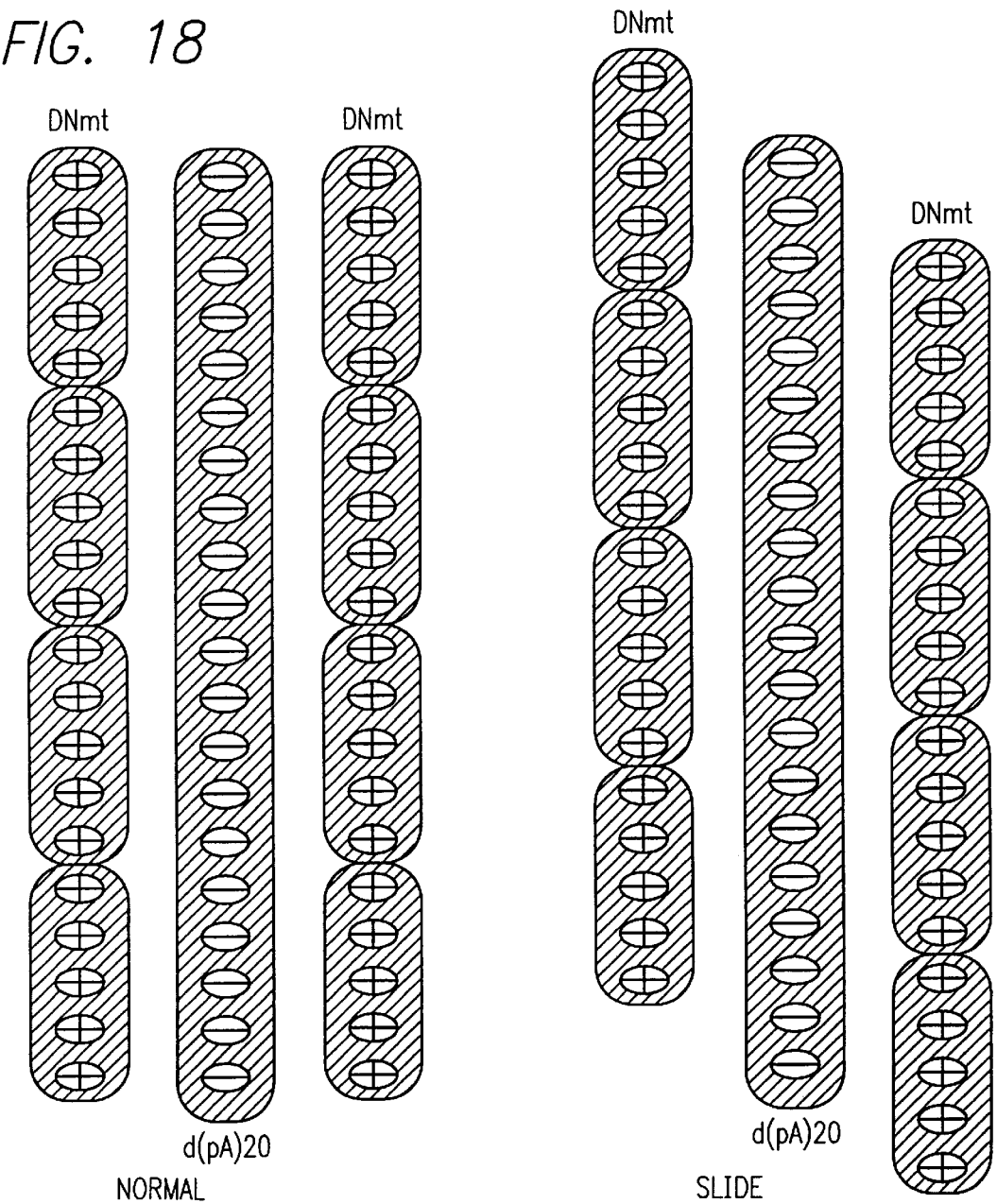
FIG. 17. Equation for Triplex Formation
FIG. 18. Process of Triplex Formation

Analysis of kinetic data for triplex formation. The equation for triplex formation that was employed (FIG. 17) describes the formation of the triplex (Tr) from the duplex (D) and the monomer (M), as individual strands. This equation could be interpreted as the reaction of double strand D with single strand M. However, the process of triplex formation may take place in different ways which is referred to as normal and slide (or dangling ends) (FIG. 18). (Arya, D. P.; Bruice, T. C. *Proceedings of the National Academy of Sciences, USA* 1999, 96, 4384; Blasko, A.; Dempcy, R. O.; Minyat, E. E.; Bruice, T. C. *Biochemistry* 1997, 36, 7821)

The expression of kinetic equations for the reactants and products (FIG. 19) can be accomplished by expressing the concentrations of strands in molar per base (M/base). The theory behind the "on" and "off" rates of the dissociation/association of the triplexes and the derivation of kinetic equations has been described in detail. (Arya, D. P.; Bruice, T. C. *Proceedings of the National Academy of Sciences, USA* 1999, 96, 4384; Blasko, A.; Dempcy, R. O.; Minyat, E. E.; Bruice, T. C. *Biochemistry* 1997, 36, 7821; Blasko, A.; Dempcy, R. O.; Minyat, E. E.; Bruice, T. C. *Journal of the American Chemical Society* 1996, 118, 7892; Rougee, M.; Faucon, B.; Mergny, J. L.; Barcelo, F.; Giovannageli, C.; Garestier, T.; Helene, C. *Biochemistry* 1992, 31, 9269.) In FIG. 17, a triplex is formed from and dissociates to a duplex and a third monomer strand with rate constants k$_{on}$ and k$_{off}$. The associated rate for this reaction is given in FIG. 19. The limitations of using this model to similar studies of DNG$_2$·DNA triplexes have been previously discussed. (Dempcy, R. O.; Minyat, E. E.; Bruice, T. C. *Biochemistry* 1997, 36, 7821; Blasko, A.; Dempcy, R. O.; Minyat, E. E.; Bruice, T. C. *Journal of the American Chemical Society* 1996, 118, 7892). Letting D$_{tot}$=[D]+[Tr]; and M$_{tot}^T$=[M]+[Tr], where the subscript "tot" stands for the total concentration and superscript T stands for temperature, the monitored absorbance is a weighted combination of the absorbances of the trimer, dimer and monomer (FIG. 20) where α=[Tr]/Dtot.

The expressions for k$_{on}$ and k$_{off}$ were solved as previously reported. (Arya, D. P.; Bruice, T. C. *Proceedings of the National Academy of Sciences, USA* 1999, 96, 4384; Blasko, A.; Dempcy, R. O.; Minyat, E. E.; Bruice, T. C. *Biochemistry* 1997, 36, 7821; Blasko, A.; Dempcy, R. O.; Minyat, E. E.; Bruice, T. C. *Journal of the American Chemical Society* 1996, 118, 7892; Rougee, M.; Faucon, B.; Mergny, J. L.; Barcelo, F.; Giovannageli, C.; Garestier, T.; Helene, C. *Biochemistry* 1992, 31, 9269.) The rate constants, k$_{on}$ and k$_{off}$ are functions of temperature and, therefore, can be expressed as Arrhenius equations (FIG. 21) where R=1.98 cal/mo19 K, and T$_{ref}$ is the reference temperature at which the rate constant k$_{ref}$ applies. In a plot of 1n(k$_{on/off}$) vs. 1/T–1/T$_{ref}$, the thermodynamic parameters {E$_{on/off}$R} can be obtained as the slope and the kinetic k$_{on}$M$_{tot}$, k$_{off}$ parameter as the y intercept.

Figure 23:
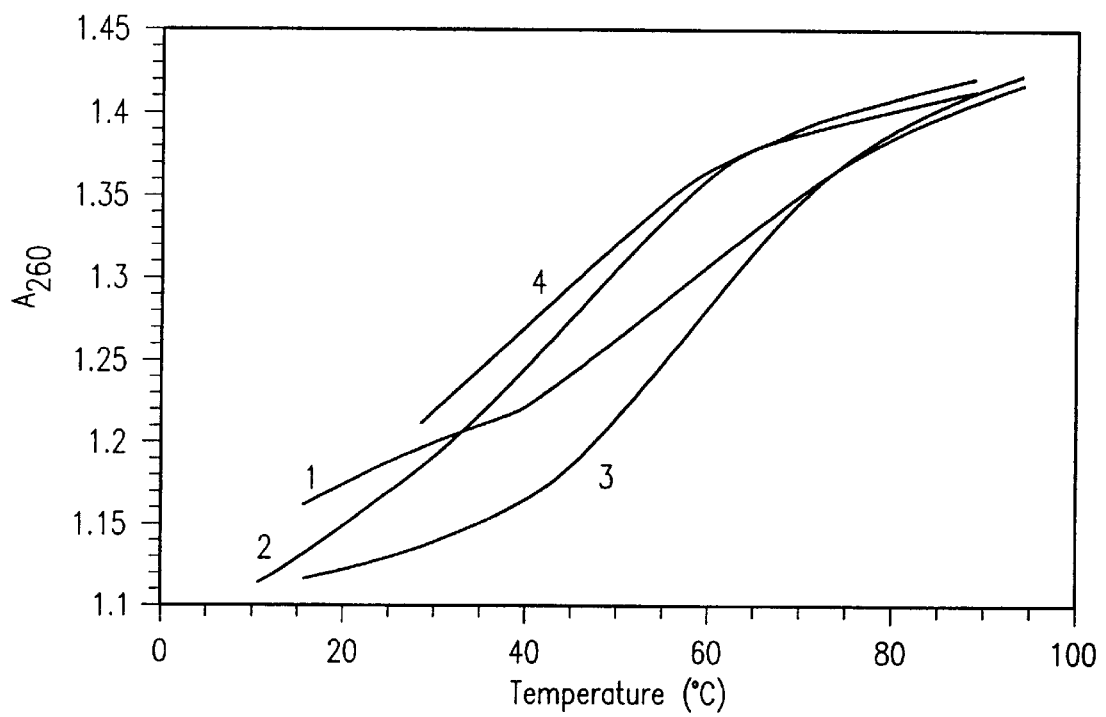
FIG. 23. Effect of the heating/cooling rate on the extent of association/dissociation of the triplex of oligo 1 SEQ ID NO. 1 with 5'—NH$_3^+$—d(Tmt)$_4$—T—OH at $4.0\times10^{-5}$ M/base monomer concentration. 1-fast heating (5 deg/min); 2-slow annealing (0.13 deg/min); 3-slow melting (0.13 deg/min); 4-fast cooling (5 deg/min).
Figure 24:
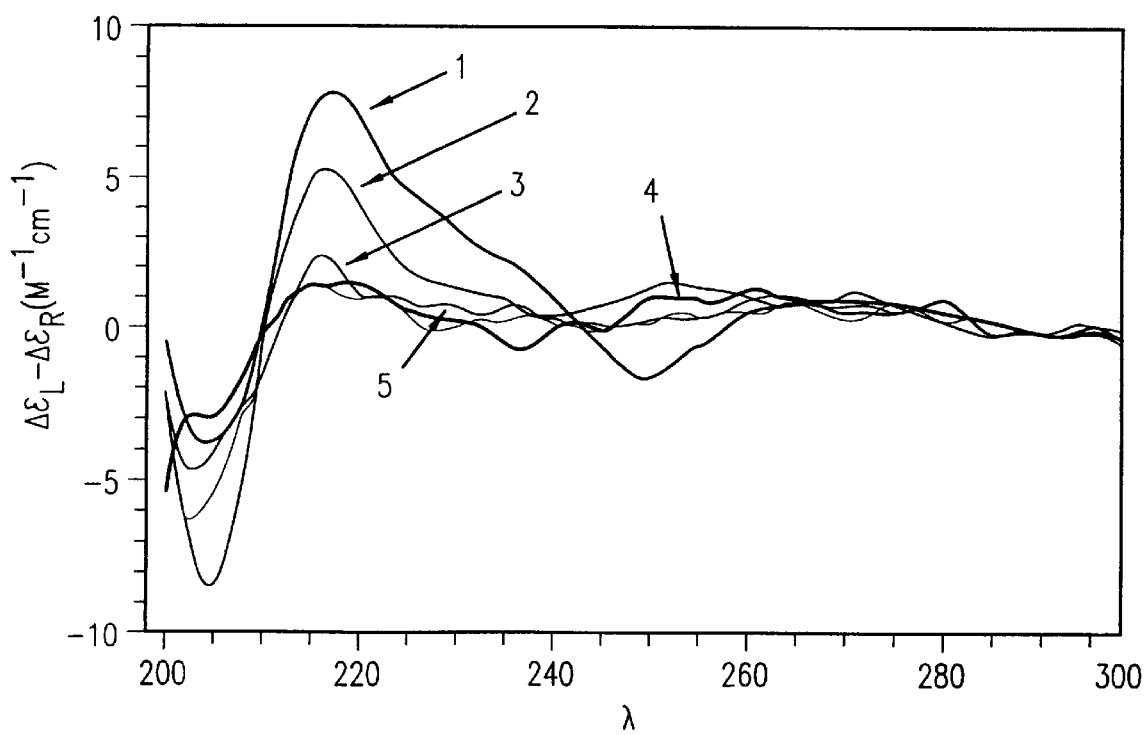
FIG. 24. Difference CD spectra of oligos (1–5) SEQ ID NO. 1; SEQ ID NO. 2; SEQ ID NO. 3; SEQ ID NO. 4; SEQ ID NO. 5 binding to DNmt. The ratio of d(pA$_x$C$_y$) to DNmt was 1:2. Spectrum of 1 in Figure refers to the difference spectra [1-(DNmt$_2$·1 SEQ ID NO. 1) triplex]. Solution conditions: $1.0\times10^{-5}$ M in oligomer, 0.10 M KCL, 10 mM phosphate buffer, pH 6.8 at 25° C.

Kinetics of triplex association/dissociation and Circular Dichroism studies: An expression which provides the temperature dependence of the rate constants for association (k$_{on}$) and dissociation (k$_{off}$) of oligomeric triplex (FIG. 17) is provided in FIG. 21. As the rate of the heating and cooling increases, the rate of equilibration of the species lags such that the hysteresis becomes more marked. The four ramps depicted in FIG. 23 are the variation of the absorbance (A$_{260}$) vs. temperature. The melting temperatures, T$_m$, the association and dissociation kinetic and thermodynamic parameters were determined by UV thermal analysis for the triplexes of short strand DNA homooligomers {1–5} SEQ ID NO. 1; SEQ ID NO. 2; SEQ ID NO. 3; SEQ ID NO. 4; SEQ ID NO. 5 with the S-methylthiourea linked nucleoside {5'—NH$_3^+$-d(Tmt)$_4$—T—OH {DNmt$_5$}. As experienced with previously reported studies of DNmt binding to poly (dA) and poly(rA), (Arya, D. P.; Bruice, T. C. *Journal of the American Chemical Society* 1998, 120, 12; Arya, D. P.; Bruice, T. C. *Proceedings of the National Academy of Sciences, USA* 1999, 96, 4384) the Job plots clearly establish a minimum at ca. 67% 5'—NH$_3^+$—d(Tmt)$_4$—T—OH which corresponds to the formation of a 2:1 (5'—NH$_3^+$-d(Tmt)$_4$—T—OH)$_2$·(DNA) complex. The hyperchromicity in binding decreased considerably on going from oligo 1 to oligo 5 SEQ ID NO. 1; SEQ ID NO. 2; SEQ ID NO. 3; SEQ ID NO. 4; SEQ ID NO. 5. Circular dichroism studies show evidence of triple-helical association dependent on the mismatch content. The CD spectrum of an oligomer solution can give valuable information about the conformation of the oligomers as single strands or in association with other DNA oligomers. Any CD signals observed in the absorbance band of the bases (230–300 um) are due to spatial organization of the bases in a chiral structure, such as a helix, under the influence of the chiral sugar backbone. Base stacking interactions magnify this effect and give rise to the strong CD signals observed for DNA and RNA oligomers and polymers. When DNmt is associated with complementary DNA, the CD spectrum of the complex does not match the spectrum calculated from the weighted sums of the CD spectra for the constituent oligomers. FIG. 24 shows the difference spectra of 5'—$NH_3^+$—$d(Tmt)_4$—T—OH binding to oligos 1–5 SEQ ID NO. 1; SEQ ID NO. 2; SEQ ID NO. 3; SEQ ID NO. 4; SEQ ID NO. 5. Clear differences can be seen indicating that different degree of structural changes have taken place in the three oligomers because of their association. The negative peaks at 250 nm gradually disappear on going from oligo 1 to oligo 5 SEQ ID NO. 1; SEQ ID NO. 2; SEQ ID NO. 3; SEQ ID NO. 4; SEQ ID NO. 5 and there is considerable weakening of the positive signal at 212 nm. For the complementary $d(pA)_{20}$-oligo 1 SEQ ID NO. 1, the difference spectra shows the largest changes out of all the samples. As the amount of mismatch increases, difference spectra drop in amplitude indicating that the degree of association is weakening. For the non-complementary oligomers 4 and 5, SEQ ID NO. 4; SEQ ID NO. 5 the difference spectra are very flat indicating little association that reorganizes the bases of the nucleosides.

Figure 25A:
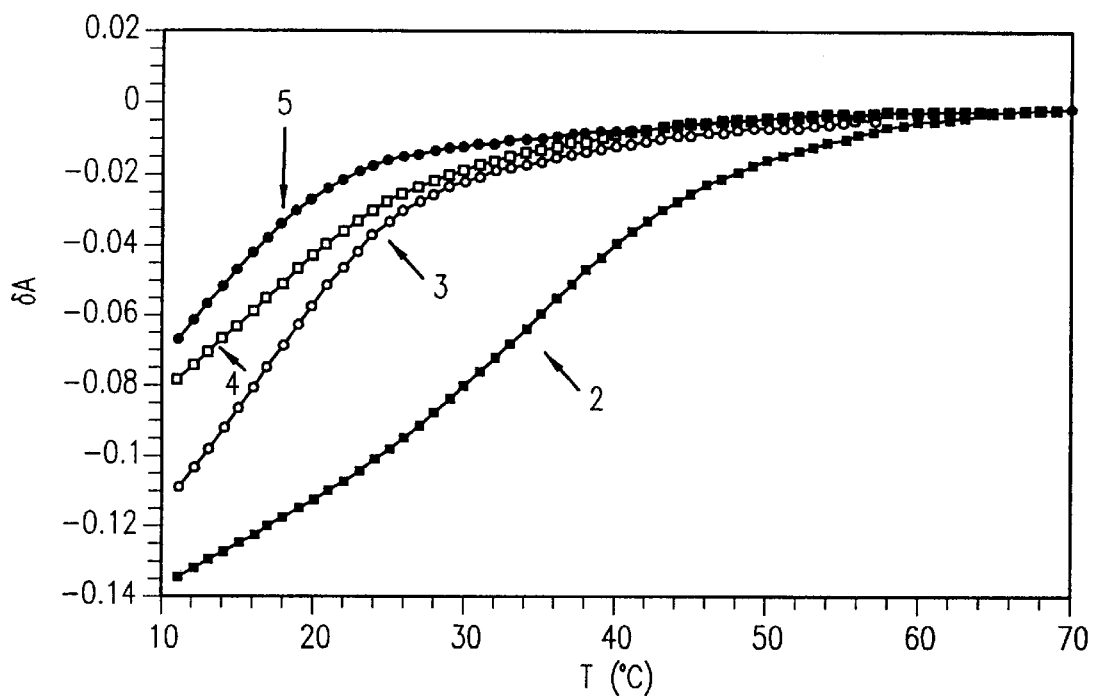
FIG. 25(a–b). Melting curves of the (DNmt)$_2$·d(pA$_x$C$_y$) triplexes (with oligos 2–5 SEQ ID NO. 2; SEQ ID NO. 3; SEQ ID NO. 4; SEQ ID NO. 5) Solution conditions: 16×106 M in oligomer, 0.10 M KCL, 10 mM phosphate buffer, pH 6.8 at 25° C.
FIG. 25b. First derivatives of the (DNmt)$_2$·d (pA$_x$C$_y$) triplexes (with oligos 1–5) SEQ ID NO. 1; SEQ ID NO. 2; SEQ ID NO. 3; SEQ ID NO. 4; SEQ ID NO. 5.
Figure 25B:
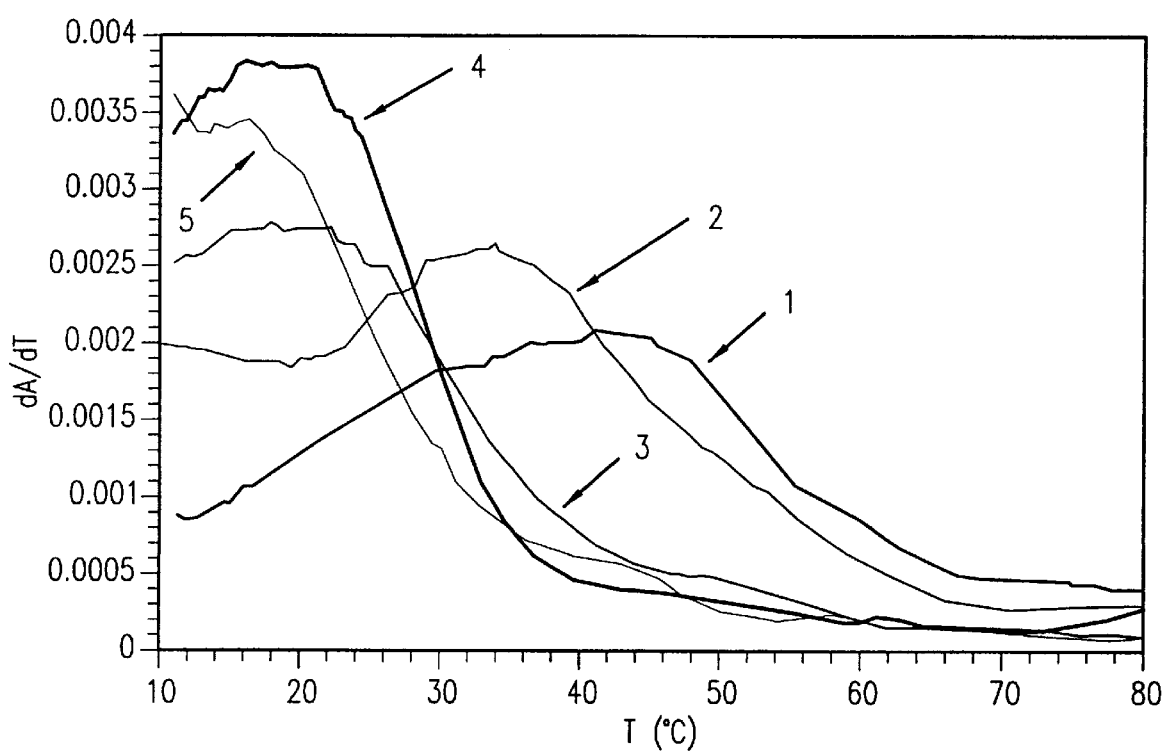
Figure 26A:
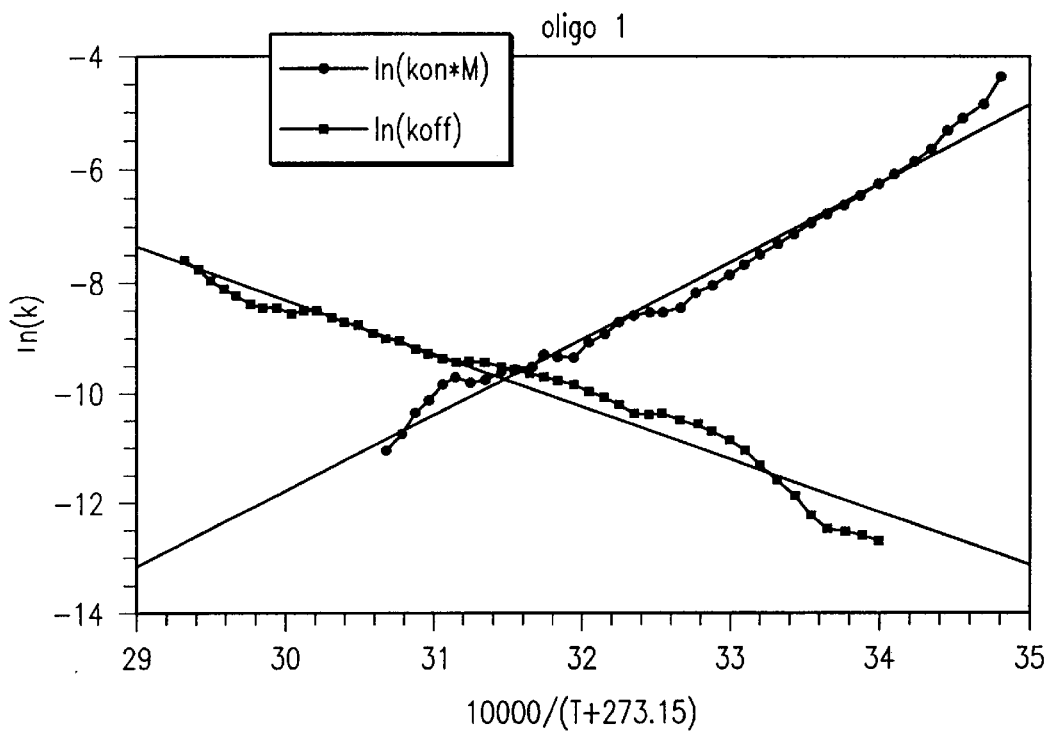
FIGS. 26a–e. Arrhenius plots {1n(k) vs 1/T} for the triplexes of DNmt with oligos 1–5 SEQ ID NO. 1; SEQ ID NO. 2; SEQ ID NO. 3; SEQ ID NO. 4; SEQ ID NO. 5. Solution conditions: $16\times10^{-6}$ M in oligomer, 0.10 M KCl, 10 mM phosphate buffer, pH 6.8 at 25° C.
Figure 26B:
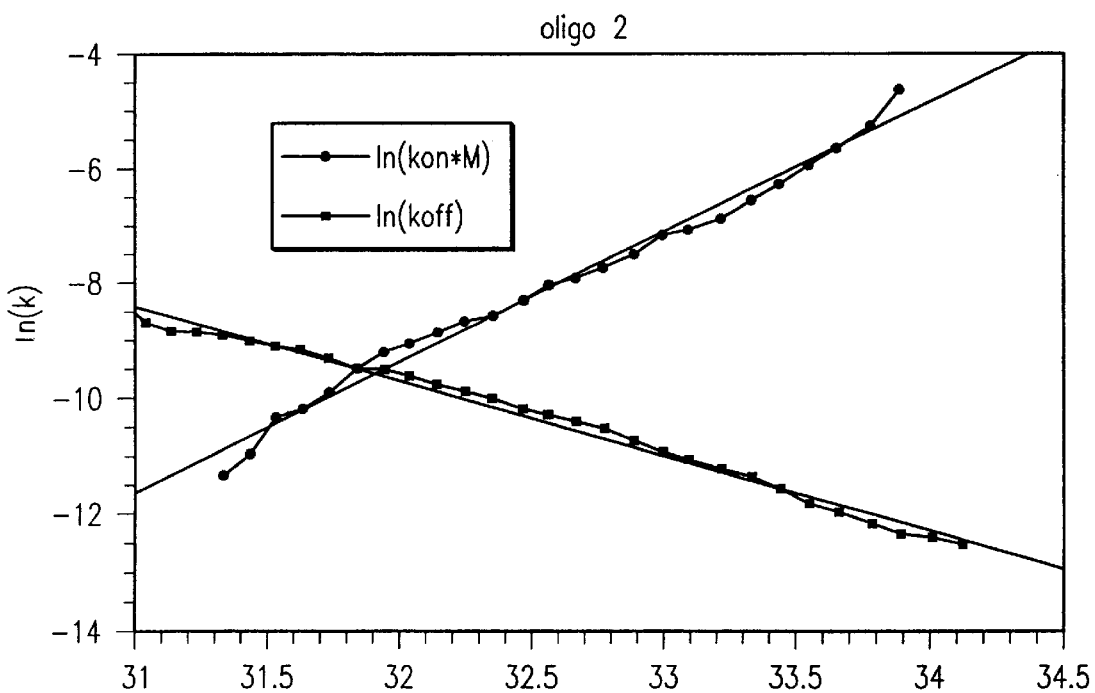
Figure 26C:
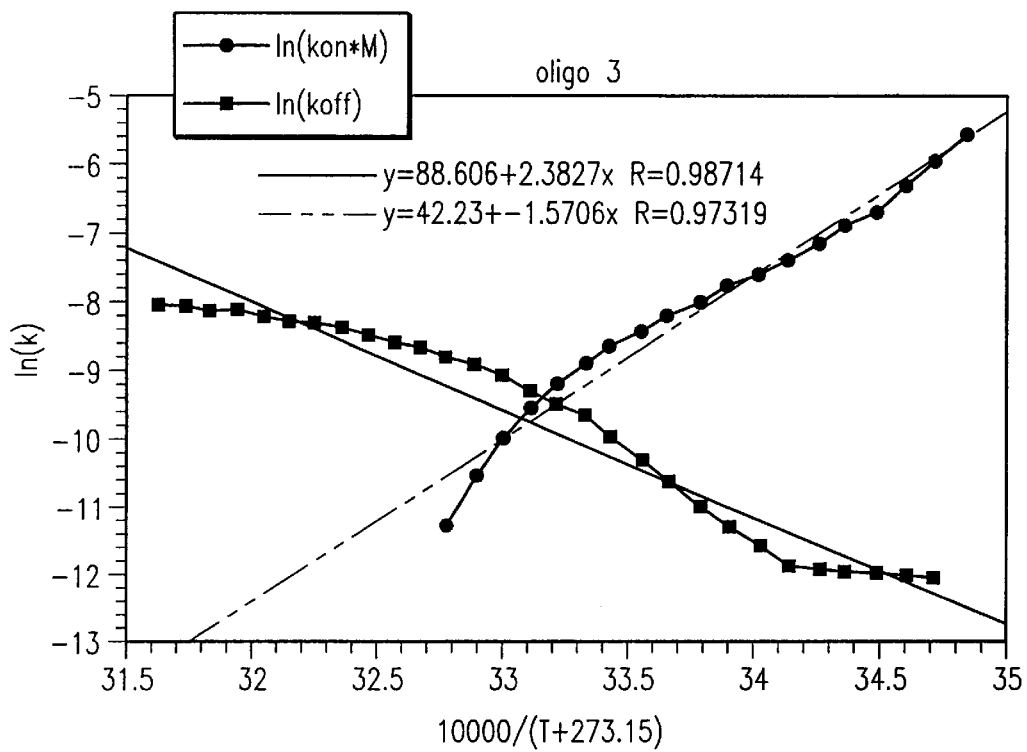
Figure 26D:
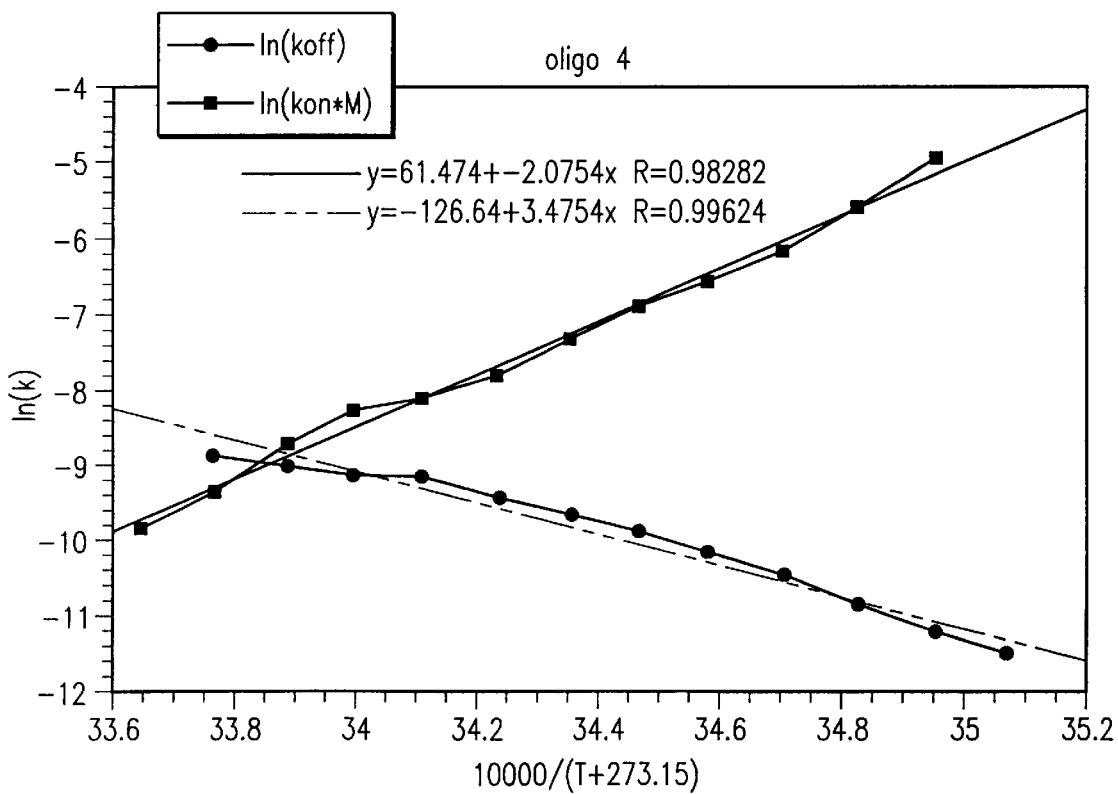
Figure 26E:
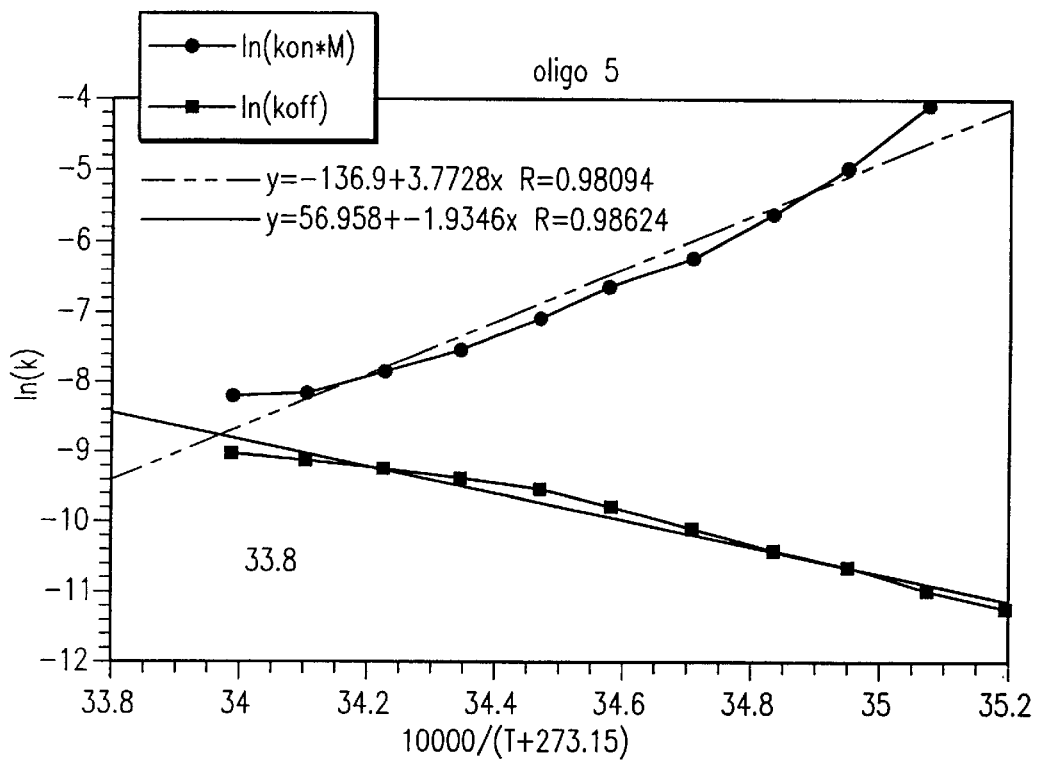

$T_m$ decreases sharply with the increase in mismatch character. FIG. 25a shows the melting curves and the first derivatives of DNmt triplexes with oligos 1–5 SEQ ID NO. 1; SEQ ID NO. 2; SEQ ID NO. 3; SEQ ID NO. 4; SEQ ID NO. 5 showing the drop in $T_m$ as the mismatch increases. On comparing the $T_m$ from oligo 1 to oligo 2 SEQ ID NO. 1;SEQ ID NO. 2 (20% mismatch), Tm of the triplex drops from 48 to 39° C. and is less than 20° C. for oligos 4 and 5 SEQ ID NO. 4; SEQ ID NO. 5 (60% and 50% mismatch respectively). The melting and cooling curves exhibit hysteresis behavior in the temperature range of 10–95° C. at 0.13 deg/min thermal rate. The heating and cooling curves were used to calculate rate constants for association ($k_{on}$) and dissociation ($k_{off}$) of triplex formation (FIG. 17). (Arya, D. P.; Bruice, T. C. Proceedings of the National Academy of Sciences, USA 1999, 96, 4384; Blasko, A.; Dempcy, R. O.; Minyat, E. E.; Bruice, T. C. Biochemistry 1997, 36, 7821; Blasko, A.; Dempcy, R. O.; Minyat, E. E.; Bruice, T. C. Journal of the American Chemical Society 1996, 118, 7892). At equilibrium, both heating and cooling curves coincide satisfying the mathematical condition da/dt=0 (α=fraction of duplex engaged in the triplex). FIG. 21 provides $k_{on}^{ref}$ and $k_{off}^{ref}$ at a given reference temperature.

Plots of ln(k) vs. 1/T were found to be linear between the temperature range of 10C to 45° C. From the intercepts of plots of $ln(k_{on})$ and $ln(k_{off})$ vs. $1/T-1/T_{ref}$, $k_{on}^{ref}M_{tot}$ and $k_{off}$, respectively, were obtained. The arrhenius plots of DNmt triplex with oligo 1–5 SEQ ID NO. 1; SEQ ID NO. 2; SEQ ID NO. 3; SEQ ID NO. 4; SEQ ID NO. 5at a concentration of 16ptM are shown in FIG. 26a–e. The intersection of cooling {$ln(k_{on}$·M) vs 1/T} and melting {$ln(k_{off})$ vs 1/T}curves represent the melting point of the triplex. As is evident from FIG. 27, the intersection of the lines moves to a lower temperature on going from oligo 1 to oligo 5, SEQ ID NO. 1; SEQ ID NO. 2; SEQ ID NO. 3; SEQ ID NO. 4; SEQ ID NO. 5 indicating the destabilization of the helix as the mismatch content is raised.

The rate constants $k_{on}$ and $k_{off}$ at a given temperature (288K–310K) are also dependent on the mismatch content. At physiological temperature (37° C.), $k_{on}$ increases with decrease in mismatch whereas $k_{off}$ decreases with increase in mismatch (FIG. 22). From oligo 1 to oligo 5, SEQ ID NO. 1; SEQ ID NO. 2; SEQ ID NO. 3; SEQ ID NO. 4; SEQ ID NO. 5 $k_{on}$ decreases from 11.5 to 0.01 $M^{-1} s^{-1}$, $k_{off}$ increases from $2.7 \times 10^{-5}$ to $445 \times 10^{-5}$ $s^{-1}$. The free energies of formation get less negative as the mismatch content increases and become positive for oligos 4 and 5SEQ ID NO. 4;SEQ ID NO. 5, as the duplex becomes the more stable species ($T_m$ for 4 and 5 SEQ ID NO. 4; SEQ ID NO. 5 is less than 20° C., implying complete dissociation of the triplex at 37° C.).

Figure 27:
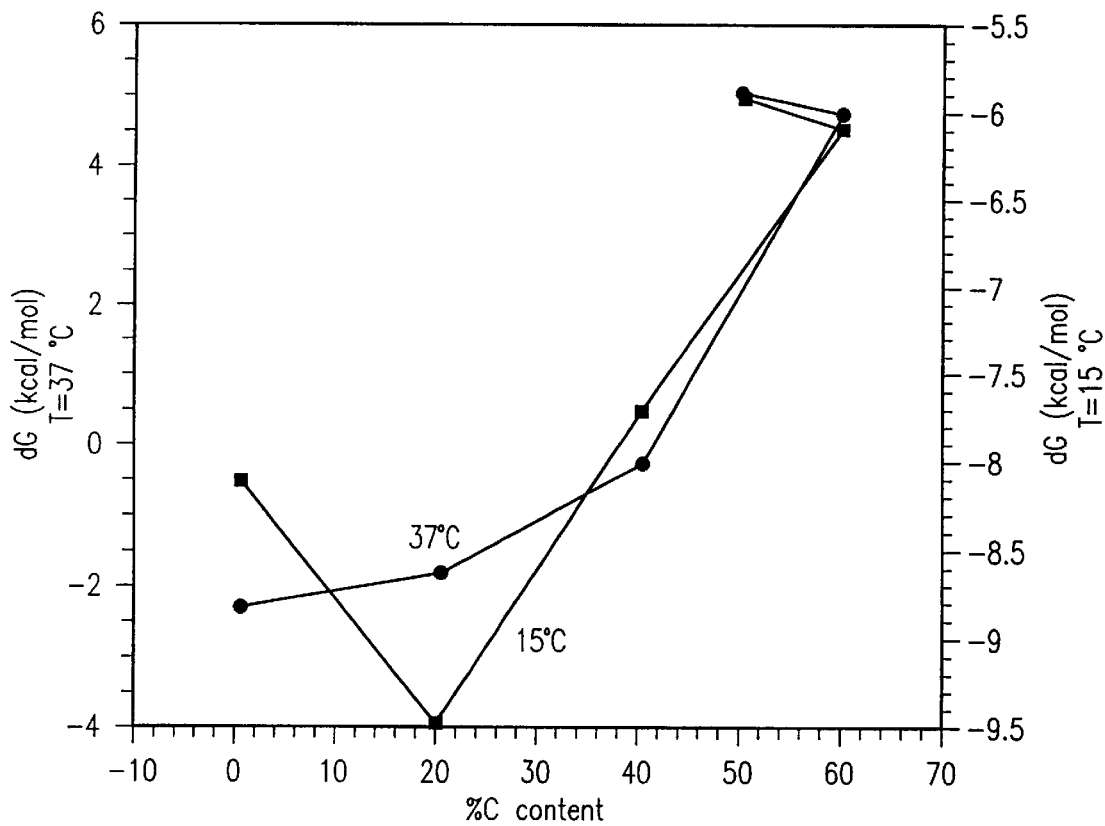
FIG. 27. Plots of variation of free energies (15° C. and 37° C.) of formation of the $(DNmt)_2 \cdot d(pA_xC_y)$ triplex with increase in mismatch (% C) of oligos 1–5 SEQ ID NO. 1; SEQ ID NO. 2; SEQ ID NO. 3; SEQ ID NO. 4; SEQ ID NO. 5.
Figure 28:
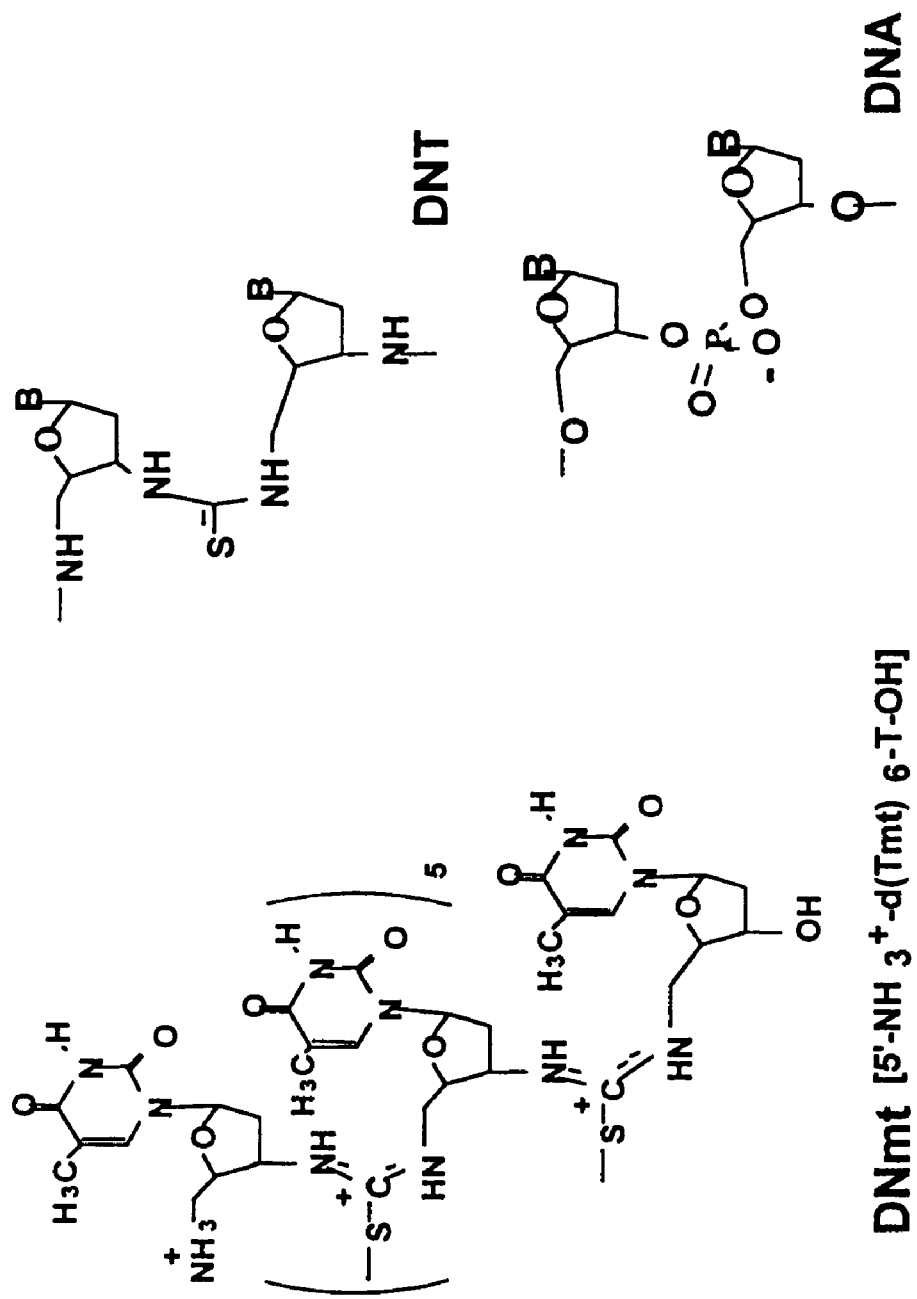
FIG. 28. Structures of DNmt, DNT, and DNA linkages in Example VIII.

At lower temperatures (15° C.), there seem to be nonspecific electrostatic interactions which seem to stabilize DNmt triplex with oligo 2 SEQ ID NO. 6 more than oligo 1 SEQ ID NO. 7. On going to oligos 3–5 SEQ ID NO. 3; SEQ ID NO. 4; SEQ ID NO. 5 however, stability of the triplex decreases considerably, as expected from specific H-bonded triplex formation. For example, at 15° C., $\Delta\Delta G_{(1-5)}$ for triplex formation is 2.2 kcal/mol compared to $\Delta\Delta G_{(1-5)}$ of 7.3 kcal/mol at 37° C. Oligo 4 SEQ ID NO. 4 (60% C), forms a slightly more stable triplex (by 0.33 kcal/mol at 37° C. and by 0.2 kcal/mol at 15° C., margin of error being 0.2 kcal/mol, $\Delta T_m = 3.9°$ C.) compared to oligo 5 SEQ ID NO. 4 (50% C, alternating A and C). The plots of change in free energy with variation in mismatch content at different temperatures are shown in FIG. 27 and illustrate the loss of stability of the $DNmt_2$-DNA triple helices complexed with non-complementary oligos 2–4 SEQ ID NO. 2; SEQ ID NO. 3; SEQ ID NO. 4; SEQ ID NO. 5.

The $k_{on}$ values for the formation of $DNmt_2$·DNA triple helices, on average, have been found to be (Arya, D. P.; Bruice, T. C. Proceedings of the National Academy of Sciences, USA 1999, 96, 4384) one order of magnitude larger than those found for a DNA triplex having the length of 22 bp at [NaCl]=0.02–0.30 M. (Rougee, M.; Faucon, B.; Mergny, J. L.; Barcelo, F.; Giovannageli, C.; Garestier, T.; Helene, C. Biochemistry 1992, 31, 9269; Manzini, G.; Xodo, L. E.; Gasparato, D. Journal of Molecular Biology 1990, 213, 833). The increase in $k_{off}$ values on increasing the mismatch content parallels the increase observed for DNA·$DNA_2$ triple helices. (Rougee, M.; Faucon, B.; Mergny, J. L.; Barcelo, F.; Giovannageli, C.; Garestier, T.; Helene, C. Biochemistry 1992, 31, 9269). On the other hand, the decrease in $k_{on}$ values upon increase of mismatch (% C) is in contrast to that observed for DNA·$DNA_2$ triple helices (no change in $k_{on}$ values was observed with the mismatch oligos in that study). (Rougee, M.; Faucon, B.; Mergny, J. L.; Barcelo, F.; Giovannageli, C.; Garestier, T.; Helene, C. Biochemistry 1992, 31, 9269). These comparisons are only qualitative since the ionic strength acts in opposite direction for DNmt relative to DNA and the composition of the 22-mer DNA oligonucleotide differs from the short strand DNA oligonucleotides in this study.

In conclusion, these results demonstrate that the polycation 5'—$NH_3^+$—$d(Tmt)_4$—T—OH binds to homo-oligomers $d(pA)_x$ with high affinity and with base-pair specificity to provide triple-stranded helices. The electrostatic attraction between polycation 5'—$NH_3^+$—$d(Tmt)_4$—T—OH and polyanion $d(pA)_x$ stabilizes the triple helical hybrid structures. The free energies of triplex formation ($\Delta G°$), become appreciably less negative as the ratio of C to A increases (oligos 1 to 5) SEQ ID NO. 1; SEQ ID NO. 2; SEQ ID NO. 3; SEQ ID NO. 4; SEQ ID NO. 5. $T_m$ of the $DNmt_2$·DNA triple helices decreases sharply with the increase in mismatch character. Thymidyl DNmt is thus shown to bind to DNA oligomers with high fidelity under physiological conditions. Synthetic efforts to design longer DNmt sequences, coupled with studies of $DNmt_n$·DNA complexes involving complementary and mismatch sequences should help in further development of this novel class of putative antisense/antigene agents.

EXAMPLE VIII

Solid-phase synthesis of oligomeric Deoxynucleiethiourea (DNT) and Deoxynucleic S-methylthiourea (DNmt): A neutral/polycationic analogue of DNA This example demonstrate the solid phase synthesis of the DNT and DNmt compounds of the invention.

Materials.

The concentrations of nucleotide solutions were determined using the extinction coefficients (per mol of nucleotide) calculated according to the nearest neighboring effects. For d(Tmt)$_5$ and d(Tt)$_5$ (where mt and t stand for S-methylthiourea and thiourea is linkages respectively) we used $\epsilon_{626}$=8700 M$^{-1}$ cm$^{-1}$ (Blasko, A., Dempcy, R. O., Minyat, E. E. & Bruice, T. C. (1996) *Journal of the American Chemical Society* 118, 7892–7899; Blasko, A., Dempcy, R. O., Minyat, E. E. & Bruice, T. C. (1997) *Biochemistry* 36, 7821–7831) A Cary 1E UV/vis spectrophotometer equipped with temperature programming and regulation and a thermal melting software package were used for data collection at $\lambda$=260nm.

Synthesis:

All reactions were performed under a positive atmosphere of dry nitrogen. $^1$H NMR spectra were obtained at 400 MHz unless indicated otherwise and $^{13}$C NMR spectra at 125 MHz; chemical shifts ($\delta$) are relative to internal TMS, coupling constants (J) are in hertz. Splitting patterns are designated singlet (s), doublet (d), triplet (t), quartet (q), multiplet (m), or broad (b). IR spectra were taken in KBr pellet using Perkin Elmer 1300 spectrophotometer. TLC was carried out on silica gel (kieselgel 60 F$_{254}$), 0.25 mm coated commercial silica plates and visualized by UV-light. Flash column chromatography employed E. Merck silica gel (kieselgel 60, 200–400 mesh) as the stationary phase. Individual mobile phase systems are described in the experimental section. CPG (Controlled Pore Glass) resin with long chain alkylamines was purchased from Sigrna Chemical Co. (St. Louis, Mo.).

5'—N-MmTr-5'-deoxythymidine (Compound 23a):

To a solution of 5.0 g (0.02 mole) of 5'-amino-5'-deoxythymidine in 120 ml of anhydrous pyridine was added 8 g (0.0259 mole) of monomethoxytrityl chloride, followed by addition of 75 mg of dimethyaminopyridine and 2.0 ml of triethylamine. The resulting solution was then stirred at 80° C. for 6 hr. The solvent was then rotovaporated to about 10 ml, 200 ml of water added and the product extracted into 3×200 ml of ether. The organic layer was dried over sodium sulfate, rotovaporated and chromatographed in methylene chloride:methanol (95:5) to give 8.1 g of the product (78.8%). $^1$H NMR-400 MHz (d$_6$-DMSO+CDCl$_3$): $\delta$ 10.737 (1H, br, NH), 7.475 (4H, d, J=7.6 Hz, MTr-ortho H), 7.635 (2H, d, J 8.8 Hz, MTr-meta H), 7.268 (4H, t, J=7.2 Hz, MmTr-meta H), 7.185 (2H, d, J=7.2 Hz, MmTr-para H), 7.06 (1H, d, J=1.2 Hz, 6—H), 6.80 (2H, d, J=8.8 Hz, MmTr-ortho H), 6.289 (1H, t, J=6.4 HZ, 1'—H), 5.037 (1H, br, NH), 4.185 (1H, m, 3'—H), 4.004 (1H, m, 4'—H), 2.904 (1H, br, OH), 2.288 (2H, m, 5'—H), 2.050 (2H, m, 2'—H), 1.788 (3H, s, Me). $\delta$ $^{13}$C (d$_6$-DMSO-125 MHz): 163.656, 167.268, 150.054, 145.525, 134.244, 129.275, 127.894, 127.302, 125.724, 112.570, 110.165, 85.472, 83.370, 71.058, 69.525, 54.596, 45.538, 12.060. IR (KBr pellet): 3460 (O—H), 3285, 3246 (N—H), 3070 (Aromatic C—H), 2950 (Aliphatic C—H), 1680 (C=O). FABm/z: 513.2 (M+H)$^+$.

5'—N-MmTr-3'-mesvl-5'-deoxythymidine (Compound 23b):

A solution of 5.5 g (10.68 mmole) of 5'—N-MmTr-5'-deoxythymidine in 30 ml of anhydrous pyridine was cooled to 0° C. 1.83 g (16.10 mmole) of methanesulfonyl chloride was added dropwise and the resulting solution stirred at 0° C. for 6 hr. The solvent was rotovaporated to about 5 ml, 200 ml of water added and the product extracted into 3×100 ml of chloroform. The organic layer was dried over sodium sulfate and rotovaporated to give 5.6 g of the product (88%). $^1$H NMR-400 MHz (d$_6$-DMSO): $\delta$ 11.665 (1H, br, NH), 7.820 (1H, d, J=1.2 Hz, 6—H), 7.519–7.390 (1OH, m, MmTr), 7.29 (2H, d, J=8.8 Hz, MmTr-meta H), 7.050 (2H, d, J=8.8 Hz, MmTr-ortho H), 6.396 (1H, t, J=6.8 Hz, 1'—H), 5.250 (1H, m, 3'—H), 4.799 (11H, m, 4'—H), 3.931 (3H, s, OMe), 3.537 (1H, s, NH), 2.931 (2H, m, 5'—H), 2.716 (2H, m, 2'—H), 2.018 (3H, d, J=1.2 Hz, Me). $^{13}$C $\delta$ (d$_6$-DMSO-125 MHz): 163.679, 157.755, 150.558, 147.915, 139.798, 137.256, 128.874, 127.576, 127.387, 126.461, 112.715, 109.817, 80.312, 79.563, 54.908, 41.472, 38.643, 37.558, 35.032, 11.924. FABm/z: 592.2 (M+H)$^+$.

5'—N-MmTr-3'-azido-3', 5'-dideoxythymidine (Compound 25):

To a solution of 5.0 g (8.436 mmole) of 5'—N-MmTr-3'-mesyl-5'-deoxythymidine in 50 ml of DMF was added 15.626 g (84 mmole) of potassium phthalimide in 17 ml of water. The resulting solution was stirred at 100° C. for 0.5 hr and then cooled to room temperature. The solvent was rotovaporated to about 5 ml and 100 ml of water added to precipitate the product. The white product was dried under vacuum and redissolved in anydrous DMF. 4g (80 mmole) of lithium azide was added and the solution heated to 110° C. for 24 hrs. TLC shows the appearance of azido product [CHCL$_3$ (95): MeOH(5) on silica, Rf=0.7]. The solvent was rotovaporated, 100 ml of water added and the product extracted into chloroform (3×100 ml). The organic layer was dried and concentrated to give 4.9 g of product (90%). $^1$H NMR-400 MHz (d$_6$-CDCl$_3$): $\delta$ 9.872 (1H, br, NH), 7.48–7.18 (12H, m, MmTr), 7.093 (1H, d, J=1.2 Hz, 6—H), 6.83 (2H, dd, J =6.8 Hz, 2.0 Hz, MmTr-ortho H), 6.163(1H, t, J=6.8 Hz, 1'—H), 4.260 (1H, m, 3'—H), 3.90 (1H, m, 4'—H), 3.784 (3H, s, OMe), 2.44 (2H, m, 5'—H), 2.34 (2H, m, 2'—H), 2.016 (1H, s, NH), 1.895 (3H, d, J=1.2 Hz, Me). $^{13}$C $\delta$ (d$_6$-CDCL$_3$-125 MHz): 163.836, 157.911, 150.241, 149.429, 145.666, 145.628, 137.404, 135.022, 129.598, 128.263, 127.898, 127.754, 126.404, 123.696, 113.180, 111.481, 84.200, 83.365, 70.036, 60.454, 55.075, 44.969, 37.368, 21.265, 14.077, 12.559. FABm/z: 592.2 (M+H)$^+$.

5'—N-MmTr-3'-isothiocyanato-3', 5'-dideoxvthymidine (Compound 27):

In a solution of 2.0 g (3.71 mmole) of 5'—N-NhnTr-3'-azido-3', 5'-dideoxythymidine in 50 ml of Pyridine/water (1:1) was bubbled H$_2$S gas for 25 minutes. The resulting solution was stirred at room temperature for 12 hrs. Argon was bubbled through the solution to precipitate the sulfur. After filtration, the solvent was evaporated and the product dried under vacuum. The brown product (amine-26) was redissolved in anhydrous methylene chloride. 1.50 g (6.4 mmole) of thiocarbonylpyridone was added and the resulting solution stirred at room temperature for 6 hr. TLC analysis in 80% EtOAc: 20% Hexanes shows complete disappearance of the amine (Rf=0.1). The product has a Rf value of 0.8 and pyridone of 0.45. The solvent was rotovaporated and the product chromatographed in EtOAC: Hexanes (1:1) to give 1.7 g of the product (82.9%). $^1$H NMR-200 MHz (d$_6$-DMSO+CDCl$_3$): $\delta$ 9.67 (1H, s, NH), 7.493 (1H, s, 6—H), 7.48–7.26 (15H, m, trityl-H), 6.27 (1H, t, J=6.8 Hz, 1'—H), 4.606 (1H, m, 3'—H), 4.139 (1H, m, 4'—H), 3.62 (1H, m, 5'—H), 2.79 (2H, m, 2'—H), 1.56 (3H, s, Me). $\delta$ $^{13}$C (d$_6$-DMSO+CDCl$_3$): 156.892, 149.746, 145.954, 145.628, 142.206, 134.611, 127.568, 127.385, 126.128, 125.112, 109.765, 84.408, 83.40, 80.256, 55.44, 44.978, 11.668. IR (KBr pellet): 3190, 3050 (Aromatic C—H), 2044 (N=C=S), 1687 (C=O). FAB m/z: 555.4 (M+H)$^+$.

Figure 29:
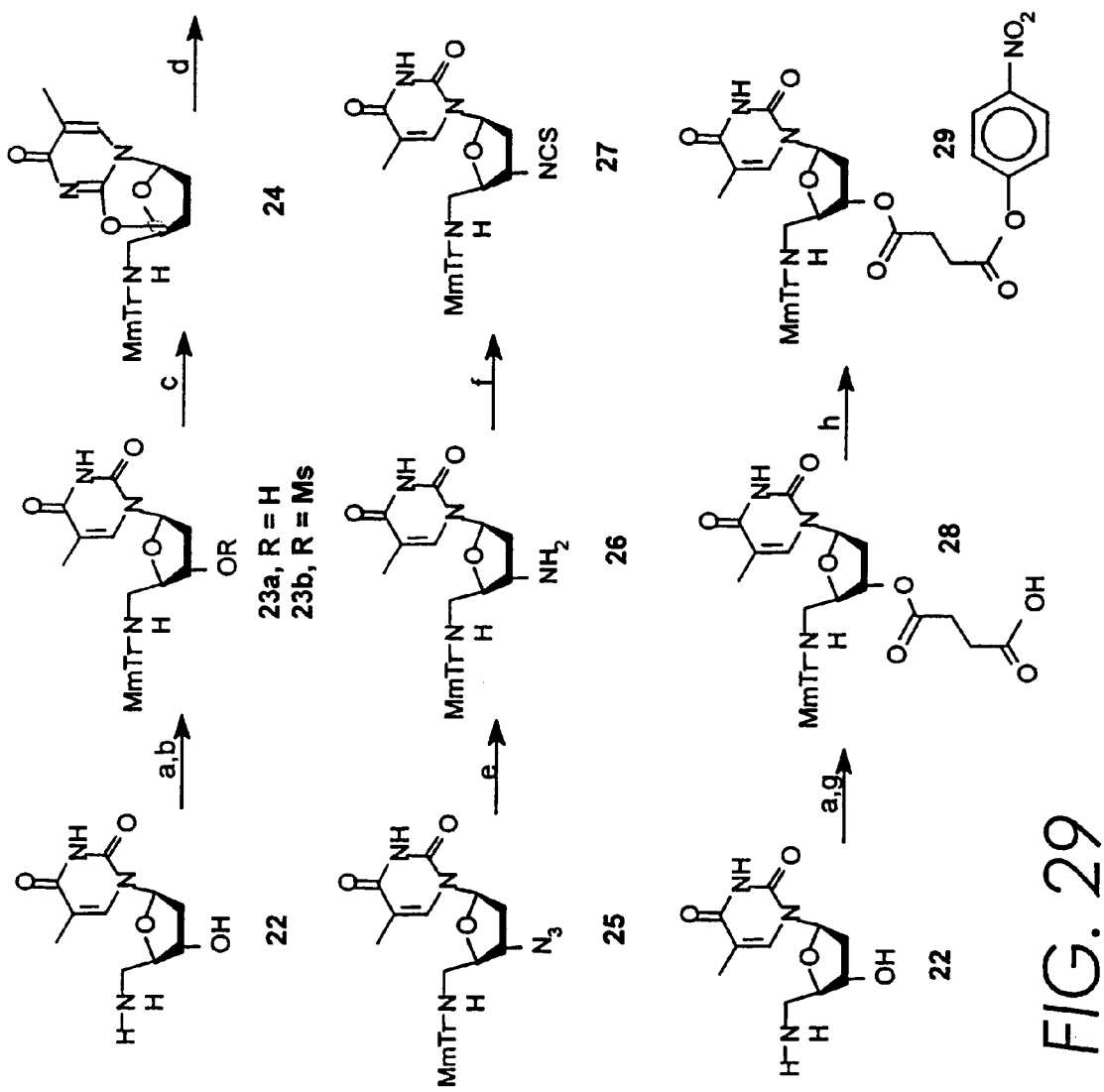
FIG. 29. Synthesis of thymidyl monomer for solid phase synthesis. (a) MmTr—Cl, Pyridine, DMAP(2 mol %), 89%, (b) 1.3 equiv. MsCl, Pyridine, 0° C. to rt, 88%; (c) KPhTh, DMF, $H_2O$, 100° C., 20 min (d) $LiN_3$, DMF, 110° C. 90%; (e) $H_2S$, Pyridine, 4 hrs, rt., 90%; f) Thiopyridone, $CH_2Cl_2$, 4 hr, 88%, (g) Succinic Anhydride, DMAP, Pyridine, (h) 4-Nitrophenol, DMAP, $Et_3N$.

Solid Phase Synthesis:

The monomer 27 (FIG. 29) for the SPS of oligothymidyl DNmts is obtained by protecting the 5'—NH$_2$ group of 5'-amino-5'-deoxythymidine (22) with monomethoxytrityl chloride and converting the 3'—OH to 3'-isothiocyanate in 5 steps (Dempcy, R. O., Browne, K. & Bruice, T. C. (1995) *Proceedings of the National Academy of Sciences, USA* 92; Arya, D. P. & Bruice, T. C. (1998) *Journal of the American Chemical Society* 120, 12,419–12,427) The 3'—OH was converted to the mesylate 23b which upon reaction with Potassium phthalimide in DMF followed by Lithium azide gives the azide 24 in excellent yields. Compound 24 was hydrogenated and reacted with thiocarbonylpyridone in $CH_2Cl_2$ to give monomer 27 in high yields. (Arya, D. P. & Bruice, T. C. (1998) *Journal of the American Chemical Society* 120, 12,419–12,427; Kim, S. & Yi, K. Y. (1986) *Journal of Organic Chemistry* 51, 2613–2615.) ControlPore Glass (CPG) resin with long chain alkylamine was chosen as a convenient commercially available support with a linker that was cleavable by mild base. The synthesis was designed to be compatible with standard DNA synthesis techniques to facilitate future synthesis of DNmt-DNA conjugates (Barawkar, D. A. & Bruice, T. C. (1998) *Proceedings of the National Academy of Sciences, USA* 95, 1104–11052) Analogous to DNA synthesis, 3'—OH of 22 was converted to the activated nitrophenyl ester 29, which was loaded as the first base on the resin. (Atkinson, T. & Smith, M. (1990) in *Solid-Phase Synthesis of Oligodeoxyribonucleotides by the Phosphotriester method*, ed. Gait, M. J. (Oxford University Press, New York), pp. 35–81)

Figure 30:
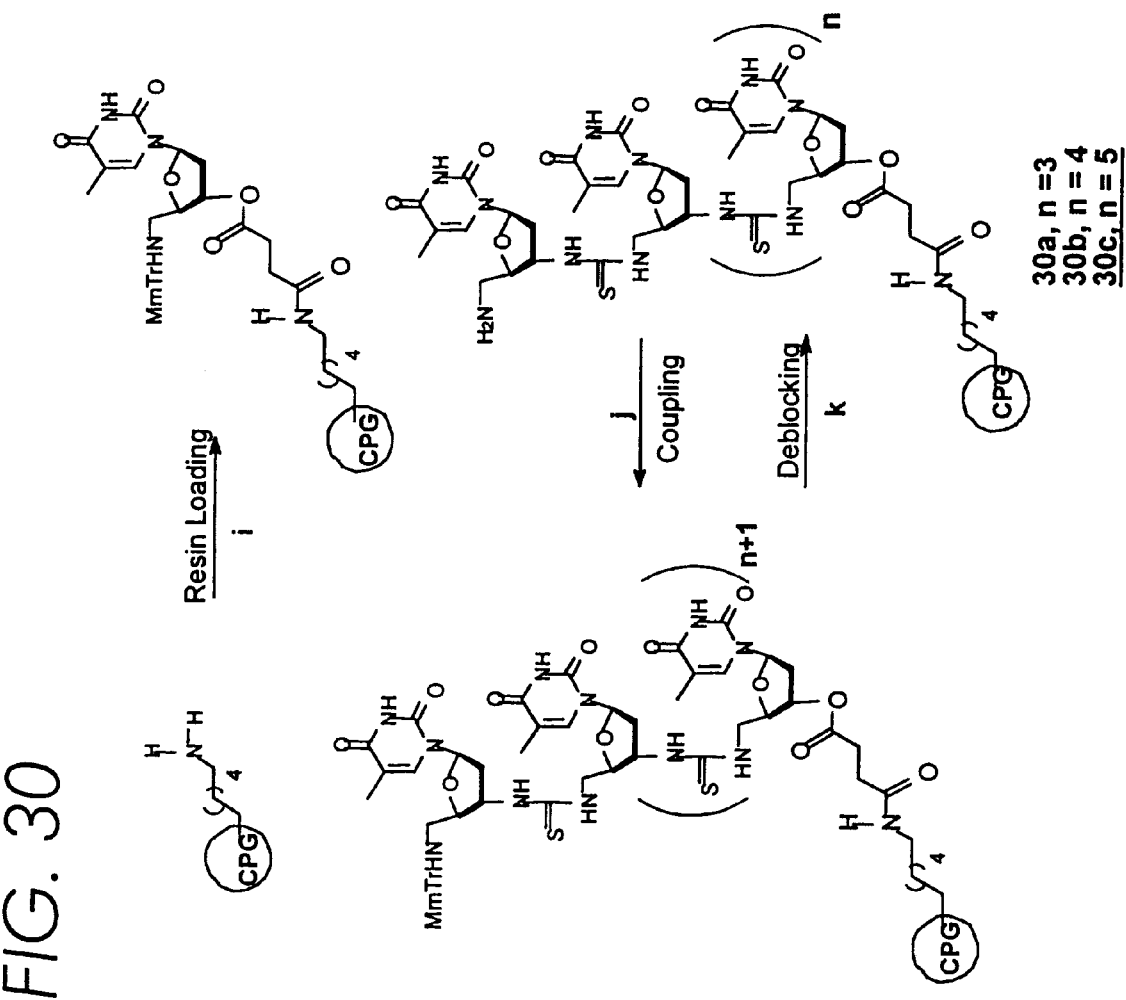
FIG. 30. Solid Phase Synthesis of DNT. (i) Pyridine, DMF, DMAP, monomer (8). (j) Coupling: Pyridine, monomer (6), DMAP (2 equiv.), (k) Deblocking: 4% dichloroacetic acid in dichloromethane.

The coupling reaction involves the addition of (27) to a 5'-aminothymidyl residue on the resin. In a typical synthesis, 36 mg of resin was placed in 0.5 ml Pyridine in a 3 ml reaction vial. Stock solutions of the isothiocyanate (27) (30 mM, 1.0 ml), DMAP (12 mM) in pyridine were added and the vial was agitated for 4 hr. The addition step was repeated twice to insure a complete reaction and then the resin was washed with copious amounts of pyridine, methanol and ether. The resulting 5'-MmTr protected oligomer is deblocked with 4% dichloroacetic acid in $CH_2Cl_2$ and the cycle began again (FIG. 30). The addition/deblocking cycle was repeated 6 more times to produce the seven unit oligomer.

Figure 31:
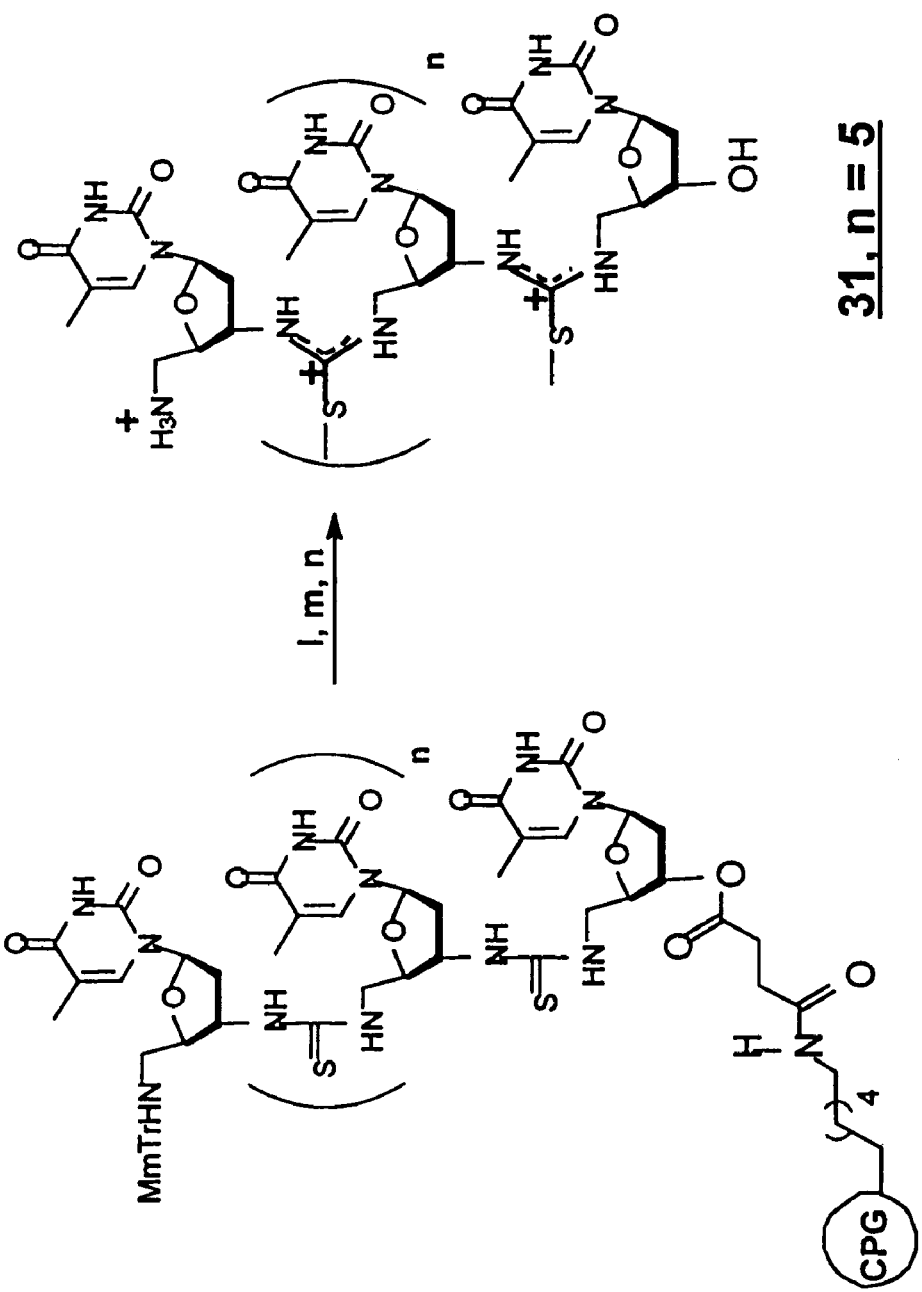
FIG. 31. Solid phase synthesis of DNmt. (1) MeI, EtOH, (m) $NH_4OH$, rt, (n) 4% dichloroacetic acid in dichloromethane.

The thiourea was methylated with 2 ml methyl iodide for 4 hr. The 5'-MmTr group was removed in 4% DCA and the resin washed with methanol, ether. The product was cleaved from the resin by treatment with $NH_4OH$ at room temperature. The oligomer can be cleaved from the resin before methylation to give the corresponding thiourea (30a–c) as well (DNT). Methylation of the tritylated thiourea can be performed in solution as well as on the solid phase. HPLC analysis of the crude DNmt product showed the desired product in >90% purity with an estimated coupling yield averaged over the seven additions of 87% (determined by UV analysis of absorbance of monomethoxy trityl cation). The deprotected DNmt oligomer 30 [5'—$NH_3^+$—d(Tmt)$_7$—OH] was purified on a preparative Alltech WCX cation exchange column employing 1.50 M ammonium acetate buffer, pH 6.0, as the mobile phase to give the pure oligomer (FIG. 31). Mass spectroscopic analysis indicates the expected mass for the singly charged [m/z=2019, calculated for $(M+H)^+$: 2019] form of the oligomeric DNmt 30.

Binding studies and NMR:

As shown in Examples I—VI Thymidyl DNmt (5'—$NH_3^+$—d(Tmt)$_4$—T—OH) has much stronger affinity for DNA and RNA, due to electrostatic attractions, than DNA for RNA or vice versa. In order to further evaluate the high stability of DNmt·DNA complexes, binding of neutral DNT (Deoxynucleicthiourea) 30a to poly(dA) was studied.

Figure 32:
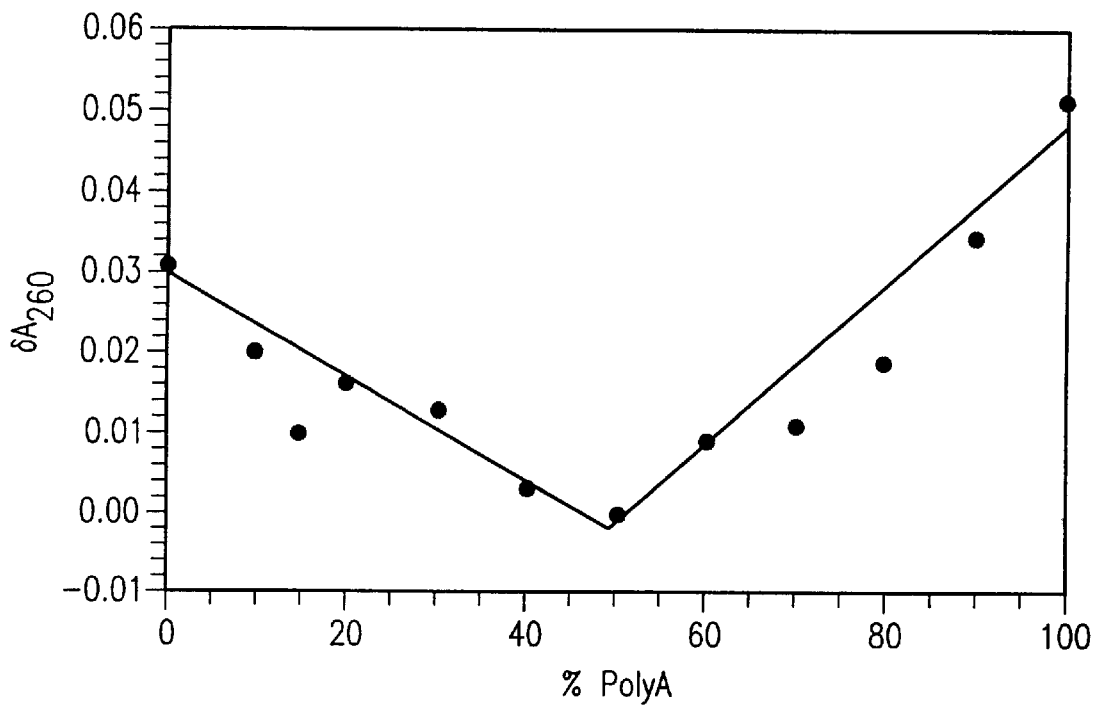
FIG. 32. Job plots of poly(dA) with 5'—$NH_3^+$—$d(Tt)_4$—T—OH in a concentration of $4.0 \times 10^{-5}$ M/base at 260 nm in 15 mM potassium phosphate (pH 7.5).
Figure 33:
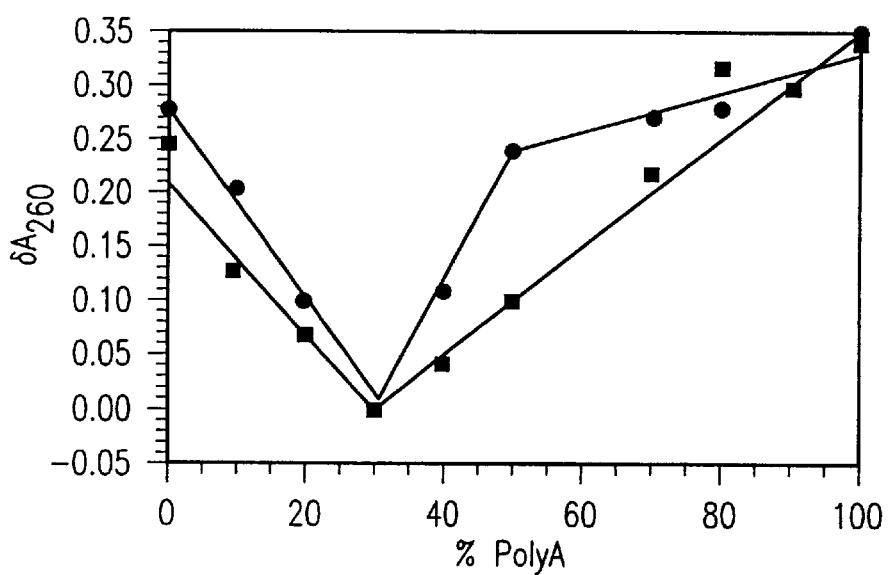
FIG. 33. Job plots of poly(dA) with 5'—$NH_3^+$—$d(Tmt)_4$—T—OH in a concentration of $4.0 \times 10^{-5}$ M/base at 260 nm in water (filled circle) and 15mM potassium phosphate (filled square).

To investigate the interaction of 30a{5'—$NH_3^+$-T$_t$-(T$_t$)$_4$—OH} with polynucleotides, UV continuous variation plots at different ionic strengths ($\mu$), wavelengths and temperatures were constructed. Mixtures of 30a with poly(dA) at 10° C. (FIG. 32) reach a minimum absorbance at a mole fraction of ~0.5 d(Tmt) to 0.5 d(Ap) (single phosphate-linked adenosyl unit). These numbers indicate that double stranded complexes are formed containing one d(Tt) for every d(Ap). This is in contrast to the 2:1 binding observed between DNmt·DNA complexes (FIG. 33) where triple helices are always observed. DNmt·DNA complexes always show a minimum at 2:1 and a break at 1:1 is observed only when mixing plots are carried out in pure water (FIG. 33). This is in agreement with the fact that DNmt·DNA complexes are destabilized upon addition of salt, as shown in Example I–VI. Melting curves for the duplex 30a·poly(dA) gave a melting point less than 15° C., showing much weaker binding compared to the DNmt·DNA triplexes. Changing the ionic strength (up to 0.2 M KCl) had no effect on the stability of the DNT·DNA duplex. As reflected in the 5A260 values in FIG. 32 and 33, the % hypochromicity is considerably less for DNT·DNA (FIG. 32) implying weaker binding for DNT·DNA duplex. Attempts to study binding of longer DNT (30b–c) were unsuccessful due to the lack of solubility of thiourea oligomers in aqueous solution.

Figure 34:
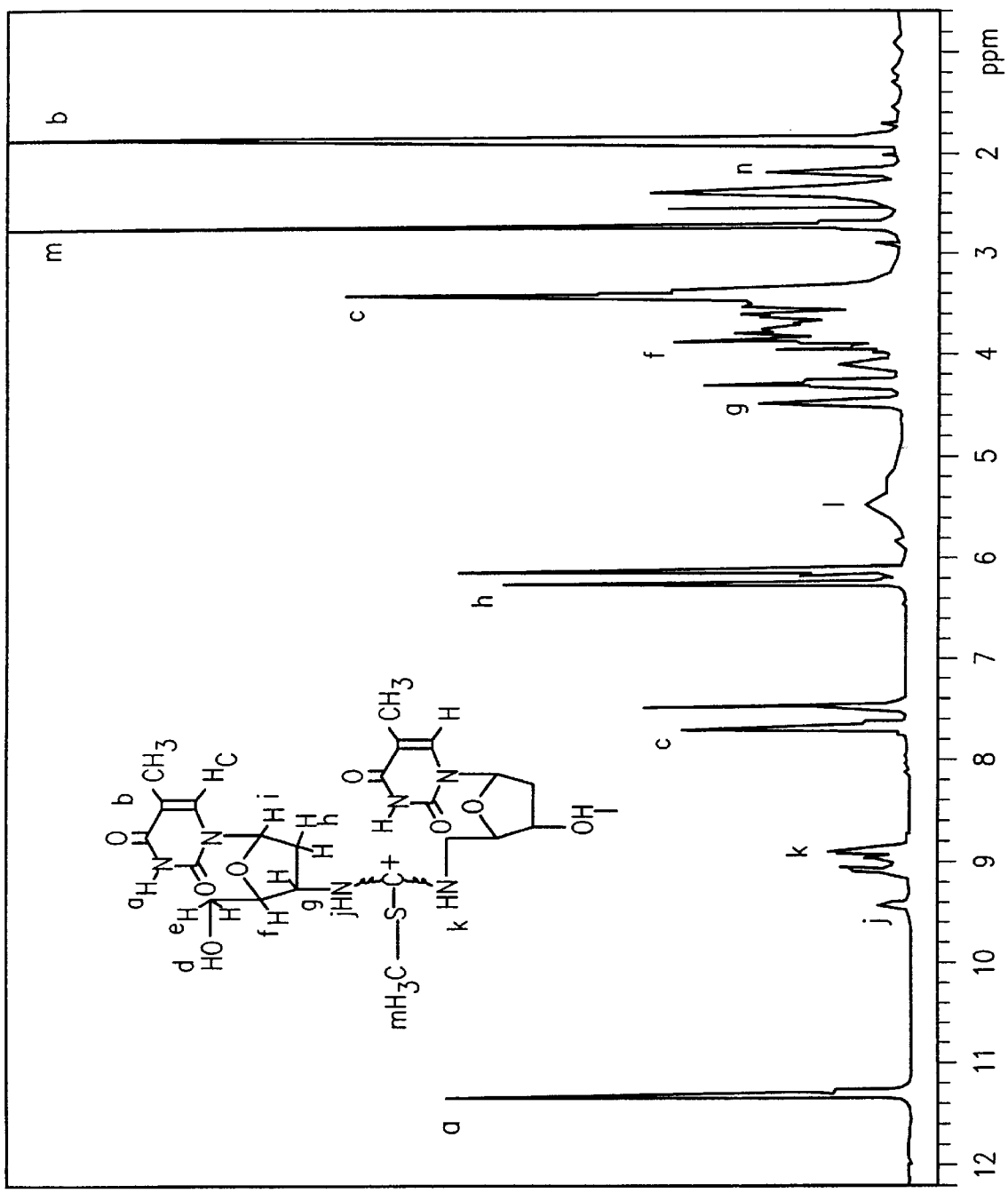
FIG. 34. $^1H$ NMR spectra of dinucleotide DNmt in DMSO-$d_6$ showing proton assignments in the backbone, sugar and base.
Figure 35:
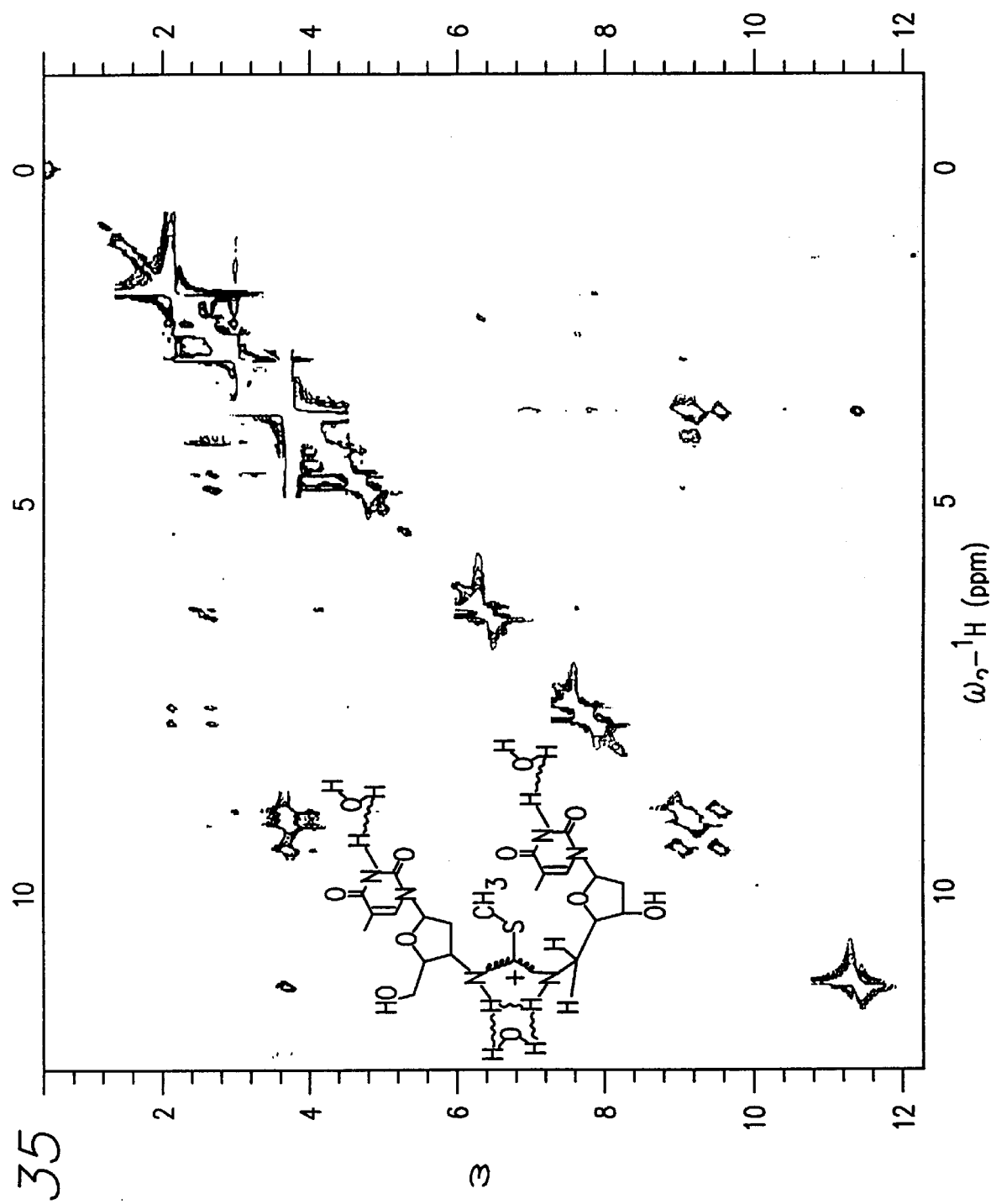
FIG. 35. NOESY spectra (200 ms) of dinucleotide DNmt and structure of the dimer showing NOE contacts (thin line).

Proton NMR experiments were carried out on a dimeric S-methylthiourea (For the synthesis of dimeric DNmt drawn in FIG. 35, see Arya, D. P. & Bruice, T. C. (1998) *Journal of the American Chemical Society* 120, 12,419–12,427) in DMSO and DMSO-water solutions. The $^1$H-NMR spectra of dimeric DNmt in pure DMSO is shown in FIG. 34 and shows the resolution of similar protons in the two sugar rings. Proton assignments were made based on a combination of COSY and TOCSY spectra. The methyl peak of the thiourea is considerably deshielded and appears at ~2.8 ppm. To evaluate the conformation of the S-methylthiourea backbone NOESY spectra were obtained at 50, 100 and 200 ms. The NOESY spectrum at 200 ms is shown in FIG. 35. Strong NOE contacts were observed between the backbone N—Hs (9.0 ppm) with no NOE contacts between the N—H and methyl protons (2.8 ppm). When water is present, strong NOE contacts are observed between water (3.5 ppm) and thymidyl N—H (11 ppm) as well as backbone N—H. No NOE contacts were observed between backbone methyl and sugar or base protons. The NOE contacts are shown in FIG. 35. The bases as drawn are most likely not stacked in the dimeric unit but would orient themselves in a polymer upon H-bonding to the opposite strand.

This example shows an efficient and rapid solid-phase method for the synthesis of thiourea and S-methylthiourea linked DNA.

This solid-phase synthesis provides for the rapid synthesis of DNmt/DNT oligomers, for combinatorial libraries and the synthesis of DNmt-peptide conjugates on solid phase.

Alternatively, the synthesis is accomplished nucleotide bases protected with base-labile phenoxyacetyl groups as described and the base protecting groups removed by subsequent ammonia treatment after removal of the MmTr protecting groups.

Attachment of charged functional groups to the 5'-amine of DNT (30a–c) should give them increased solubility and enable comparative studies of neutral thiourea with DNmt and DNG oligos.

Various publications are cited herein that are hereby incorporated by reference in their entirety.

As will be apparent to those skilled in the art in which the invention is addressed, the present invention may be embodied in forms other than those specifically disclosed without departing from the spirit or potential characteristics of the invention. Particular embodiments of the present invention described above are therefore to be considered in all respects as illustrative and not restrictive. The scope of the invention is as set forth in the appended claims and equivalents thereof, rather than being limited to the examples contained in the foregoing description.

What is claimed is:

1. A method for preparing oligonucleotides comprising synthesizing oligonucleotides comprising a backbone of alkyl or alkoxy thiourea linkages.

2. The method of claim 1 wherein said linkages are positively charged S-methylthiourea linkages.

3. The method of claim 1, wherein the oligonucleotides are synthesized in solution.

4. The method of claim 1, wherein the oligonucleotides are synthesized on a solid phase.

5. The method of claim 4, wherein the synthesis on a solid phase comprises the steps of:

a) attaching an activated nitrophenyl ester base to a solid phase, forming a solid phase tethered base;

b) attaching an isothiocyanate monomer, 5'—N-MmTr-3'-isothiocyanatio-3'-5'-dideoxynucleobase, to said solid phase tethered base; and c) successively attaching isothiocyanate monomers corresponding to a selected oligonucleotide sequence to the isothiocyanate monomer of step b), such that an oligonucleotide is synthesized.

6. The method of claim 5 wherein said solid phase is a resin.

7. The method of claim 5 wherein said 5'-N-MmTR-3', 5'-dideoxynucleobase comprises a base selected from the group consisting of Adenine, Guanine, Cytosine, Thymidine, or Uracil.

8. The method of claim 1, wherein the oligonucleotide comprises a nucleic acid sequence complementary to a selected nucleic acid sequence.

* * * * *